United States Patent
Hu et al.

(10) Patent No.: US 6,372,500 B1
(45) Date of Patent: Apr. 16, 2002

(54) EPISOMAL EXPRESSION CASSETTES FOR GENE THERAPY

(75) Inventors: Jim Hu, East York; Yu-Hua Chow, North York; Hugh O'Brodovich, Oakville; Lap-Chee Tsui, Etobicoke, all of (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 09/423,744

(22) PCT Filed: May 14, 1998

(86) PCT No.: PCT/CA98/00478

§ 371 Date: Nov. 12, 1999

§ 102(e) Date: Nov. 12, 1999

(87) PCT Pub. No.: WO98/51807

PCT Pub. Date: Nov. 19, 1998

(30) Foreign Application Priority Data

May 14, 1997 (CA) .............................. 2205076

(51) Int. Cl.[7] .................... C12N 15/63; C12N 15/00; A01N 63/00; A01N 43/04; A61K 48/00
(52) U.S. Cl. .................. 435/455; 424/93.21; 514/44; 435/320.1; 435/325; 435/366
(58) Field of Search .............. 435/320.1, 455; 514/44

(56) References Cited

U.S. PATENT DOCUMENTS

| | | | |
|---|---|---|---|
| 4,980,286 A | 12/1990 | Morgan et al. | 435/172.3 |
| 5,240,846 A | 8/1993 | Collins et al. | 435/240.1 |
| 5,399,346 A | 3/1995 | Anderson et al. | 424/93.21 |
| 5,585,362 A | 12/1996 | Wilson et al. | 514/44 |
| 5,624,820 A | 4/1997 | Cooper | 435/69.1 |
| 5,639,642 A | 6/1997 | Kjeldsen et al. | 435/697 |
| 5,639,661 A | 6/1997 | Welsh et al. | 435/252.3 |
| 5,641,662 A | 6/1997 | Debs et al. | 435/172.1 |
| 5,645,829 A | 7/1997 | Shockley et al. | 424/93.21 |
| 5,674,898 A | 10/1997 | Cheng et al. | 514/557 |
| 5,698,436 A | 12/1997 | Morgan et al. | 435/240.2 |

FOREIGN PATENT DOCUMENTS

| | | |
|---|---|---|
| WO | WO 92/03563 | 3/1992 |
| WO | WO 96/40963 | 12/1996 |
| WO | WO 97/09441 | 3/1997 |

OTHER PUBLICATIONS

Chow, Yu-Hua, et al., "Development of an epithelium-specific expression cassette with human DNA regulatory elements for transgene expression in lung airways" *Proc, Natl. Acad. Sci. U.S.A.*, 94:14695–14700 (1997).

(List continued on next page.)

*Primary Examiner*—Robert A. Schwartzman
*Assistant Examiner*—Q. Janice Li
(74) *Attorney, Agent, or Firm*—Gardner, Carton & Douglas

(57) ABSTRACT

The invention consists of episomal expression cassettes for expression of a transgene in gene therapy. The expression cassettes consist of regulatory elements of the human cytokeratin gene and a transgene. The invention also includes of liposomes for transfection of epithelial tissue with the cassettes in treatment of cystic fibrosis, emphysema, cancers of epithelial origin arising in the lung or other organs.

20 Claims, 33 Drawing Sheets

OTHER PUBLICATIONS

Griesenbach, U. et al., "Comparison between intratracheal and intravenous administration of liposome–DNA complexes for cystic fibrosis lung gene therapy," *Gene Therapy*, 5:181–188 (1998).

Gunther, Magali, et al., "An Sp1 Binding Site and the Minimal Promoter Contribute to Overexpression of the Cytokeratin 18 Gene in Tumorigenic Clones Relative to That in Nontumorigenic Clones of a Human Carcinoma Cell Line,," *Molecular and Cellular Biology*, 15(5):2490–2499 (1995).

Kerem, Bat–Sheva, et al., "Identification of mutations in regions corresponding to the two putative nucleotide (ATP-)-binding folds of the cystic firbrosis gene," *Proc. Natl. Acad. Sci. USA*, 87:8447–8451 (1990).

Neznanov, Nickolay, et al., A Regulatory Element within a Coding Exon Modulates Keratin 18 Gene Expression in Transgenic Mice. *The Journal of Biological Chemistry*, 272(44):27549–27557 (1997).

Pankov,Roumen et al., "AP–1, ETS, and Transcriptional Silencers Regulate Retinoic Acid–Dependent Induction of Keratin 18 in Embryonic Cells," *Molecular and Cellular Biology*, 14(12):7744–7757 (1994).

Rhodes, Katherine, et al., "A Regulatory Element of the Human Keratin 18 Gene with AP–1 –dependent Promoter Activity," *The Journal of Biological Chemistry*, 273(41):26534–26543 (1998).

Rommens, Johanna M., et al., "Identification of the Cystic Fibrosis Gene: Chromosome Walking and Jumping," *Science*, 245:1059–1065 (1989).

Thorey, Iramgard S., et al., "Embryonic Expression of Human Keratin 18 and K18–β–Galactosidase Fusion Genes in Transgenic Mice," *Developmental Biology*, 160:519–534 (1993).

Thorey, Irmgard S., et al., "Parent–Specific Expression of a Human Keratin 18/β–Galactosidase Fusion Gene in Transgenic Mice," *Developmental Dynamics*, 195:100–112 (1992).

Umezawa, Akihiro, et al., "Methylation of an ETS Site in the Intron Enhancer of the Keratin 18 Gene Participates in Tissue–Specific Repression," *Molecular and Cellular Biology*, 17(9):4885–4894 (1997).

Abe et al: J Cell Bio Sep 1990; 111:1197–1206.*

Akabas MH. J Bio Chem 2000; 275:3729–32.*

Boucher et al. J Clin Invest 1999 Feb. 103:441–445.*

Bowie et al. Science 1990 Mar; 247:1306–1310.*

Neznanov et al. Mol Cell Biol 1993 Apr.; 13:2214–23.*

Rudinger (Peptide Hormones 1976; Jun.;pp. 1–7.*

Smith et al . J Bio. Chem 1996 Apr.; 271:9947–54.*

Yew et al. Hum Gene Ther 1997 Mar. 8:575–584.*

Chow, Y.–H. et al., "Targeting transgene expression in lung airways with a novel human epithelial expression cassette", Seventh International Symposium of the Society of Chinese Bioscientists in America (Jul. 6–11, 1997) Toronto, Ontario abstract.

Chow, Y.–H. et al., "Targeting human CFTR expression in lung airways with a novel human epithelial expression", *Pediatr. Pulmonol.* Supplemental 14 Eleventh Annual North American Cystic Fibrosis Conference (Oct. 23–26, 1997) Nashville, Tennessee abstract.

O'Brodovich, H. et al., "Liposome–plasmid mediated gene transfer to the intact lung: the utility of an epithelial specific promoter", The Broken Arrow Meeting (1998)Mississauga, Ontario abstract.

Chow, Y.–H. et al., "Targeting transgene expression to airway submucosal glands, the prominent site of the human CFTR gene", First Annual Meeting of the American Society of Gene Therapy (May 28–31, 1998) Seattle, Washington oral presentation.

Chow, Y.–H., et al., "Directing transgene expression to airway epithelia, the primary target sites for lung gene therapy", Eighteenth International Congress of Genetics (1998) Beijing, China oral presentation.

Chow, Y.–H., et al., "Targeting transgene expression in airway submucosal glands, prominent sites of human CFTR expression", Pediatr. Pulmonol. Supplemental 17 Twelfth Annual North American Cystic Fibrosis Conference (Oct. 15–18, 1998) Montreal, Quebec abstract.

Steer, B. et al., An epithelial specific promoter prevents transgene expression in alveolar macrophages in vivo.Pediatr. Pulmonol. Supplement 17 Twelfth Annual North American Cystic Fibrosis Conference (Oct. 15–18, 1998) Montreal, Quebec abstract.

Koehler, D. et al., A human cytokeratin 18–based vector optimized for high–level expression in lung epithelial cells. Second Annual Meeting of the American Society of Gene Therapy (Jun. 6–9, 1999) Washington, DC absract.

* cited by examiner

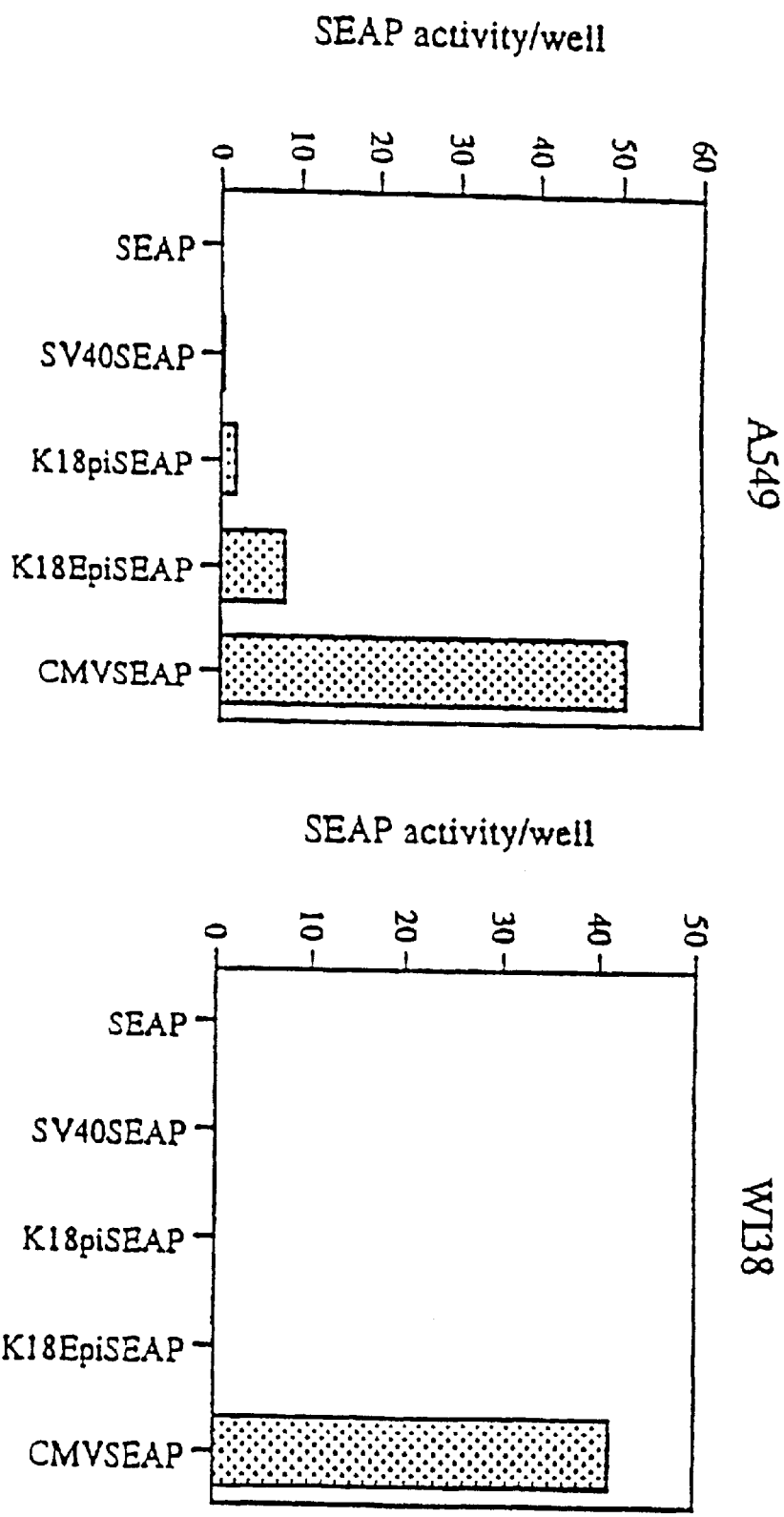
FIG. 5 (continued on next page)

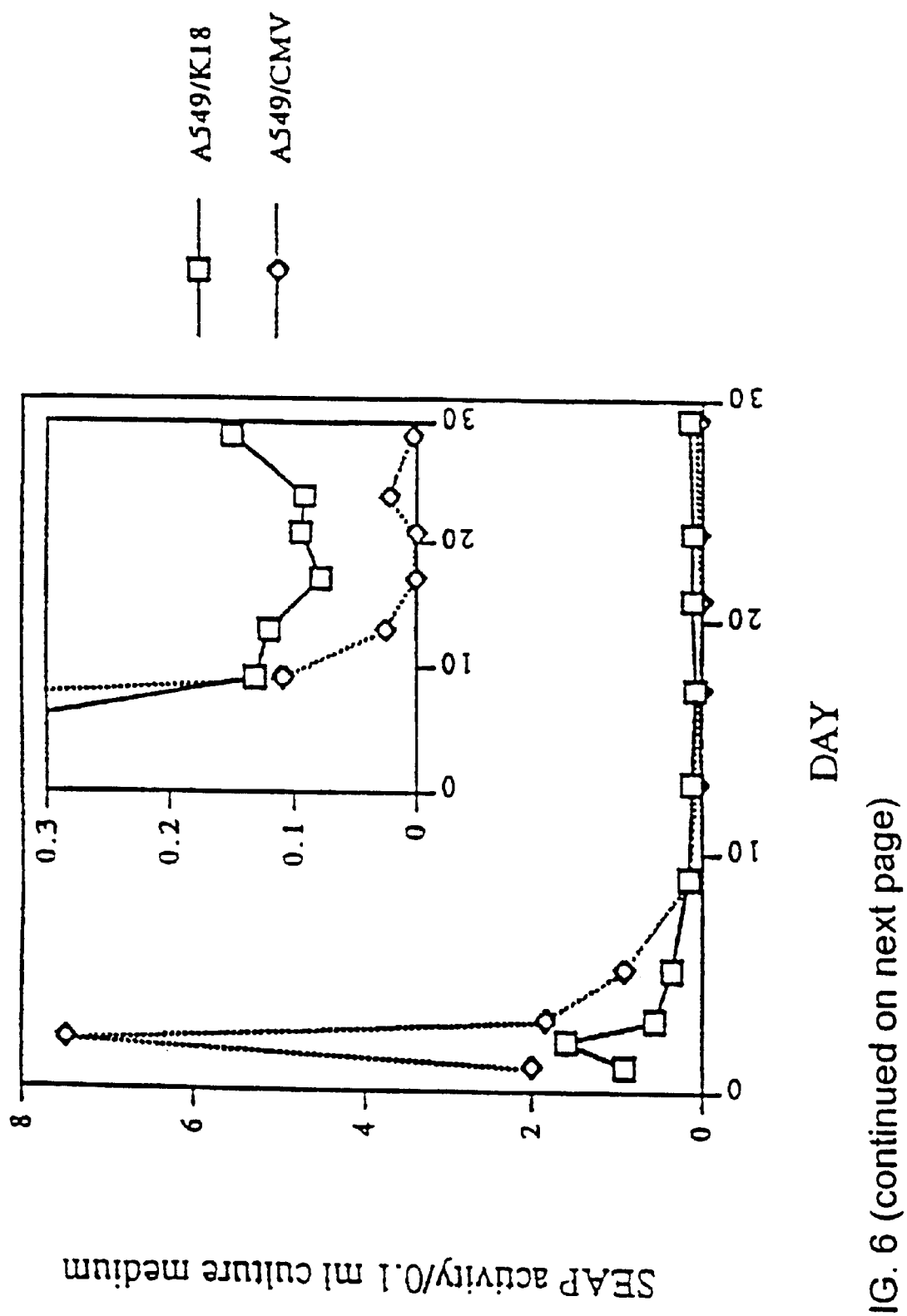
FIG. 6 (continued on next page)

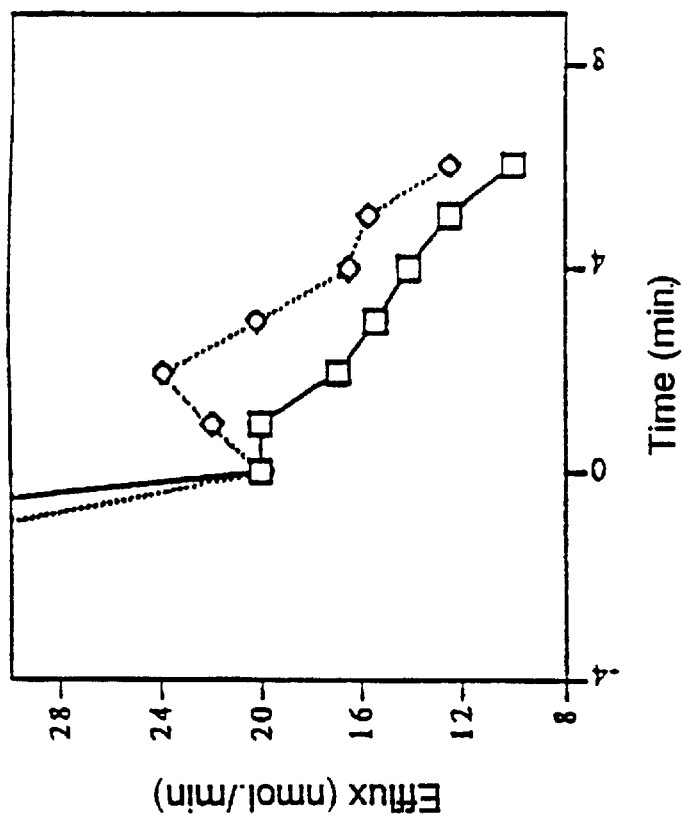
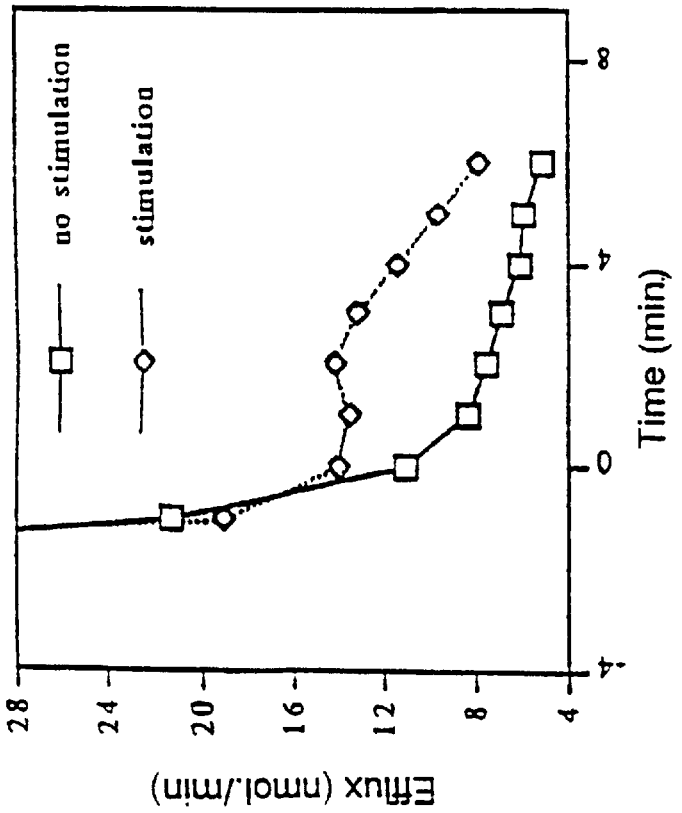
FIG. 8 (continued on next page)

AG/GUAAGG————————ACAUAAC————————CCUCUCUCUACAAUCCCCUCCAG/A
5' splice site            Branch site        Polyprimidine tract        3' splice site

FIG. 9C

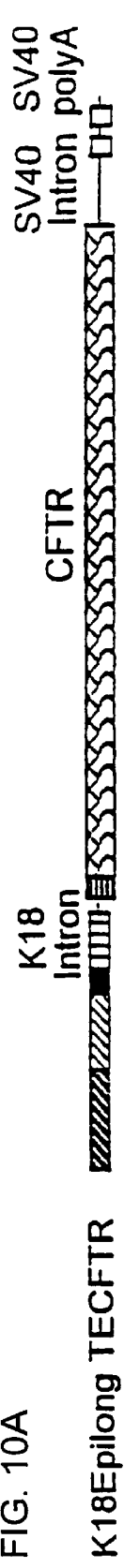
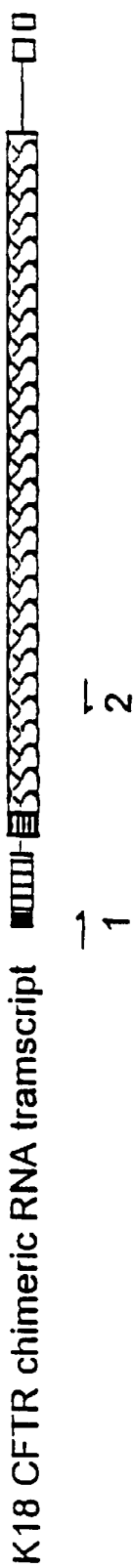
FIG. 10A
FIG. 10B
----CCTCTCTCTACAATCCCTCCAG/A------TTTTTTTCAG/C------TCTTTTTATATTAG/G
K18 3' splice site    CFTR 3' splice site-1    CFTR 3' splice site-2
FIG. 10C
----CCTCTCTCTTTTTTTCAG/G------TTTTTTTCAG/C------TCTTTTTATATTGGG

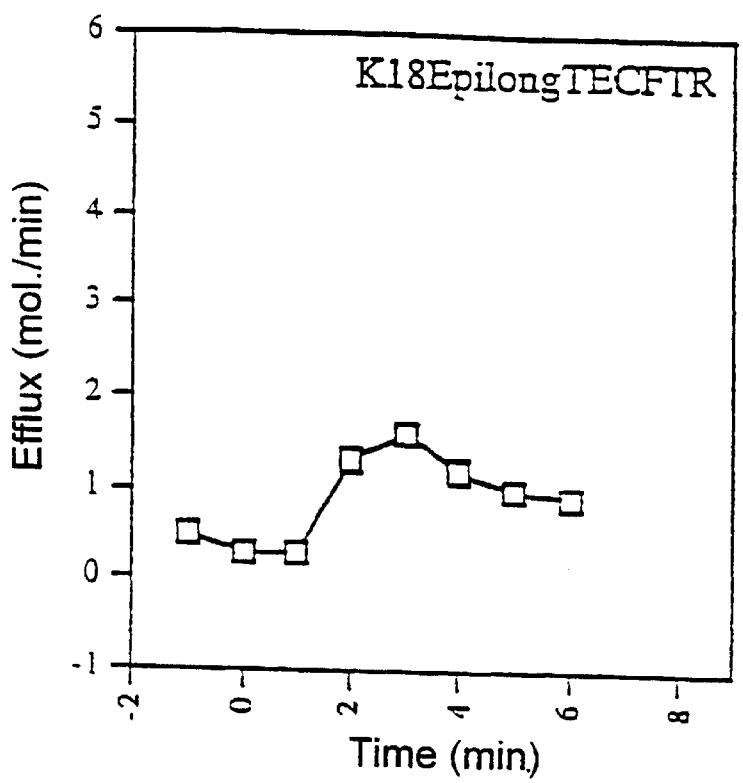
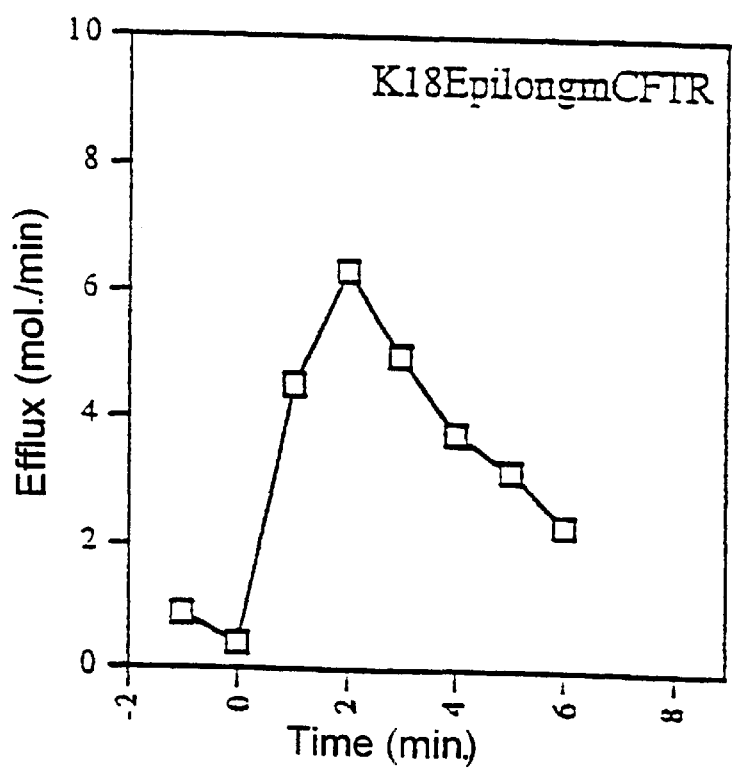
FIG. 12 (continued on next page)

12.5 days   13.5 days   14.5 days   17.5 days

DNA sequence    12143 b.p.    ggtaccaataac...cataacccggga    circular

| Nucleotide Numbers | Sequence Description |
|---|---|
| 1 (Kpn I) – 2565 (Mlu I) | K18 5' enhancer and promoter |
| 2565 (Mlu I) – 3315 | K18 intron 1 |
| 3315 – 3354 (Nco I) | Translational enhancer (TE) |
| 3354 (Nco I) – 7955 (Pst I) | CFTR (Translation starts with ATG in Nco I) |
| 7955 – 9283 (Sal I) | SV40 small + Ag intron + SV40 early poly A signal |
| 9283 (Sal I) – 12143 | pSEAP (Tropix) backbone |

20 A

```
GGTACCAATAACAGTAAAAGGCAGTACATAGCTTGTTGACTCCACATACTTTATTATAAAATACTG
CCCAACTTGACAGTTCTGGAATCCAGTGGGGGAATATAAAGGTGAAAGCAGGAGAGACCCCTCTGA
CTGGAACCTCTTACCTCCCAGAAGCCTTGTATGCAAAACCAGTGGGCATTCATTTGTATGTTATTT
TGCATCCCGTTTGCCTCCCAGCCTTCAGCAGGCCCCGACCCTCCCCTGGCCAGCTTCCACCCTGAC
TGCCCCCTGGCTGGCTCCCATTGAGCACTGTGGGCTCTCCCCACCATTAGGTGACAGATCAGGAAC
AATCCAGGCTCAGGCTCTTTATCTGTGCTCTGCCTCCCACCTGGCAGGTCCACTGGCCAGGCTTTT
CCAGGGTCCCTTCTCTCCCAGGTCTGCCCTACTATTTGTCCTCCCCTTCCCCCTCAGCTGGTAGCT
CGATAAGAATCAATAGGTCCACTCCAGAGCAAAGAACACAGCCAAATGTGTCATACCAGGCCCTGC
CAGAAAAACGAGCTGCTGGAGCTGACAAACTTGAAGGCCAAACACCTAAGGTTCCCCCAACACTT
CATTCAGCAGGGATGGTCATTCAGCTTCAGGGGCAGGCAGCATGAAAGCCTCCCTACCTCCATCC
TTCTCACACAGAGGCTGGGGAGAGCATCTTGGAGGATGCAGTCCCCTGGGGCCAGGCTTCTAATCC
AGACAGCCCTTACAAGGGGGGACAGGGGAAGGACTGGCTTGGAGAAAAGTCCTAGAAAAGAGGGGA
GGGGCACTGGCCACCAGGGCTGGGTCGCTGCTATGATGGTCCTAGGAGTGCCTGCCTGTCCTCTCA
GGCCCCATGCGATGTAGGACACATTACTTTTATTTATTTATTTATTTTGAGTCAGAGTTTCG
CTCTGGTTGCCCAGGCTGGAGCGCGACGGCACGATCTTGGCTCACTGCAACCTCTGCCTCCTGGGT
TCAAGCGATTCTCCTGCCTCAGCCTCCTGAGTAGCTGGGATTACAGGCACACACTGTGCTGGTTAA
TTTTTGTATTTTTAGTAGAGAAGGGGTGTCACCATGTTGGTCAGGCTGGTCTCAAATTTTTTTTTT
TTTTTTTTTTTTTTTTGAGACAGAGTCTTGCTCTGTTGTCTAGGCTGGAGTGCAGTGGCATCGAA
CTCTTGACCTCAAGTGATCCACCCGCCTCGGCCTCCCAAAGTGCTTGGATTACAGGCATGAGCCAC
TGTGCCCGGCGATGTGGGACACATTATCATCTCTGTGAGAGATTTTTGGTCTCTTTTGTCACCGCC
CTTCTCTCCAGCTCCTAGAACTGGGCCTGGCTCACAGTAGGTGCTGAATGCATACTGGTTGAATT
GTAAATGCTCAGGATTTGTTTAATTAAGGATGCAGGAAAGGTGATATACCGGTGTGCAGAAGTCAG
GATGCATTCCCTGTCCAAATCACAGTGTTCCACTGAGGCAAGGCCCTTGGGAGTGAGGTCGGGAGA
GGGGAGGGTGGTGGAGGGGGCTCAGAGACTGGGTTTGTTTTGGGGAGTCTGCACCTATTTGCTGAG
TGAATGTATGTGTGTGTGCATTTGAGAGCACACCTCTGTATGATTCGGGTGTGAGTGTGTGTGAGG
AAACGTGGGCAGGCGAGGAGTGTTTGGGAGCCAGGTGCAGCTGGGGTGTGAGTGTGTAAGCAAGCA
GCTATGAGGCTGGGCATTGCTTCTCCTCCTCTTCTCCAGCTCCCAGCCTTTCTTCCCCGGGACTCC
TGGGGCTCCAGGATGCCCCAAGATCCCCTCCACAAGTGGATAATTTGGGCTGCAGGTTAAGGACA
GCTAGAGGGACTCACAGGCCATTCCACCCGCACACCACCAGACCCCCAAATTTCTTTTTTCTTTTT
TTTTTGAGACAGAGTCTCACTCTGTCGCCAGGCTGCAGTGGCGCGATCTCGGCTCACTGCAACCTC
CGCCTCCCAGGTTCAAGCGATTCCCCTTCCTCAGCCTCCCAAGTAGCTGAGACTACAGGCGTGCAC
CATCACGTCCGGCTAATTTTTTGTATTTTAGTAGAGAGGGGTTTCACCATGTTGGCTAGGATGGTC
TCGATCTCCTGACCTCGTGATCCGCCCACCTAGGCCTCCCAAAGTGCTGAGATTACAGGCGTGAGC
CACTGCGCCCGGTCAAGACTCCCAAATTTCAAACTCGCCAGCACCTCCTCCACCTGGGGAGAAGA
GCATAATAACGTCATTTCCTGCCCTGAAAGCAGCCTCGAGGGCCAACAACACCTGCTGTCCGTGTC
CATGCCCGGTTGGCCACCCCGTTTCTGGGGGGTGAGCGGGGCTTGGCAGGGCTGCGCGGAGGGCGC
GGGGGTGGGGCCCGGGGCGGAGCGGCCCGGGGCGGAGGGCGCGGGCTCCGAGCCGTCCACCTGTGG
CTCCGGCTTCCGAAGCGGCTCCGGGGCGGGGCGGGGCCTCACTCTGCGATATAACTCGGGTCGCG
CGGCTCGCGCAGGCCGCCACCGTCGTCCGCAAAGCCTGAGTCCTGTCCTTTCTCACGCGTCAGG
TAAGGGGTAGGAGGGACCTCAACTCCCAGCCTTGTCTGACCCTCCAATTATACACTCCTTTGCCTC
TTTCCGTCATTCCATAACCACCCCAACCCCTACTCCACCGGGAGGGGGTTGGGCATACCTGGATTT
CCATCCGCGCACCTAGCCACAGGGTCCCTAAGAGCAGCAGCAGCTAGGCATGGGAGGGCTCTTTCC
CAGGAGAGAGGGGGAAGGGGACAGGGTTGAGAGCTTTACAGAGGAAGTGGACAGCATGGAGGGAGG
TAAGGAAAGGCCTGTAAAGAGGAGGAGACACTGGCTCTGGCGGAATGGGGACTATTGGAGGGTTAA
GCGGATGTGGCTAAGGCTGAGTCATCTAGGAGTAAACAAGAGGCCTTCCTTTGGGAGGAGCCAATC
CAGGGTGTAGGGGCCCAGAGTGACCAGGTGCACTAGGGAAAAAATGCCAGGAGAGGGCCAGGAAG
AGGACTTGTTAGTAGCGACTCACTTCTGGGCAGGCAGGCCAGCCAGCTAGCCAGCCTGCTGAGGCT
TCCCAAGAGGGCAGAGTGCTGGGATCTGGGAATCCAGGAAAGGAGGGAATGGGGTGGGCTAGAT
GAAAAGGGATAGGTGTCCAGGGAGAGCCTCTGGCTATTCCTGGGACCAGGAAGTTTTCACTAGGAT
```

Figure 20 (continued on next page)

```
ACATAACACTTTTTACACACTCACCCCACCCATCCCTGGCTTTCTATTCATGGAACAACCTCTCTC
TTTTTTTTTTCAGGTCTGTTTTTATTTTTAATTTTCTTTCAAATACTTCCACCATGGCCAAGATC
CCTCCTAAGAAGAAGCGCAAAGTCGAGGATCCCGTCGTTTTACAACGTCGTGACTGGGAAAACCCT
GGCGTTACCCAACTTAATCGCCTTGCAGCACATCCCCCTTTCGCCAGCTGGCGTAATAGCGAAGAG
GCCCGCACCGATCGCCCTTCCCAACAGTTGCGCAGCCTGAATGGCGAATGGCGCTTTGCCTGGTTT
CCGGCACCAGAAGCGGTGCCGGAAAGCTGGCTGGAGTGCGATCTTCCTGAGGCCGATACTGTCGTC
GTCCCCTCAAACTGGCAGATGCACGGTTACGATGCGCCCATCTACACCAACGTAACCTATCCCATT
ACGGTCAATCCGCCGTTTGTTCCCACGGAGAATCCGACGGGTTGTTACTCGCTCACATTTAATGTT
GATGAAAGCTGGCTACAGGAAGGCCAGACGCGAATTATTTTTGATGGCGTTAACTCGGCGTTTCAT
CTGTGGTGCAACGGGCGCTGGGTCGGTTACGGCCAGGACAGTCGTTTGCCGTCTGAATTTGACCTG
AGCGCATTTTTACGCGCCGGAGAAAACCGCCTCGCGGTGATGGTGCTGCGTTGGAGTGACGGCAGT
TATCTGGAAGATCAGGATATGTGGCGGATGAGCGGCATTTTCCGTGACGTCTCGTTGCTGCATAAA
CCGACTACACAAATCAGCGATTTCCATGTTGCCACTCGCTTTAATGATGATTTCAGCCGCGCTGTA
CTGGAGGCTGAAGTTCAGATGTGCGGCGAGTTGCGTGACTACCTACGGGTAACAGTTTCTTTATGG
CAGGGTGAAACGCAGGTCGCCAGCGGCACCGCGCCTTTCGGCGGTGAAATTATCGATGAGCGTGGT
GGTTATGCCGATCGCGTCACACTACGTCTGAACGTCGAAAACCCGAAACTGTGGAGCGCCGAAATC
CCGAATCTCTATCGTGCGGTGGTTGAACTGCACACCGCCGACGGCACGCTGATTGAAGCAGAAGCC
TGCGATGTCGGTTTCCGCGAGGTGCGGATTGAAAATGGTCTGCTGCTGCTGAACGGCAAGCCGTTG
CTGATTCGAGGCGTTAACCGTCACGAGCATCATCCTCTGCATGGTCAGGTCATGGATGAGCAGACG
ATGGTGCAGGATATCCTGCTGATGAAGCAGAACAACTTTAACGCCGTGCGCTGTTCGCATTATCCG
AACCATCCGCTGTGGTACACGCTGTGCGACCGCTACGGCCTGTATGTGGTGGATGAAGCCAATATT
GAAACCCACGGCATGGTGCCAATGAATCGTCTGACCGATGATCCGCGCTGGCTACCGGCGATGAGC
GAACGCGTAACGCGAATGGTGCAGCGCGATCGTAATCACCCGAGTGTGATCATCTGGTCGCTGGGG
AATGAATCAGGCCACGGCGCTAATCACGACGCGCTGTATCGCTGGATCAAATCTGTCGATCCTTCC
CGCCCGGTGCAGTATGAAGGCGGCGGAGCCGACACCACGGCCACCGATATTATTTGCCCGATGTAC
GCGCGCGTGGATGAAGACCAGCCCTTCCCGGCTGTGCCGAAATGGTCCATCAAAAAATGGCTTTCG
CTACCTGGAGAGACGCGCCCGCTGATCCTTTGCGAATACGCCCACGCGATGGGTAACAGTCTTGGC
GGTTTCGCTAAATACTGGCAGGCGTTTCGTCAGTATCCCCGTTTACAGGGCGGCTTCGTCTGGGAC
TGGGTGGATCAGTCGCTGATTAAATATGATGAAAACGGCAACCCGTGGTCGGCTTACGGCGGTGAT
TTTGGCGATACGCCGAACGATCGCCAGTTCTGTATGAACGGTCTGGTCTTTGCCGACCGCACGCCG
CATCCAGCGCTGACGGAAGCAAAACACCAGCAGCAGTTTTTCCAGTTCCGTTTATCCGGGCAAACC
ATCGAAGTGACCAGCGAATACCTGTTCCGTCATAGCGATAACGAGCTCCTGCACTGGATGGTGGCG
CTGGATGGTAAGCCGCTGGCAAGCGGTGAAGTGCCTCTGGATGTCGCTCCACAAGGTAAACAGTTG
ATTGAACTGCCTGAACTACCGCAGCCGGAGAGCGCCGGGCAACTCTGGCTCACAGTACGCGTAGTG
CAACCGAACGCGACCGCATGGTCAGAAGCCGGGCACATCAGCGCCTGGCAGCAGTGGCGTCTGGCG
GAAAACCTCAGTGTGACGCTCCCCGCCGCGTCCCACGCCATCCCGCATCTGACCACCAGCGAAATG
GATTTTTGCATCGAGCTGGGTAATAAGCGTTGGCAATTTAACCGCCAGTCAGGCTTTCTTTCACAG
ATGTGGATTGGCGATAAAAAACAACTGCTGACGCCGCTGCGCGATCAGTTCACCCGTGCACCGCTG
GATAACGACATTGGCGTAAGTGAAGCGACCCGCATTGACCCTAACGCCTGGGTCAACGCTGGAAG
GCGGCGGGCCATTACCAGGCCGAAGCAGCGTTGTTGCAGTGCACGGCAGATACACTTGCTGATGCG
GTGCTGATTACGACCGCTCACGCGTGGCAGCATCAGGGGAAAACCTTATTTATCAGCCGGAAAACC
TACCGGATTGATGGTAGTGGTCAAATGGCGATTACCGTTGATGTTGAAGTGGCGAGCGATACACCG
CATCCGGCGCGGATTGGCCTGAACTGCCAGCTGGCGCAGGTAGCAGAGCGGGTAAACTGGCTCGGA
TTAGGGCCGCAAGAAAACTATCCCGACCGCCTTACTGCCGCCTGTTTTGACCGCTGGGATCTGCCA
TTGTCAGACATGTATACCCCGTACGTCTTCCCGAGCGAAAACGGTCTGCGCTGCGGGACGCGCGAA
TTGAATTATGGCCCACACCAGTGGCGCGGCGACTTCCAGTTCAACATCAGCCGCTACAGTCAACAG
CAACTGATGGAAACCAGCCATCGCCATCTGCTGCACGCGGAAGAAGGCACATGGCTGAATATCGAC
GGTTTCCATATGGGGATTGGTGGCGACGACTCCTGGAGCCCGTCAGTATCGGCGGAATTCCAGCTG
AGCGCCGGTCGCTACCATTACCAGTTGGTCTGGTGTCAAAATATCTTTGTGAAGGAACCTTACTT
CTGTGGTGTGACATAATTGGACAAACTACCTACAGAGATTTAAAGCTCTAAGGTAAATATAAAATT
TTTAAGTGTATAATGTGTTAAACTACTGATTCTAATTGTTTGTGTATTTTAGATTCCAACCTATGG
AACTGATGAATGGGAGCAGTGGTGGAATGCCTTTAATGAGGAAAACCTGTTTTGCTCAGAAGAAAT
GCGATCTAGTGATGATGAGGCTACTGCTGACTCTCAACATTCTACTCCTCCAAAAAAGAAGAGAAA
GGTAGAAGACCCCAAGGACTTTCCTTCAGAATTGCTAAGTTTTTTGAGTCATGCTGTGTTTAGTAA
```

Figure 20 (continued on next page)

```
TAGAACTCTTGCTTGCTTTGCTATTTACACCACAAAGGAAAAAGCTGCACTGCTATACAAGAAAAT
TATGGAAAAATATTCTGTAACCTTTATAAGTAGGCATAACAGTTATAATCATAACATACTGTTTTT
TCTTACTCCACACAGGCATAGAGTGTCTGCTATTAATAACTATGCTCAAAAATTGTGTACCTTTAG
CTTTTTAATTTGTAAAGGGGTTAATAAGGAATATTTGATGTATAGTGCCTTGACTAGAGATCATAA
TCAGCCATACCACATTTGTAGAGGTTTTACTTGCTTTAAAAAACCTCCCACACCTCCCCCTGAACC
TGAAACATAAAATGAATGCAATTGTTGTTGTTAACTTGTTTATTGCAGCTTATAATGGTTACAAAT
AAAGCAATAGCATCACAAATTTCACAAATAAAGCATTTTTTTCACTGCATTCTAGTTGTGGTTTGT
CCAAACTCATCAATGTATCTTATCATGTCTGGATCCCCAGGAAGCTCCTCTGTGTCCTCATAAACC
CTAACCTCCTCTACTTGAGAGGACATTCCAATCATAGGCTGCCCATCCACCCTCTGTGTCCTCCTG
TTAATTAGGTCACTTAACAAAAGGAAATTGGGTAGGGTTTTTCACAGACCGCTTTCTAAGGGTA
ATTTTAAAATATCTGGGAAGTCCCTTCCACTGCTGTGTTCCAGAAGTGTTGGTAAACAGCCCACAA
ATGTCAACAGCAGAAACATACAAGCTGTCAGCTTTGCACAAGGGCCCGGTACCCGGGGATCCTCTA
GAACTAGTGGATCCCCCGGGCTGCAGGAATTCGATATCAAGCTTATCGATACCGTCGACCGATGCC
CTTGAGAGCCTTCAACCCAGTCAGCTCCTTCCGGTGGGCGCGGGGCATGACTATCGTCGCCGCACT
TATGACTGTCTTCTTTATCATGCAACTCGTAGGACAGGTGCCGGCAGCGCTCTTCCGCTTCCTCGC
TCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGCAA
TGATACCGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCAC
CTGACGCGCCCTGTAGCGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGTGCTTTACGGCACC
TCGACCCCAAAAAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACTGGAACAACAC
TCAACCCTATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTTCCC
ATTCGCCATTCAGGCTACGCAACTGTTGGGAAGGGCGATCGGTGCGGGCCTCTTCGCTATTACGCC
AGCCCAAGCTACCATGATAAGTAAGTAATATTAAGGTACGTGGAGGTTTTACTTGCTTTAAAAAAC
CTCCCACACCTCCCCCTGAACCTGAAACATAAAATGAATGCAATTGTTGTTGTTAACTTGTTTATT
```

Figure 20 (continued on next page)

```
GCAGCTTATAATGGTTACAAATAAAGCAATAGCATCACAAATTTCACAAATAAAGCATTTTTTTCA
CTGCATTCTAGTTGTGGTTTGTCCAAACTCATCAATGTATCTTATGGTACTGTAACTGAGCTAACA
TAACCCGGGA
```

20 B

20 C

| Nucleotide Positions | Features |
|---|---|
| 1-2565 | K18 5'Enhancer and promoter |
| 2566-3315 | K18 Intron 1 |
| 3316-3354 | Translational Enhancer (TE) |
| 3355-6446 | LacZ |
| 6447-7644 | SV40 small T antigen and polyA signal |
| 7645-10504 | pSEAP (Tropix) backbone |

```
                           SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
           (A) LENGTH: 12143 base pairs
           (B) TYPE: nucleic acid
           (C) STRANDEDNESS: double
           (D) TOPOLOGY: circular (ii) MOLECULE TYPE: other nucleic acid
           (A) DESCRIPTION: /desc = "Mixture of genomic DNA, (ix) FEATURE:
           (A) NAME/KEY: enhancer
           (B) LOCATION:8..2570
           (C) IDENTIFICATION METHOD:
           (D) OTHER INFORMATION:/standard_name= "K18
                Enhancer/Promoter"
                /note= "DNA fragment was obtained by PCR-cloning and
                minor modifications were introduced for the purpose
                of PCR."

(ix) FEATURE:
           (A) NAME/KEY: intron
           (B) LOCATION:2571..3318
           (C) IDENTIFICATION METHOD:
           (D) OTHER INFORMATION:/standard_name= "K18 intron 1"
                /note= "DNA fragment was obtained by PCR-cloning and
                modifications were introduced to improve the splicing
                efficiency."

(ix) FEATURE:
           (A) NAME/KEY: enhancer
           (B) LOCATION:3319..3354
           (C) IDENTIFICATION METHOD:
           (D) OTHER INFORMATION:/standard_name= "Alfalfa mosaic
                virus translational enhancer"
                /note= "Fragment was synthesized chemically."

(ix) FEATURE:
           (A) NAME/KEY: misc_feature
           (B) LOCATION:3355..7948
           (C) IDENTIFICATION METHOD:
           (D) OTHER INFORMATION:/standard_name= "CFTR cDNA"

(ix) FEATURE:
           (A) NAME/KEY: misc_feature
           (B) LOCATION:7949..7984
           (C) IDENTIFICATION METHOD:
           (D) OTHER INFORMATION:/standard_name= "pBluescript II
                KS(+) multiple cloning site"

(ix) FEATURE:
           (A) NAME/KEY: intron
           (B) LOCATION:8507..8572
           (C) IDENTIFICATION METHOD:
           (D) OTHER INFORMATION:/standard_name= "SV40 small t
                antigen intron"
```

(ix) FEATURE:
        (A) NAME/KEY: polyA_signal
        (B) LOCATION:9178..9212
        (C) IDENTIFICATION METHOD:
        (D) OTHER INFORMATION:/standard_name= "SV40
            polyadenylation signal"

(ix) FEATURE:
        (A) NAME/KEY: polyA_signal
        (B) LOCATION:12021..12055
        (C) IDENTIFICATION METHOD:
        (D) OTHER INFORMATION:/standard_name= "SV40
            polyadenylation signal"

(ix) FEATURE:
        (A) NAME/KEY: rep_origin
        (B) LOCATION:9562..10205
        (C) IDENTIFICATION METHOD:
        (D) OTHER INFORMATION:/standard_name= "pUC origin of
            replication"

(ix) FEATURE:
        (A) NAME/KEY: misc_feature
        (B) LOCATION:11283..11353
        (C) IDENTIFICATION METHOD:
        (D) OTHER INFORMATION:/standard_name= "Ampicillin
            resistance gene"

(ix) FEATURE:
        (A) NAME/KEY: misc_feature
        (B) LOCATION:11345..11800
        (C) IDENTIFICATION METHOD:
        (D) OTHER INFORMATION:/standard_name= "f1 single strand
            DNA origin"

(xi) SEQUENCE DESCRIPTION: SEQ ID NO: 1:

```
GGTACCAATA ACAGTAAAAG GCAGTACATA GCTTGTTGAC TCCACATACT TTATTATAAA     60

ATACTGCCCA ACTTGACAGT TCTGGAATCC AGTGGGGGAA TATAAAGGTG AAAGCAGGAG    120

AGACCCCTCT GACTGGAACC TCTTACCTCC CAGAAGCCTT GTATGCAAAA CCAGTGGGCA    180

TTCATTTGTA TGTTATTTTG CATCCCGTTT GCCTCCCAGC CTTCAGCAGG CCCCGACCCT    240

CCCCTGGCCA GCTTCCACCC TGACTGCCCC CTGGCTGGCT CCCATTGAGC ACTGTGGGCT    300

CTCCCCACCA TTAGGTGACA GATCAGGAAC AATCCAGGCT CAGGCTCTTT ATCTGTGCTC    360

TGCCTCCCAC CTGGCAGGTC CACTGGCCAG GCTTTTCCAG GGTCCCTTCT CTCCCAGGTC    420

TGCCCTACTA TTTGTCCTCC CCTTCCCCCT CAGCTGGTAG CTCGATAAGA ATCAATAGGT    480

CCACTCCAGA GCAAAGAACA CAGCCAAATG TGTCATACCA GGCCCTGCCA GAAAAACGAG    540

CTGCTGGAGC TGACAAACTT GAAGGCCAAA CACCTAAGGT TCCCCCCAAC ACTTCATTCA    600

GCAGGGATGG TCATTCAGCT TCAGGGGGCA GGCAGCATGA AAGCCTCCCT ACCTCCATCC    660

TTCTCACACA GAGGCTGGGG AGAGCATCTT GGAGGATGCA GTCCCCTGGG GCCAGGCTTC    720

TAATCCAGAC AGCCCTTACA AGGGGGGACA GGGGAAGGAC TGGCTTGGAG AAAAGTCCTA    780

GAAAAGAGGG GAGGGGCACT GGCCACCAGG GCTGGGTCGC TGCTATGATG GTCCTAGGAG    840

TGCCTGCCTG TCCTCTCAGG CCCCATGCGA TGTAGGACAC ATTACTTTTA TTTATTTATT    900

TATTTATTTT GAGTCAGAGT TTCGCTCTGG TTGCCCAGGC TGGAGCGCGA CGGCACGATC    960

TTGGCTCACT GCAACCTCTG CCTCCTGGGT TCAAGCGATT CTCCTGCCTC AGCCTCCTGA   1020

GTAGCTGGGA TTACAGGCAC ACACTGTGCT GGTTAATTTT TGTATTTTTA GTAGAGAAGG   1080

GGTGTCACCA TGTTGGTCAG GCTGGTCTCA AATTTTTTTT TTTTTTTTTT TTTTTTTTG   1140

AGACAGAGTC TTGCTCTGTT GTCTAGGCTG GAGTGCAGTG GCATCGAACT CTTGACCTCA   1200

AGTGATCCAC CCGCCTCGGC CTCCCAAAGT GCTTGGATTA CAGGCATGAG CCACTGTGCC   1260
```

```
CGGCGATGTG GGACACATTA TCATCTCTGT GAGAGATTTT TGGTCTCTTT TGTCACCGCC    1320

CTTCTCTCCC AGCTCCTAGA ACTGGGCCTG GCTCACAGTA GGTGCTGAAT GCATACTGGT    1380

TGAATTGTAA ATGCTCAGGA TTTGTTTAAT TAAGGATGCA GGAAAGGTGA TATACCGGTG    1440

TGCAGAAGTC AGGATGCATT CCCTGTCCAA ATCACAGTGT TCCACTGAGG CAAGGCCCTT    1500

GGGAGTGAGG TCGGGAGAGG GGAGGGTGGT GGAGGGGGCT CAGAGACTGG GTTTGTTTTG    1560

GGGAGTCTGC ACCTATTTGC TGAGTGAATG TATGTGTGTG TGCATTTGAG AGCACACCTC    1620

TGTATGATTC GGGTGTGAGT GTGTGTGAGG AAACGTGGGC AGGCGAGGAG TGTTTGGGAG    1680

CCAGGTGCAG CTGGGGTGTG AGTGTGTAAG CAAGCAGCTA TGAGGCTGGG CATTGCTTCT    1740

CCTCCTCTTC TCCAGCTCCC AGCCTTTCTT CCCCGGGACT CCTGGGGCTC AGGATGCCC     1800

CCAAGATCCC CTCCACAAGT GGATAATTTG GCTGCAGGT TAAGGACAGC TAGAGGGACT     1860

CACAGGCCAT TCCACCCGCA CACCACCAGA CCCCCAAATT TCTTTTTTCT TTTTTTTTG     1920

AGACAGAGTC TCACTCTGTC GCCAGGCTGC AGTGGCGCGA TCTCGGCTCA CTGCAACCTC    1980

CGCCTCCCAG GTTCAAGCGA TTCCCCTTCC TCAGCCTCCC AAGTAGCTGA GACTACAGGC    2040

GTGCACCATC ACGTCCGGCT AATTTTTTGT ATTTTAGTAG AGAGGGGTTT CACCATGTTG    2100

GCTAGGATGG TCTCGATCTC CTGACCTCGT GATCCGCCCA CCTAGGCCTC CCAAAGTGCT    2160

GAGATTACAG GCGTGAGCCA CTGCGCCCGG TCAAGACTCC CAAATTTCAA ACTCGCCAGC    2220

ACCTCCTCCA CCTGGGGGAG AAGAGCATAA TAACGTCATT TCCTGCCCTG AAAGCAGCCT    2280

CGAGGGCCAA CAACACCTGC TGTCCGTGTC CATGCCCGGT TGGCCACCCC GTTTCTGGGG    2340

GGTGAGCGGG GCTTGGCAGG GCTGCGCGGA GGGCGCGGGG GTGGGGCCCG GGCGGAGCG    2400

GCCCGGGGCG GAGGGCGCGG GCTCCGAGCC GTCCACCTGT GGCTCCGGCT TCCGAAGCGG    2460

CTCCGGGGCG GGGGCGGGGC CTCACTCTGC GATATAACTC GGGTCGCGCG GCTCGCGCAG    2520

GCCGCCACCG TCGTCCGCAA AGCCTGAGTC CTGTCCTTTC TCTCACGCGT CAGGTAAGGG    2580

GTAGGAGGGA CCTCAACTCC CAGCCTTGTC TGACCCTCCA ATTATACACT CCTTTGCCTC    2640

TTTCCGTCAT TCCATAACCA CCCCAACCCC TACTCCACCG GGAGGGGGTT GGGCATACCT    2700

GGATTTCCAT CCGCGCACCT AGCCACAGGG TCCCTAAGAG CAGCAGCAGC TAGGCATGGG    2760

AGGGCTCTTT CCCAGGAGAG AGGGGGAAGG GGACAGGGTT GAGAGCTTTA CAGAGGAAGT    2820

GGACAGCATG GAGGGAGGTA AGGAAAGGCC TGTAAAGAGG AGGAGACACT GGCTCTGGCG    2880

GAATGGGGAC TATTGGAGGG TTAAGCGGAT GTGGCTAAGG CTGAGTCATC TAGGAGTAAA    2940

CAAGAGGCCT TCCTTTGGGA GGAGCCAATC CAGGGTGTAG GGGGCCCAGA GTGACCAGGT    3000

GCACTAGGGA AAAAATGCCA GGAGAGGGCC AGGAAGAGGA CTTGTTAGTA GCGACTCACT    3060

TCTGGGCAGG CAGGCCAGCC AGCTAGCCAG CCTGCTGAGG CTTCCCAAGA GGGGCAGAGT    3120

GCTGGGATCT GGGAATCCAG GAAAGGAGGG AATGGGTGG GGCTAGATGA AAAGGGATAG     3180

GTGTCCAGGG AGAGCCTCTG GCTATTCCTG GGACCAGGAA GTTTTCACTA GGATACATAA    3240

CACTTTTTAC ACACTCACCC CACCCATCCC TGGCTTTCTA TTCATGGAAC AACCTCTCTC    3300

TTTTTTTTTT TCAGGTCTGT TTTTATTTTT AATTTTCTTT CAAATACTTC CACCATGGAG    3360

AGGTCGCCTC TGGAAAAGGC CAGCGTTGTC TCCAAACTTT TTTTCAGCTG GACCAGACCA    3420

ATTTTGAGGA AAGGATACAG ACAGCGCCTG GAATTGTCAG ACATATACCA AATCCCTTCT    3480

GTTGATTCTG CTGACAATCT ATCTGAAAAA TTGGAAAGAG AATGGGATAG AGAGCTGGCT    3540

TCAAAGAAAA ATCCTAAACT CATTAATGCC CTTCGGCGAT GTTTTTTCTG GAGATTTATG    3600
```

```
TTCTATGGAA TCTTTTTATA TTTGGGGGAA GTCACCAAAG CAGTACAGCC TCTCTTACTG    3660

GGAAGAATCA TAGCTTCCTA TGACCCGGAT AACAAGGAGG AACGCTCTAT CGCGATTTAT    3720

CTAGGCATAG GCTTATGCCT TCTCTTTATT GTGAGGACAC TGCTCCTACA CCCAGCCATT    3780

TTTGGCCTTC ATCACATTGG AATGCAGATG AGAATAGCTA TGTTTAGTTT GATTTATAAG    3840

AAGACTTTAA AGCTGTCAAG CCGTGTTCTA GATAAAATAA GTATTGGACA ACTTGTTAGT    3900

CTCCTTTCCA ACAACCTGAA CAAATTTGAT GAAGGACTTG CATTGGCACA TTTCGTGTGG    3960

ATCGCTCCTT TGCAAGTGGC ACTCCTCATG GGGCTAATCT GGGAGTTGTT ACAGGCGTCT    4020

GCCTTCTGTG GACTTGGTTT CCTGATAGTC CTTGCCCTTT TCAGGCTGG GCTAGGAGAG     4080

ATGATGATGA AGTACAGAGA TCAGAGAGCT GGGAAGATCA GTGAAAGACT TGTGATTACC    4140

TCAGAAATGA TTGAAAATAT CCAATCTGTT AAGGCATACT GCTGGGAAGA AGCAATGGAA    4200

AAAATGATTG AAAACTTAAG ACAAACAGAA CTGAAACTGA CTCGGAAGGC AGCCTATGTG    4260

AGATACTTCA ATAGCTCAGC CTTCTTCTTC TCAGGGTTCT TTGTGGTGTT TTTATCTGTG    4320

CTTCCCTATG CACTAATCAA AGGAATCATC CTCCGGAAAA TATTCACCAC CATCTCATTC    4380

TGCATTGTTC TGCGCATGGC GGTCACTCGG CAATTTCCCT GGGCTGTACA AACATGGTAT    4440

GACTCTCTTG GAGCAATAAA CAAAATACAG GATTCTTAC AAAAGCAAGA ATATAAGACA     4500

TTGGAATATA ACTTAACGAC TACAGAAGTA GTGATGGAGA ATGTAACAGC CTTCTGGGAG    4560

GAGGGATTTG GGAATTATT TGAGAAAGCA AAACAAAACA ATAACAATAG AAAAACTTCT     4620

AATGGTGATG ACAGCCTCTT CTTCAGTAAT TTCTCACTTC TTGGTACTCC TGTCCTGAAA    4680

GATATTAATT TCAAGATAGA AAGAGGACAG TTGTTGGCGG TTGCTGGATC CACTGGAGCA    4740

GGCAAGACTT CACTTCTAAT GATGATTATG GGAGAACTGA AGCCTTCAGA GGGTAAAATT    4800

AAGCACAGTG GAAGAATTTC ATTCTGTTCT CAGTTTTCCT GGATTATGCC TGGCACCAAA    4860

AAAGAAAATA TCATCTTTGG TGTTTCCTAT GATGAATATA GATACAGAAG CGTCATCAAA    4920

GCATGCCAAC TAGAAGAGGA CATCTCCAAG TTTGCAGAGA AAGACAATAT AGTTCTTGGA    4980

GAAGGTGGAA TCACACTGAG TGGAGGTCAA CGAGCAAGAA TTTCTTTAGC AAGAGCAGTA    5040

TACAAAGATG CTGATTTGTA TTTATTAGAC TCTCCTTTTG GATACCTAGA TGTTTTAACA    5100

GAAAAAGAAA TATTTGAAAG CTGTGTCTGT AAACTGATGG CTAACAAAAC TAGGATTTTG    5160

GTCACTTCTA AAATGGAACA TTTAAAGAAA GCTGACAAAA TATTAATTTT GAATGAAGGT    5220

AGCAGCTATT TTTATGGGAC ATTTTCAGAA CTCCAAAATC TACAGCCAGA CTTTAGCTCA    5280

AAACTCATGG GATGTGATTC TTTCGACCAA TTTAGTGCAG AAAGAAGAAA TTCAATCCTA    5340

ACTGAGACCT TACACCGTTT CTCATTAGAA GGAGATGCTC CTGTCTCCTG GACAGAAACA    5400

AAAAAACAAT CTTTTAAACA GACTGGAGAG TTTGGGGAAA AAGGAAGAA TTCTATTCTC     5460

AATCCAATCA ACTCTATACG AAAATTTTCC ATTGTGCAAA AGACTCCCTT ACAAATGAAT    5520

GGCATCGAAG AGGATTCTGA TGAGCCTTTA GAGAGAAGGC TGTCCTTAGT ACCAGATTCT    5580

GAGCAGGGAG AGGCGATACT GCCTCGCATC AGCGTGATCA GCACTGGCCC CACGCTTCAG    5640

GCACGAAGGA GGCAGTCTGT CCTGAACCTG ATGACACACT CAGTTAACCA AGGTCAGAAC    5700

ATTCACCGAA AGACAACAGC ATCCACACGA AAAGTGTCAC TGGCCCCTCA GGCAAACTTG    5760

ACTGAACTGG ATATATATTC AAGAAGGTTA TCTCAAGAAA CTGGCTTGGA AATAAGTGAA    5820

GAAATTAACG AAGAAGACTT AAAGGAGTGC CTTTTTGATG ATATGGAGAG CATACCAGCA    5880

GTGACTACAT GGAACACATA CCTTCGATAT ATTACTGTCC ACAAGAGCTT AATTTTTGTG    5940

CTAATTTGGT GCTTAGTAAT TTTTCTGGCA GAGGTGGCTG CTTCTTTGGT TGTGCTGTGG    6000
```

```
CTCCTTGGAA ACACTCCTCT TCAAGACAAA GGGAATAGTA CTCATAGTAG AAATAACAGC    6060

TATGCAGTGA TTATCACCAG CACCAGTTCG TATTATGTGT TTTACATTTA CGTGGGAGTA    6120

GCCGACACTT TGCTTGCTAT GGGATTCTTC AGAGGTCTAC CACTGGTGCA TACTCTAATC    6180

ACAGTGTCGA AAATTTTACA CCACAAAATG TTACATTCTG TTCTTCAAGC ACCTATGTCA    6240

ACCCTCAACA CGTTGAAAGC AGGTGGGATT CTTAATAGAT TCTCCAAAGA TATAGCAATT    6300

TTGGATGACC TTCTGCCTCT TACCATATTT GACTTCATCC AGTTGTTATT AATTGTGATT    6360

GGAGCTATAG CAGTTGTCGC AGTTTTACAA CCCTACATCT TTGTTGCAAC AGTGCCAGTG    6420

ATAGTGGCTT TTATTATGTT GAGAGCATAT TTCCTCCAAA CCTCACAGCA ACTCAAACAA    6480

CTGGAATCTG AAGGCAGGAG TCCAATTTTC ACTCATCTTG TTACAAGCTT AAAAGGACTG    6540

TGGACACTTC GTGCCTTCGG ACGGCAGCCT TACTTTGAAA CTCTGTTCCA CAAAGCTCTG    6600

AATTTACATA CTGCCAACTG GTTCTTGTAC CTGTCAACAC TGCGCTGGTT CCAAATGAGA    6660

ATAGAAATGA TTTTTGTCAT CTTCTTCATT GCTGTTACCT TCATTTCCAT TTTAACAACA    6720

GGAGAAGGAG AAGGAAGAGT TGGTATTATC CTGACTTTAG CCATGAATAT CATGAGTACA    6780

TTGCAGTGGG CTGTAAACTC CAGCATAGAT GTGGATAGCT TGATGCGATC TGTGAGCCGA    6840

GTCTTTAAGT TCATTGACAT GCCAACAGAA GGTAAACCTA CCAAGTCAAC CAAACCATAC    6900

AAGAATGGCC AACTCTCGAA AGTTATGATT ATTGAGAATT CACACGTGAA GAAAGATGAC    6960

ATCTGGCCCT CAGGGGGCCA AATGACTGTC AAAGATCTCA CAGCAAAATA CACAGAAGGT    7020

GGAAATGCCA TATTAGAGAA CATTTCCTTC TCAATAAGTC CTGGCCAGAG GGTGGGCCTC    7080

TTGGGAAGAA CTGGATCAGG GAAGAGTACT TTGTTATCAG CTTTTTTGAG ACTACTGAAC    7140

ACTGAAGGAG AAATCCAGAT CGATGGTGTG TCTTGGGATT CAATAACTTT GCAACAGTGG    7200

AGGAAAGCCT TTGGAGTGAT ACCACAGAAA GTATTTATTT TTTCTGGAAC ATTTAGAAAA    7260

AACTTGGATC CCTATGAACA GTGGAGTGAT CAAGAAATAT GGAAAGTTGC AGATGAGGTT    7320

GGGCTCAGAT CTGTGATAGA ACAGTTTCCT GGGAAGCTTG ACTTTGTCCT TGTGGATGGG    7380

GGCTGTGTCC TAAGCCATGG CCACAAGCAG TTGATGTGCT TGGCTAGATC TGTTCTCAGT    7440

AAGGCGAAGA TCTTGCTGCT TGATGAACCC AGTGCTCATT TGGATCCAGT AACATACCAA    7500

ATAATTAGAA GAACTCTAAA ACAAGCATTT GCTGATTGCA CAGTAATTCT CTGTGAACAC    7560

AGGATAGAAG CAATGCTGGA ATGCCAACAA TTTTTGGTCA TAGAAGAGAA CAAAGTGCGG    7620

CAGTACGATT CCATCCAGAA ACTGCTGAAC GAGAGGAGCC TCTTCCGGCA AGCCATCAGC    7680

CCCTCCGACA GGGTGAAGCT CTTTCCCCAC CGGAACTCAA GCAAGTGCAA GTCTAAGCCC    7740

CAGATTGCTG CTCTGAAAGA GGAGACAGAA GAAGAGGTGC AAGATACAAG GCTTTAGAGA    7800

GCAGCATAAA TGTTGACATG GACATTTGC TCATGGAATT GGAGCTCGTG GACAGTCAC    7860

CTCATGGAAT TGGAGCTCGT GGAACAGTTA CCTCTGCCTC AGAAAACAAG GATGAATTAA    7920

GTTTTTTTTT AAAAAGAAA CATTTGGGGA ATTCCTGCAG GAATTCGATA TCAAGCTTAT    7980

CGATATTGTT ACAACACCCC AACATCTTCG ACGCGGGCGT GGCAGGTCTT CCCGACGATG    8040

ACGCCGGTGA ACTTCCCGCC GCCGTTGTTG TTTTGGAGCA CGGAAAGACG ATGACGGAAA    8100

AAGAGATCGT GGATTACGTC GCCAGTCAAG TAACAACCGC GAAAAGTTG CGCGGAGGAG    8160

TTGTGTTTGT GGACGAAGTA CCGAAAGGTC TTACCGGAAA ACTCGACGCA AGAAAAATCA    8220

GAGAGATCCT CATAAAGGCC AAGAAGGGCG GAAAGTCCAA ATTGTAAAAT GTAACTGTAT    8280

TCAGCGATGA CGAAATTCTT AGCTATTGTA ATACTGCGAT GAGTGGCAGG GCGGGGCGTA    8340
```

```
ATTTTTTTAA GGCAGTTATT GGTGCCCTTA AACGCCTGGT GCTACGCCTG AATAAGTGAT      8400

AATAAGCGGA TGAATGGCAG AAATTCGCCG GATCTTTGTG AAGGAACCTT ACTTCTGTGG      8460

TGTGACATAA TTGGACAAAC TACCTACAGA GATTTAAAGC TCTAAGGTAA ATATAAAATT      8520

TTTAAGTGTA TAATGTGTTA AACTACTGAT TCTAATTGTT TGTGTATTTT AGATTCCAAC      8580

CTATGGAACT GATGAATGGG AGCAGTGGTG GAATGCCTTT AATGAGGAAA ACCTGTTTTG      8640

CTCAGAAGAA ATGCCATCTA GTGATGATGA GGCTACTGCT GACTCTCAAC ATTCTACTCC      8700

TCCAAAAAAG AAGAGAAAGG TAGAAGACCC CAAGGACTTT CCTTCAGAAT TGCTAAGTTT      8760

TTTGAGTCAT GCTGTGTTTA GTAATAGAAC TCTTGCTTGC TTTGCTATTT ACACCACAAA      8820

GGAAAAAGCT GCACTGCTAT ACAAGAAAAT TATGGAAAAA TATTCTGTAA CCTTTATAAG      8880

TAGGCATAAC AGTTATAATC ATAACATACT GTTTTTTCTT ACTCCACACA GGCATAGAGT      8940

GTCTGCTATT AATAACTATG CTCAAAAATT GTGTACCTTT AGCTTTTTAA TTTGTAAAGG      9000

GGTTAATAAG GAATATTTGA TGTATAGTGC CTTGACTAGA GATCATAATC AGCCATACCA      9060

CATTTGTAGA GGTTTTACTT GCTTTAAAAA ACCTCCCACA CCTCCCCCTG AACCTGAAAC      9120

ATAAAATGAA TGCAATTGTT GTTGTTAACT TGTTTATTGC AGCTTATAAT GGTTACAAAT      9180

AAAGCAATAG CATCACAAAT TTCACAAATA AAGCATTTTT TCACTGCAT TCTAGTTGTG       9240

GTTTGTCCAA ACTCATCAAT GTATCTTATC ATGTCTGGAT CCGTCGACCG ATGCCCTTGA      9300

GAGCCTTCAA CCCAGTCAGC TCCTTCCGGT GGGCGCGGGG CATGACTATC GTCGCCGCAC      9360

TTATGACTGT CTTCTTTATC ATGCAACTCG TAGGACAGGT GCCGGCAGCG CTCTTCCGCT      9420

TCCTCGCTCA CTGACTCGCT GCGCTCGGTC GTTCGGCTGC GGCGAGCGGT ATCAGCTCAC      9480

TCAAAGGCGG TAATACGGTT ATCCACAGAA TCAGGGGATA ACGCAGGAAA GAACATGTGA      9540

GCAAAAGGCC AGCAAAAGGC CAGGAACCGT AAAAAGGCCG CGTTGCTGGC GTTTTTCCAT      9600

AGGCTCCGCC CCCCTGACGA GCATCACAAA AATCGACGCT CAAGTCAGAG GTGGCGAAAC      9660

CCGACAGGAC TATAAAGATA CCAGGCGTTT CCCCCTGGAA GCTCCCTCGT GCGCTCTCCT      9720

GTTCCGACCC TGCCGCTTAC CGGATACCTG TCCGCCTTTC TCCCTTCGGG AAGCGTGGCG      9780

CTTTCTCATA GCTCACGCTG TAGGTATCTC AGTTCGGTGT AGGTCGTTCG CTCCAAGCTG      9840

GGCTGTGTGC ACGAACCCCC CGTTCAGCCC GACCGCTGCG CCTTATCCGG TAACTATCGT      9900

CTTGAGTCCA ACCCGGTAAG ACACGACTTA TCGCCACTGG CAGCAGCCAC TGGTAACAGG      9960

ATTAGCAGAG CGAGGTATGT AGGCGGTGCT ACAGAGTTCT TGAAGTGGTG GCCTAACTAC     10020

GGCTACACTA GAAGGACAGT ATTTGGTATC TGCGCTCTGC TGAAGCCAGT TACCTTCGGA     10080

AAAAGAGTTG GTAGCTCTTG ATCCGGCAAA CAAACCACCG CTGGTAGCGG TGGTTTTTTT     10140

GTTTGCAAGC AGCAGATTAC GCGCAGAAAA AAAGGATCTC AAGAAGATCC TTTGATCTTT     10200

TCTACGGGGT CTGACGCTCA GTGGAACGAA AACTCACGTT AAGGGATTTT GGTCATGAGA     10260

TTATCAAAAA GGATCTTCAC CTAGATCCTT TTAAATTAAA AATGAAGTTT TAAATCAATC     10320

TAAAGTATAT ATGAGTAAAC TTGGTCTGAC AGTTACCAAT GCTTAATCAG TGAGGCACCT     10380

ATCTCAGCGA TCTGTCTATT TCGTTCATCC ATAGTTGCCT GACTCCCCGT CGTGTAGATA     10440

ACTACGATAC GGGAGGGCTT ACCATCTGGC CCCAGTGCTG CAATGATACC GCGAGACCAC     10500

CGCTCACCGG CTCCAGATTT ATCAGCAATA AACCAGCCAG CCGGAAGGGC CGAGCGCAGA     10560

AGTGGTCCTG CAACTTTATC CGCCTCCATC CAGTCTATTA ATTGTTGCCG GGAAGCTAGA     10620

GTAAGTAGTT CGCCAGTTAA TAGTTTGCGC AACGTTGTTG CCATTGCTAC AGGCATCGTG     10680

GTGTCACGCT CGTCGTTTGG TATGGCTTCA TTCAGCTCCG GTTCCCAACG ATCAAGGCGA     10740
```

-continued

```
GTTACATGAT CCCCCATGTT GTGCAAAAAA GCGGTTAGCT CCTTCGGTCC TCCGATCGTT    10800

GTCAGAAGTA AGTTGGCCGC AGTGTTATCA CTCATGGTTA TGGCAGCACT GCATAATTCT    10860

CTTACTGTCA TGCCATCCGT AAGATGCTTT TCTGTGACTG GTGAGTACTC AACCAAGTCA    10920

TTCTGAGAAT AGTGTATGCG GCGACCGAGT TGCTCTTGCC CGGCGTCAAT ACGGGATAAT    10980

ACCGCGCCAC ATAGCAGAAC TTTAAAAGTG CTCATCATTG GAAAACGTTC TTCGGGGCGA    11040

AAACTCTCAA GGATCTTACC GCTGTTGAGA TCCAGTTCGA TGTAACCCAC TCGTGCACCC    11100

AACTGATCTT CAGCATCTTT TACTTTCACC AGCGTTTCTG GGTGAGCAAA AACAGGAAGG    11160

CAAAATGCCG CAAAAAAGGG AATAAGGGCG ACACGGAAAT GTTGAATACT CATACTCTTC    11220

CTTTTTCAAT ATTATTGAAG CATTTATCAG GGTTATTGTC TCATGAGCGG ATACATATTT    11280

GAATGTATTT AGAAAAATAA ACAAATAGGG GTTCCGCGCA CATTTCCCCG AAAAGTGCCA    11340

CCTGACGCGC CCTGTAGCGG CGCATTAAGC GCGGCGGGTG TGGTGGTTAC GCGCAGCGTG    11400

ACCGCTACAC TTGCCAGCGC CCTAGCGCCC GCTCCTTTCG CTTTCTTCCC TTCCTTTCTC    11460

GCCACGTTCG CCGGCTTTCC CCGTCAAGCT CTAAATCGGG GGCTCCCTTT AGGGTTCCGA    11520

TTTAGTGCTT TACGGCACCT CGACCCCAAA AAACTTGATT AGGGTGATGG TTCACGTAGT    11580

GGGCCATCGC CCTGATAGAC GGTTTTTCGC CCTTTGACGT TGGAGTCCAC GTTCTTTAAT    11640

AGTGGACTCT TGTTCCAAAC TGGAACAACA CTCAACCCTA TCTCGGTCTA TTCTTTTGAT    11700

TTATAAGGGA TTTTGCCGAT TTCGGCCTAT TGGTTAAAAA ATGAGCTGAT TTAACAAAAA    11760

TTTAACGCGA ATTTTAACAA AATATTAACG TTTACAATTT CCCATTCGCC ATTCAGGCTA    11820

CGCAACTGTT GGGAAGGGCG ATCGGTGCGG GCCTCTTCGC TATTACGCCA GCCCAAGCTA    11880

CCATGATAAG TAAGTAATAT TAAGGTACGT GGAGGTTTTA CTTGCTTTAA AAAACCTCCC    11940

ACACCTCCCC CTGAACCTGA AACATAAAAT GAATGCAATT GTTGTTGTTA ACTTGTTTAT    12000

TGCAGCTTAT AATGGTTACA AATAAAGCAA TAGCATCACA AATTTCACAA ATAAAGCATT    12060

TTTTTCACTG CATTCTAGTT GTGGTTTGTC CAAACTCATC AATGTATCTT ATGGTACTGT    12120

AACTGAGCTA ACATAACCCG GGA                                           12143
```

(2) INFORMATION FOR SEQ ID NO: 2:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ix) FEATURE:
  (A) NAME/KEY: -
  (B) LOCATION:1..24
  (D) OTHER INFORMATION:/note= "K18P3 synthetic DNA
   oligo-nucleotide - amplification primer for obtaining
   K18"

(xi) SEQUENCE DESCRIPTION: SEQ ID NO: 2:

```
GCAACGCGTC AGGTAAGGGG TAGG                                          24
```

(2) INFORMATION FOR SEQ ID NO: 3:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ix) FEATURE:

(A) NAME/KEY: -
            (B) LOCATION:1..26
            (C) IDENTIFICATION METHOD:
            (D) OTHER INFORMATION:/note= "K18P4 synthetic DNA
                oligo-nucleotide - amplification primer for obtaining
                K18"

(xi) SEQUENCE DESCRIPTION: SEQ ID NO: 3:

CGAAGATCTG GAGGGATTGT AGAGAG                                              26

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..23
        (C) IDENTIFICATION METHOD:
        (D) OTHER INFORMATION:/note= "K18XH5' synthetic DNA
            oligonucleotide - amplification primer for obtaining
            K18 "

(xi) SEQUENCE DESCRIPTION: SEQ ID NO: 4:

CATAATAACG TCATTTCCTG CCC                                                 23

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..28
        (C) IDENTIFICATION METHOD:
        (D) OTHER INFORMATION:/note= "K18P2* synthetic DNA
            oligo-nucleotide - amplification primer for obtaining
            K18"

(xi) SEQUENCE DESCRIPTION: SEQ ID NO: 5:

GCTACGCGTG AGAGAAAGGA CAGGACTC                                            28

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..21
        (C) IDENTIFICATION METHOD:
        (D) OTHER INFORMATION:/note= "K18NsiI synthetic DNA
            oligo-nucleotide - amplification primer for obtaining
            K18"

(xi) SEQUENCE DESCRIPTION: SEQ ID NO: 6:

CTCACAGTAG GTGCTGAATG C                                                   21

(2) INFORMATION FOR SEQ ID NO: 7:

(i) SEQUENCE CHARACTERISTICS:
        (A) LENGTH: 23 base pairs (B) TYPE: nucleic acid
          (C) STRANDEDNESS: single
          (D) TOPOLOGY: linear (ix) FEATURE:
          (A) NAME/KEY: -
          (B) LOCATION:1..23
          (C) IDENTIFICATION METHOD:
          (D) OTHER INFORMATION:/note= "K18XH3' synthetic DNA
              oligo-nucleotide - amplification primer for obtaining
              K18"

(xi) SEQUENCE DESCRIPTION: SEQ ID NO: 7:

GACACGGACA GCAGGTGTTG TTG                                                 23

(2) INFORMATION FOR SEQ ID NO: 8:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ix) FEATURE:
          (A) NAME/KEY: -
          (B) LOCATION:1..30
          (C) IDENTIFICATION METHOD:
          (D) OTHER INFORMATION:/note= "K18P1 synthetic
              oligo-nucleotide - amplification primer for obtaining
              K18"

(xi) SEQUENCE DESCRIPTION: SEQ ID NO: 8:

CGAGGTACCA ATAACAGTAA AAGGCAGTAC                                          30

(2) INFORMATION FOR SEQ ID NO: 9:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ix) FEATURE:
          (A) NAME/KEY: -
          (B) LOCATION:1..23
          (C) IDENTIFICATION METHOD:
          (D) OTHER INFORMATION:/note= "K18NsiIR synthetic DNA
              oligo-nucleotide - amplification primer for obtaining
              K18"

(xi) SEQUENCE DESCRIPTION: SEQ ID NO: 9:

CACCGGTATA TCACCTTTCC TGC                                                 23

(2) INFORMATION FOR SEQ ID NO: 10:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ix) FEATURE:
          (A) NAME/KEY: -
          (B) LOCATION:1..18
          (C) IDENTIFICATION METHOD:
          (D) OTHER INFORMATION:/note= "cftrp1 synthetic DNA
              oligonucleotide - amplification primer for PCR
              mutagenesis"

(xi) SEQUENCE DESCRIPTION: SEQ ID NO: 10:

GAGACCATGG AGAGGTCG                                                       18

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: -
        (B) LOCATION:1..34
        (C) IDENTIFICATION METHOD:
        (D) OTHER INFORMATION:/note= "TE"

(xi) SEQUENCE DESCRIPTION: SEQ ID NO: 11:

GTTTTTATTT TTAATTTTCT TTCAAATACT TCCA                                34

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..24
        (C) IDENTIFICATION METHOD:
        (D) OTHER INFORMATION:/note= "TE2 synthetic DNA
            oligo-nucleotide - amplification primer for PCR
            mutagenesis"

(xi) SEQUENCE DESCRIPTION: SEQ ID NO: 12:

GTCCGCAAAG CCTGAGTCCT GTCC                                           24

(2) INFORMATION FOR SEQ ID NO: 13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..54
        (C) IDENTIFICATION METHOD:
        (D) OTHER INFORMATION:/note= "K183'SS synthetic DNA
            oligo-nucleotide - amplification primer for PCR
            mutagenesis"

(xi) SEQUENCE DESCRIPTION: SEQ ID NO: 13:

AAATTAAAAA TAAAAACAGA CCTGAAAAAA AAAAAGAGAG AGGTTGTTCC ATGA          54

(2) INFORMATION FOR SEQ ID NO: 14:

(i) SEQUENCE CHARACTERISTICS:
        (A) LENGTH: 49 base pairs
        (B) TYPE: nucleic acid
        (C) STRANDEDNESS: single
        (D) TOPOLOGY: /note= "TEtop synthetic DNA
            oligo-nucleotide - amplification primer for PCR
            mutagenesis"

(ix) FEATURE:
        (A) NAME/KEY: -
        (B) LOCATION:1..49
        (C) IDENTIFICATION METHOD:

(xi) SEQUENCE DESCRIPTION: SEQ ID NO: 14:

GATCTGTTTT TATTTTTAAT TTTCTTTCAA ATACTTCCAC CATGGCCCC                          49

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..25
        (C) IDENTIFICATION METHOD:
        (D) OTHER INFORMATION:/note= "cftr3'SS synthetic DNA
            oligo-nucleotide - amplification primer for PCR
            mutagenesis"

(xi) SEQUENCE DESCRIPTION: SEQ ID NO: 15:

GGTGACTTCC CCCAAATATA AAAAG                                                    25

(2) INFORMATION FOR SEQ ID NO: 16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..23
        (C) IDENTIFICATION METHOD:
        (D) OTHER INFORMATION:/note= "TE1 synthetic DNA
            oligo-nucleotide - amplification primer for PCR
            analysis of CFTR mRNA"

(xi) SEQUENCE DESCRIPTION: SEQ ID NO: 16:

CTGTCCTTTC TCTCACGCGT CAG                                                      23

(2) INFORMATION FOR SEQ ID NO: 17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..16
        (C) IDENTIFICATION METHOD:
        (D) OTHER INFORMATION:/note= "cftrp2 synthetic DNA
            oligo-nucleotide - amplification primer for PCR analysis
            of CFTR mRNA"

(xi) SEQUENCE DESCRIPTION: SEQ ID NO: 17:

GAGGAGTGCC ACTTGC                                                              16

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION:1..24

(C) IDENTIFICATION METHOD:
(D) OTHER INFORMATION:/note= "cftrp3 synthetic DNA
    oligo-nucleotide - amplification primer for PCR analysis
    of CFTR mRNA"

(xi) SEQUENCE DESCRIPTION: SEQ ID NO: 18:

GTTGTTGGAA AGGAGACTAA CAAG                                           24

Figure 20:
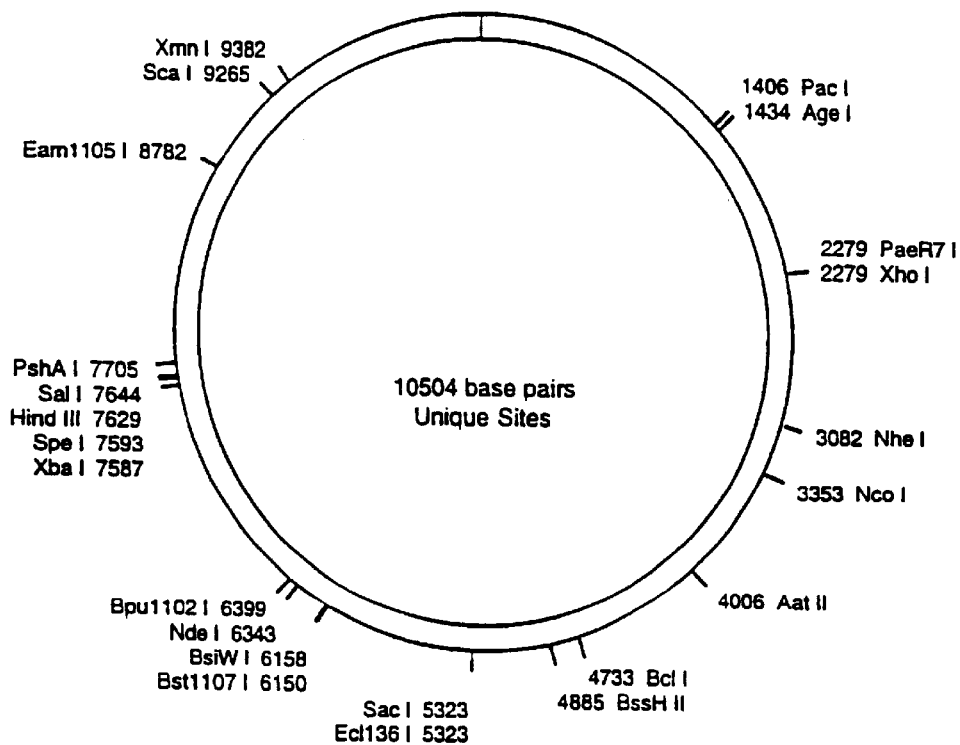

(2) INFORMATION FOR SEQ ID NO: 19:

(i) SEQUENCE CHARACTERISTICS:
    (A) LENGTH: 10504 base pairs
    (B) TYPE: nucleic acid
    (C) STRANDEDNESS: double
    (D) TOPOLOGY: circular (ix) FEATURE:
    (A) NAME/KEY: -
    (B) LOCATION:
    (C) IDENTIFICATION METHOD:
    (D) OTHER INFORMATION:/note= "K18EpilongmTELacZ; Figure 20"

(xi) SEQUENCE DESCRIPTION: SEQ ID NO: 19:

```
GGTACCAATA ACAGTAAAAG GCAGTACATA GCTTGTTGAC TCCACATACT TTATTATAAA      60

ATACTGCCCA ACTTGACAGT TCTGGAATCC AGTGGGGGAA TATAAAGGTG AAAGCAGGAG     120

AGACCCCTCT GACTGGAACC TCTTACCTCC CAGAAGCCTT GTATGCAAAA CCAGTGGGCA     180

TTCATTTGTA TGTTATTTTG CATCCCGTTT GCCTCCCAGC CTTCAGCAGG CCCCGACCCT     240

CCCCTGGCCA GCTTCCACCC TGACTGCCCC CTGGCTGGCT CCCATTGAGC ACTGTGGGCT     300

CTCCCCACCA TTAGGTGACA GATCAGGAAC AATCCAGGCT CAGGCTCTTT ATCTGTGCTC     360

TGCCTCCCAC CTGGCAGGTC CACTGGCCAG GCTTTTCCAG GGTCCCTTCT CTCCCAGGTC     420

TGCCCTACTA TTTGTCCTCC CCTTCCCCCT CAGCTGGTAG CTCGATAAGA ATCAATAGGT     480

CCACTCCAGA GCAAAGAACA CAGCCAAATG TGTCATACCA GGCCCTGCCA GAAAAACGAG     540

CTGCTGGAGC TGACAAACTT GAAGGCCAAA CACCTAAGGT TCCCCCCAAC ACTTCATTCA     600

GCAGGGATGG TCATTCAGCT TCAGGGGGCA GGCAGCATGA AAGCCTCCCT ACCTCCATCC     660

TTCTCACACA GAGGCTGGGG AGAGCATCTT GGAGGATGCA GTCCCCTGGG GCCAGGCTTC     720

TAATCCAGAC AGCCCTTACA AGGGGGGACA GGGGAAGGAC TGGCTTGGAG AAAAGTCCTA     780

GAAAAGAGGG GAGGGGCACT GGCCACCAGG GCTGGGTCGC TGCTATGATG GTCCTAGGAG     840

TGCCTGCCTG TCCTCTCAGG CCCCATGCGA TGTAGGACAC ATTACTTTTA TTTATTTATT     900

TATTTATTTT GAGTCAGAGT TTCGCTCTGG TTGCCCAGGC TGGAGCGCGA CGGCACGATC     960

TTGGCTCACT GCAACCTCTG CCTCCTGGGT TCAAGCGATT CTCCTGCCTC AGCCTCCTGA    1020

GTAGCTGGGA TTACAGGCAC ACACTGTGCT GGTTAATTTT TGTATTTTTA GTAGAGAAGG    1080

GGTGTCACCA TGTTGGTCAG GCTGGTCTCA AATTTTTTTT TTTTTTTTT TTTTTTTTG     1140

AGACAGAGTC TTGCTCTGTT GTCTAGGCTG GAGTGCAGTG GCATCGAACT CTTGACCTCA    1200

AGTGATCCAC CCGCCTCGGC CTCCCAAAGT GCTTGGATTA CAGGCATGAG CCACTGTGCC    1260

CGGCGATGTG GGACACATTA TCATCTCTGT GAGAGATTTT TGGTCTCTTT TGTCACCGCC    1320

CTTCTCTCCC AGCTCCTAGA ACTGGGCCTG GCTCACAGTA GGTGCTGAAT GCATACTGGT    1380

TGAATTGTAA ATGCTCAGGA TTTGTTTAAT TAAGGATGCA GGAAAGGTGA TATACCGGTG    1440

TGCAGAAGTC AGGATGCATT CCCTGTCCAA ATCACAGTGT TCCACTGAGG CAAGGCCCTT    1500

GGGAGTGAGG TCGGGAGAGG GGAGGGTGGT GGAGGGGGCT CAGAGACTGG GTTTGTTTTG    1560

GGGAGTCTGC ACCTATTTGC TGAGTGAATG TATGTGTGTG TGCATTTGAG AGCACACCTC    1620
```

-continued

```
TGTATGATTC GGGTGTGAGT GTGTGTGAGG AAACGTGGGC AGGCGAGGAG TGTTTGGGAG    1680

CCAGGTGCAG CTGGGGTGTG AGTGTGTAAG CAAGCAGCTA TGAGGCTGGG CATTGCTTCT    1740

CCTCCTCTTC TCCAGCTCCC AGCCTTTCTT CCCCGGGACT CCTGGGCTC  CAGGATGCCC    1800

CCAAGATCCC CTCCACAAGT GGATAATTTG GGCTGCAGGT TAAGGACAGC TAGAGGGACT    1860

CACAGGCCAT TCCACCCGCA CACCACCAGA CCCCCAAATT TCTTTTTTCT TTTTTTTTTG    1920

AGACAGAGTC TCACTCTGTC GCCAGGCTGC AGTGGCGCGA TCTCGGCTCA CTGCAACCTC    1980

CGCCTCCCAG GTTCAAGCGA TTCCCCTTCC TCAGCCTCCC AAGTAGCTGA GACTACAGGC    2040

GTGCACCATC ACGTCCGGCT AATTTTTTGT ATTTTAGTAG AGAGGGGTTT CACCATGTTG    2100

GCTAGGATGG TCTCGATCTC CTGACCTCGT GATCCGCCCA CCTAGGCCTC CCAAAGTGCT    2160

GAGATTACAG GCGTGAGCCA CTGCGCCCGG TCAAGACTCC CAAATTTCAA ACTCGCCAGC    2220

ACCTCCTCCA CCTGGGGGAG AAGAGCATAA TAACGTCATT TCCTGCCCTG AAAGCAGCCT    2280

CGAGGGCCAA CAACACCTGC TGTCCGTGTC CATGCCCGGT TGGCCACCCC GTTTCTGGGG    2340

GGTGAGCGGG GCTTGGCAGG GCTGCGCGGA GGGCGCGGGG GTGGGGCCCG GGGCGGAGCG    2400

GCCCGGGGCG GAGGGCGCGG GCTCCGAGCC GTCCACCTGT GGCTCCGGCT TCCGAAGCGG    2460

CTCCGGGGCG GGGGCGGGGC CTCACTCTGC GATATAACTC GGGTCGCGCG GCTCGCGCAG    2520

GCCGCCACCG TCGTCCGCAA AGCCTGAGTC CTGTCCTTTC TCTCACGCGT CAGGTAAGGG    2580

GTAGGAGGGA CCTCAACTCC CAGCCTTGTC TGACCCTCCA ATTATACACT CCTTTGCCTC    2640

TTTCCGTCAT TCCATAACCA CCCCAACCCC TACTCCACCG GGAGGGGTT  GGGCATACCT    2700

GGATTTCCAT CCGCGCACCT AGCCACAGGG TCCCTAAGAG CAGCAGCAGC TAGGCATGGG    2760

AGGGCTCTTT CCCAGGAGAG AGGGGGAAGG GGACAGGGTT GAGAGCTTTA CAGAGGAAGT    2820

GGACAGCATG GAGGGAGGTA AGGAAAGGCC TGTAAAGAGG AGGAGACACT GGCTCTGGCG    2880

GAATGGGGAC TATTGGAGGG TTAAGCGGAT GTGGCTAAGG CTGAGTCATC TAGGAGTAAA    2940

CAAGAGGCCT TCCTTTGGGA GGAGCCAATC CAGGGTGTAG GGGGCCCAGA GTGACCAGGT    3000

GCACTAGGGA AAAAATGCCA GGAGAGGGCC AGGAAGAGGA CTTGTTAGTA GCGACTCACT    3060

TCTGGGCAGG CAGGCCAGCC AGCTAGCCAG CCTGCTGAGG CTTCCCAAGA GGGGCAGAGT    3120

GCTGGGATCT GGGAATCCAG GAAAGGAGGG AATGGGGTGG GGCTAGATGA AAAGGGATAG    3180

GTGTCCAGGG AGAGCCTCTG GCTATTCCTG GGACCAGGAA GTTTTCACTA GGATACATAA    3240

CACTTTTTAC ACACTCACCC CACCCATCCC TGGCTTTCTA TTCATGGAAC AACCTCTCTC    3300

TTTTTTTTTT TCAGGTCTGT TTTTATTTTT AATTTTCTTT CAAATACTTC CACCATGGCC    3360

AAGATCCCTC CTAAGAAGAA GCGCAAAGTC GAGGATCCCG TCGTTTTACA ACGTCGTGAC    3420

TGGGAAAACC CTGGCGTTAC CCAACTTAAT CGCCTTGCAG CACATCCCCC TTTCGCCAGC    3480

TGGCGTAATA GCGAAGAGGC CCGCACCGAT CGCCCTTCCC AACAGTTGCG CAGCCTGAAT    3540

GGCGAATGGC GCTTTGCCTG GTTTCCGGCA CCAGAAGCGG TGCCGGAAAG CTGGCTGGAG    3600

TGCGATCTTC CTGAGGCCGA TACTGTCGTC GTCCCCTCAA ACTGGCAGAT GCACGGTTAC    3660

GATGCGCCCA TCTACACCAA CGTAACCTAT CCCATTACGG TCAATCCGCC GTTTGTTCCC    3720

ACGGAGAATC CGACGGGTTG TTACTCGCTC ACATTTAATG TTGATGAAAG CTGGCTACAG    3780

GAAGGCCAGA CGCGAATTAT TTTTGATGGC GTTAACTCGG CGTTTCATCT GTGGTGCAAC    3840

GGGCGCTGGG TCGTTACGG  CCAGGACAGT CGTTTGCCGT CTGAATTTGA CCTGAGCGCA    3900

TTTTTACGCG CCGGAGAAAA CCGCCTCGCG GTGATGGTGC TGCGTTGGAG TGACGGCAGT    3960
```

```
TATCTGGAAG ATCAGGATAT GTGGCGGATG AGCGGCATTT TCCGTGACGT CTCGTTGCTG    4020

CATAAACCGA CTACACAAAT CAGCGATTTC CATGTTGCCA CTCGCTTTAA TGATGATTTC    4080

AGCCGCGCTG TACTGGAGGC TGAAGTTCAG ATGTGCGGCG AGTTGCGTGA CTACCTACGG    4140

GTAACAGTTT CTTTATGGCA GGGTGAAACG CAGGTCGCCA GCGGCACCGC GCCTTTCGGC    4200

GGTGAAATTA TCGATGAGCG TGGTGGTTAT GCCGATCGCG TCACACTACG TCTGAACGTC    4260

GAAAACCCGA AACTGTGGAG CGCCGAAATC CCGAATCTCT ATCGTGCGGT GGTTGAACTG    4320

CACACCGCCG ACGGCACGCT GATTGAAGCA GAAGCCTGCG ATGTCGGTTT CCGCGAGGTG    4380

CGGATTGAAA ATGGTCTGCT GCTGCTGAAC GGCAAGCCGT TGCTGATTCG AGGCGTTAAC    4440

CGTCACGAGC ATCATCCTCT GCATGGTCAG GTCATGGATG AGCAGACGAT GGTGCAGGAT    4500

ATCCTGCTGA TGAAGCAGAA CAACTTTAAC GCCGTGCGCT GTTCGCATTA TCCGAACCAT    4560

CCGCTGTGGT ACACGCTGTG CGACCGCTAC GGCCTGTATG TGGTGGATGA AGCCAATATT    4620

GAAACCCACG GCATGGTGCC AATGAATCGT CTGACCGATG ATCCGCGCTG GCTACCGGCG    4680

ATGAGCGAAC GCGTAACGCG AATGGTGCAG CGCGATCGTA ATCACCCGAG TGTGATCATC    4740

TGGTCGCTGG GGAATGAATC AGGCCACGGC GCTAATCACG ACGCGCTGTA TCGCTGGATC    4800

AAATCTGTCG ATCCTTCCCG CCCGGTGCAG TATGAAGGCG GCGGAGCCGA CACCACGGCC    4860

ACCGATATTA TTTGCCCGAT GTACGCGCGC GTGGATGAAG ACCAGCCCTT CCCGGCTGTG    4920

CCGAAATGGT CCATCAAAAA ATGGCTTTCG CTACCTGGAG AGACGCGCCC GCTGATCCTT    4980

TGCGAATACG CCCACGCGAT GGGTAACAGT CTTGGCGGTT TCGCTAAATA CTGGCAGGCG    5040

TTTCGTCAGT ATCCCCGTTT ACAGGGCGGC TTCGTCTGGG ACTGGGTGGA TCAGTCGCTG    5100

ATTAAATATG ATGAAAACGG CAACCCGTGG TCGGCTTACG GCGGTGATTT TGGCGATACG    5160

CCGAACGATC GCCAGTTCTG TATGAACGGT CTGGTCTTTG CCGACCGCAC GCCGCATCCA    5220

GCGCTGACGG AAGCAAAACA CCAGCAGCAG TTTTTCCAGT TCCGTTTATC CGGGCAAACC    5280

ATCGAAGTGA CCAGCGAATA CCTGTTCCGT CATAGCGATA ACGAGCTCCT GCACTGGATG    5340

GTGGCGCTGA TGGTAAGCC GCTGGCAAGC GGTGAAGTGC CTCTGGATGT CGCTCCACAA    5400

GGTAAACAGT TGATTGAACT GCCTGAACTA CCGCAGCCGG AGAGCGCCGG CAACTCTGG    5460

CTCACAGTAC GCGTAGTGCA ACCGAACGCG ACCGCATGGT CAGAAGCCGG GCACATCAGC    5520

GCCTGGCAGC AGTGGCGTCT GGCGGAAAAC CTCAGTGTGA CGCTCCCCGC CGCGTCCCAG    5580

GCCATCCCGC ATCTGACCAC CAGCGAAATG GATTTTTGCA TCGAGCTGGG TAATAAGCGT    5640

TGGCAATTTA ACCGCCAGTC AGGCTTTCTT TCACAGATGT GGATTGGCGA TAAAAACAA    5700

CTGCTGACGC CGCTGCGCGA TCAGTTCACC CGTGCACCGC TGGATAACGA CATTGGCGTA    5760

AGTGAAGCGA CCCGCATTGA CCCTAACGCC TGGGTCGAAC GCTGGAAGGC GGCGGGCCAT    5820

TACCAGGCCA AGCAGCGTT GTTGCAGTGC ACGGCAGATA CACTTGCTGA TGCGGTGCTG    5880

ATTACGACCG CTCACGCGTG GCAGCATCAG GGGAAAACCT TATTTATCAG CCGGAAAACC    5940

TACCGGATTG ATGGTAGTGG TCAAATGGCG ATTACCGTTG ATGTTGAAGT GGCGAGCGAT    6000

ACACCGCATC CGGCGCGGAT TGGCCTGAAC TGCCAGCTGG CGCAGGTAGC AGAGCGGGTA    6060

AACTGGCTCG GATTAGGGCC GCAAGAAAAC TATCCCGACC GCCTTACTGC CGCCTGTTTT    6120

GACCGCTGGG ATCTGCCATT GTCAGACATG TATACCCCGT ACGTCTTCCC GAGCGAAAAC    6180

GGTCTGCGCT GCGGGACGCG CGAATTGAAT TATGGCCCAC ACCAGTGGCG CGGCGACTTC    6240

CAGTTCAACA TCAGCCGCTA CAGTCAACAG CAACTGATGG AAACCAGCCA TCGCCATCTG    6300

CTGCACGCGG AAGAAGGCAC ATGGCTGAAT ATCGACGGTT TCCATATGGG GATTGGTGGC    6360
```

```
GACGACTCCT GGAGCCCGTC AGTATCGGCG GAATTCCAGC TGAGCGCCGG TCGCTACCAT   6420

TACCAGTTGG TCTGGTGTCA AAAATATCTT TGTGAAGGAA CCTTACTTCT GTGGTGTGAC   6480

ATAATTGGAC AAACTACCTA CAGAGATTTA AAGCTCTAAG GTAAATATAA AATTTTTAAG   6540

TGTATAATGT GTTAAACTAC TGATTCTAAT TGTTTGTGTA TTTTAGATTC CAACCTATGG   6600

AACTGATGAA TGGGAGCAGT GGTGGAATGC CTTTAATGAG GAAAACCTGT TTTGCTCAGA   6660

AGAAATGCGA TCTAGTGATG ATGAGGCTAC TGCTGACTCT CAACATTCTA CTCCTCCAAA   6720

AAAGAAGAGA AAGGTAGAAG ACCCCAAGGA CTTTCCTTCA GAATTGCTAA GTTTTTTGAG   6780

TCATGCTGTG TTTAGTAATA GAACTCTTGC TTGCTTTGCT ATTTACACCA CAAAGGAAAA   6840

AGCTGCACTG CTATACAAGA AAATTATGGA AAAATATTCT GTAACCTTTA TAAGTAGGCA   6900

TAACAGTTAT AATCATAACA TACTGTTTTT TCTTACTCCA CACAGGCATA GAGTGTCTGC   6960

TATTAATAAC TATGCTCAAA AATTGTGTAC CTTTAGCTTT TTAATTTGTA AAGGGGTTAA   7020

TAAGGAATAT TTGATGTATA GTGCCTTGAC TAGAGATCAT AATCAGCCAT ACCACATTTG   7080

TAGAGGTTTT ACTTGCTTTA AAAAACCTCC CACACCTCCC CCTGAACCTG AAACATAAAA   7140

TGAATGCAAT TGTTGTTGTT AACTTGTTTA TTGCAGCTTA TAATGGTTAC AAATAAAGCA   7200

ATAGCATCAC AAATTTCACA AATAAAGCAT TTTTTTCACT GCATTCTAGT TGTGGTTTGT   7260

CCAAACTCAT CAATGTATCT TATCATGTCT GGATCCCCAG GAAGCTCCTC TGTGTCCTCA   7320

TAAACCCTAA CCTCCTCTAC TTGAGAGGAC ATTCCAATCA TAGGCTGCCC ATCCACCCTC   7380

TGTGTCCTCC TGTTAATTAG GTCACTTAAC AAAAAGGAAA TTGGGTAGGG GTTTTTCACA   7440

GACCGCTTTC TAAGGGTAAT TTTAAAATAT CTGGGAAGTC CCTTCCACTG CTGTGTTCCA   7500

GAAGTGTTGG TAAACAGCCC ACAAATGTCA ACAGCAGAAA CATACAAGCT GTCAGCTTTG   7560

CACAAGGGCC CGGTACCCGG GGATCCTCTA GAACTAGTGG ATCCCCCGGG CTGCAGGAAT   7620

TCGATATCAA GCTTATCGAT ACCGTCGACC GATGCCCTTG AGAGCCTTCA ACCCAGTCAG   7680

CTCCTTCCGG TGGGCGCGGG GCATGACTAT CGTCGCCGCA CTTATGACTG TCTTCTTTAT   7740

CATGCAACTC GTAGGACAGG TGCCGGCAGC GCTCTTCCGC TTCCTCGCTC ACTGACTCGC   7800

TGCGCTCGGT CGTTCGGCTG CGGCGAGCGG TATCAGCTCA CTCAAAGGCG GTAATACGGT   7860

TATCCACAGA ATCAGGGGAT AACGCAGGAA AGAACATGTG AGCAAAAGGC CAGCAAAAGG   7920

CCAGGAACCG TAAAAAGGCC GCGTTGCTGG CGTTTTTCCA TAGGCTCCGC CCCCCTGACG   7980

AGCATCACAA AAATCGACGC TCAAGTCAGA GGTGGCGAAA CCCGACAGGA CTATAAAGAT   8040

ACCAGGCGTT TCCCCCTGGA AGCTCCCTCG TGCGCTCTCC TGTTCCGACC CTGCCGCTTA   8100

CCGGATACCT GTCCGCCTTT CTCCCTTCGG GAAGCGTGGC GCTTTCTCAT AGCTCACGCT   8160

GTAGGTATCT CAGTTCGGTG TAGGTCGTTC GCTCCAAGCT GGGCTGTGTG CACGAACCCC   8220

CCGTTCAGCC CGACCGCTGC GCCTTATCCG GTAACTATCG TCTTGAGTCC AACCCGGTAA   8280

GACACGACTT ATCGCCACTG GCAGCAGCCA CTGGTAACAG GATTAGCAGA GCGAGGTATG   8340

TAGGCGGTGC TACAGAGTTC TTGAAGTGGT GGCCTAACTA CGGCTACACT AGAAGGACAG   8400

TATTTGGTAT CTGCGCTCTG CTGAAGCCAG TTACCTTCGG AAAAAGAGTT GGTAGCTCTT   8460

GATCCGGCAA ACAAACCACC GCTGGTAGCG GTGGTTTTTT TGTTTGCAAG CAGCAGATTA   8520

CGCGCAGAAA AAAAGGATCT CAAGAAGATC CTTTGATCTT TTCTACGGGG TCTGACGCTC   8580

AGTGGAACGA AAACTCACGT TAAGGGATTT TGGTCATGAG ATTATCAAAA AGGATCTTCA   8640

CCTAGATCCT TTTAAATTAA AAATGAAGTT TTAAATCAAT CTAAAGTATA TATGAGTAAA   8700
```

```
CTTGGTCTGA CAGTTACCAA TGCTTAATCA GTGAGGCACC TATCTCAGCG ATCTGTCTAT      8760
TTCGTTCATC CATAGTTGCC TGACTCCCCG TCGTGTAGAT AACTACGATA CGGGAGGGCT      8820
TACCATCTGG CCCCAGTGCT GCAATGATAC CGCGAGACCC ACGCTCACCG GCTCCAGATT      8880
TATCAGCAAT AAACCAGCCA GCCGGAAGGG CCGAGCGCAG AAGTGGTCCT GCAACTTTAT      8940
CCGCCTCCAT CCAGTCTATT AATTGTTGCC GGGAAGCTAG AGTAAGTAGT TCGCCAGTTA      9000
ATAGTTTGCG CAACGTTGTT GCCATTGCTA CAGGCATCGT GGTGTCACGC TCGTCGTTTG      9060
GTATGGCTTC ATTCAGCTCC GGTTCCCAAC GATCAAGGCG AGTTACATGA TCCCCCATGT      9120
TGTGCAAAAA AGCGGTTAGC TCCTTCGGTC CTCCGATCGT TGTCAGAAGT AAGTTGGCCG      9180
CAGTGTTATC ACTCATGGTT ATGGCAGCAC TGCATAATTC TCTTACTGTC ATGCCATCCG      9240
TAAGATGCTT TTCTGTGACT GGTGAGTACT CAACCAAGTC ATTCTGAGAA TAGTGTATGC      9300
GGCGACCGAG TTGCTCTTGC CCGGCGTCAA TACGGGATAA TACCGCGCCA CATAGCAGAA      9360
CTTTAAAAGT GCTCATCATT GGAAAACGTT CTTCGGGGCG AAAACTCTCA AGGATCTTAC      9420
CGCTGTTGAG ATCCAGTTCG ATGTAACCCA CTCGTGCACC CAACTGATCT TCAGCATCTT      9480
TTACTTTCAC CAGCGTTTCT GGGTGAGCAA AAACAGGAAG GCAAAATGCC GCAAAAAAGG      9540
GAATAAGGGC GACACGGAAA TGTTGAATAC TCATACTCTT CCTTTTTCAA TATTATTGAA      9600
GCATTTATCA GGGTTATTGT CTCATGAGCG GATACATATT TGAATGTATT TAGAAAAATA      9660
AACAAATAGG GGTTCCGCGC ACATTTCCCC GAAAAGTGCC ACCTGACGCG CCCTGTAGCG      9720
GCGCATTAAG CGCGGCGGGT GTGGTGGTTA CGCGCAGCGT GACCGCTACA CTTGCCAGCG      9780
CCCTAGCGCC CGCTCCTTTC GCTTTCTTCC CTTCCTTTCT CGCCACGTTC GCCGGCTTTC      9840
CCCGTCAAGC TCTAAATCGG GGGCTCCCTT TAGGGTTCCG ATTTAGTGCT TTACGGCACC      9900
TCGACCCCAA AAAACTTGAT TAGGGTGATG GTTCACGTAG TGGGCCATCG CCCTGATAGA      9960
CGGTTTTTCG CCCTTTGACG TTGGAGTCCA CGTTCTTTAA TAGTGGACTC TTGTTCCAAA     10020
CTGGAACAAC ACTCAACCCT ATCTCGGTCT ATTCTTTTGA TTTATAAGGG ATTTTGCCGA     10080
TTTCGGCCTA TTGGTTAAAA AATGAGCTGA TTTAACAAAA ATTTAACGCG AATTTTAACA     10140
AAATATTAAC GTTTACAATT TCCCATTCGC CATTCAGGCT ACGCAACTGT TGGGAAGGGC     10200
GATCGGTGCG GGCCTCTTCG CTATTACGCC AGCCCAAGCT ACCATGATAA GTAAGTAATA     10260
TTAAGGTACG TGGAGGTTTT ACTTGCTTTA AAAAACCTCC CACACCTCCC CCTGAACCTG     10320
AAACATAAAA TGAATGCAAT TGTTGTTGTT AACTTGTTTA TTGCAGCTTA TAATGGTTAC     10380
AAATAAAGCA ATAGCATCAC AAATTTCACA AATAAAGCAT TTTTTTCACT GCATTCTAGT     10440
TGTGGTTTGT CCAAACTCAT CAATGTATCT TATGGTACTG TAACTGAGCT AACATAACCC     10500
GGGA                                                                 10504
```

EPISOMAL EXPRESSION CASSETTES FOR GENE THERAPY

FIELD OF THE INVENTION

The invention relates to gene therapy episomal expression cassettes to express a transgene in epithelial cells.

BACKGROUND OF THE INVENTION

1.1 Gene Delivery

Demonstration of the feasibility of gene transfer to humans by a number of clinical trials stimulated considerable interest in gene therapy in the scientific community even though no therapeutic benefit has yet been offered to patients (7). Epithelial tissue, particularly lung epithelial tissue, has considerable potential as a target for gene therapy. The lung is a highly suitable organ for in vivo gene therapy treatment of patients with potentially lethal lung disorders, such as cystic fibrosis, cancers of epithelial origin and emphysema because of its large accessible epithelial and endothelial surface area (15). Both virus-based and non-virus-based methods can be used to deliver genes to lungs (6, 15). The use of liposomes as gene transfer agents seems to have some significant advantages for in vivo lung gene therapy (6, 15). First, liposomes offer a wide margin of safety with low toxicity and have already been used to deliver drugs to humans. They can be administered into the lungs as an aerosol, by direct lavage or following intravenous injection. A clinical trial in nasal epithelia showed no adverse effects; nasal biopsies showed no immuno-histological changes (4). Secondly, liposome-complexed DNA can be used to transfect both resting and dividing cells. In addition, large DNA constructs can be accommodated with liposomes for transfection. Finally and most importantly, liposome-mediated gene expression is episomal, thereby avoiding or reducing the risk of random chromosomal insertions. However, one of the major impediments to liposome-mediated in vivo gene therapy is that the currently available expression vectors only offer a very low level of transient transgene expression (15). Therefore, enhancement of the therapeutic gene expression would not only increase the efficacy, but also effectively decrease the already low levels of toxicity by reducing the dose of therapeutic reagent.

1.2 Control of Gene Expression

The inefficient expression of transgenes in lung is, at least in part, due to the lack of proper lung-specific gene expression cassettes (15). An ideal expression cassette for human lung gene therapy should be safe and confer an appropriate level of tissue-specific expression for a reasonable duration. The rational design of expression cassettes for lung gene therapy relies on our knowledge of regulation of gene expression. Regulation of eukaryotic gene expression is a very complicated process.

A particular gene may be expressed in only one type of cell or tissue while others are expressed in most cell types or tissues. For example, cytokeratin genes are expressed predominantly in epithelial cells (26). In contrast, genes encoding proteins involved in translation (protein synthesis) are expressed in every cell type. The activity of a eukaryotic gene can be regulated at any stage during the course of its expression, such as transcription, RNA splicing, RNA stability, translation, or post-translational modification. Current knowledge indicates that transcription and RNA splicing are the major steps for regulation of many eukaryotic genes.

1.2a Transcriptional regulation

Transcription of eukaryotic genes is catalyzed by an RNA polymerase which is recruited to the promoter by multiple protein factors involved in transcription initiation. Regulation of transcription can be attributed to tissue-specific DNA elements (enhancers or silencers) that stimulate or repress transcription through interaction with tissue-specific transcription factors (25). However, these elements may not function if they reside in an inappropriate location on a chromosome, suggesting that chromosomal position and structure also affect gene expression. This has led to discovering a type of regulatory elements called locus control region (LCR) (13). These LCRs, when integrated into chromosomes, confer copy number-dependent and location-independent gene expression. The first LCR was discovered in 5' region of the human $\beta$-globin gene cluster (9, 10, 13). LCRs are now known to be associated with other genes (28, 36) including human cytokeratin 18 and rat LAP (C/EBPb) which direct gene expression in lung cells of transgenic mice (28, 36). Although currently there is no evidence to show that LCRs enhance episomal gene expression, this possibility can not be ruled out since information about the interactions of LCRs with other regulatory elements is still limited. If LCRs increase gene expression, they would be useful in the design of episomal expression cassettes. As lung epithelial cells are not actively dividing, the delivered plasmid DNA may be wrapped by histones or other nuclear factors and kept in a transcriptionally inactive conformation. Although it is generally believed that plasmids when transferred into nucleus do not form chromatin structures, recent experiments by Jeong and Stein demonstrate that some of the transfected DNAs are in chromatin form (17). The presence of a functional LCR in expression cassettes may allow a plasmid to stay in an open conformation.

1.2b Regulation through RNA processing

Regulation of RNA splicing is also very important for tissue-specific and developmentally regulated gene expression (35). This type of regulated RNA splicing or alternative RNA splicing can lead to the production of different proteins from a single gene by inclusion of different exons in different mRNAs. Some introns contain strong enhancers and their exclusion from expression constructs would lead to diminished gene expression. For example, the first intron of the human cytokeratin 18 contains a strong enhancer which is required for expression of the cytokeratin 18 gene (29). Other introns that do not contain enhancers may also affect gene expression. For example, the presence of rpL32 intron 3 leads to a 30-fold increase in mRNA level relative to the intronless rpL32 minigene (21). However, different introns clearly have different effects. For instance, inclusion of intact thymidylate synthase gene intron 4 alone at its normal position in the thymidylate synthase (TS) coding region leads to a decrease in the level of expression relative to that observed with a the intronless TS minigene (21). The details of this splicing regulation of expression are unknown.

1.3 Gene expression in lung enithelial cells

Efficient tissue-specific gene expression can be achieved, in theory, by using tissue-specific promoters, promoter elements, RNA processing signals, and tissue-specific RNA-stabilizing elements. Cell-specific gene expression primarily results from either tissue-specific promoters, and/or tissue-specific regulatory elements, such as enhancers, silencers, and locus control regions (LCRs). However, it is very difficult to design a cassette for lung gene therapy because there is not enough information known about regulation of lung gene expression. Currently, no suitable expression vector for lung gene therapy has been reported. There is a pressing need for an effective expression vector because a number of human CF gene therapy trials have been conducted (7). The SV40 promoter was used to direct CFTR expression in the clinical trial by Caplen et al. (4); we observed that SV40 promoter is not very active even in cultured lung epithelial cells (see FIG. 5) and its expression in rat lung primary cells (the primary cells are first generation cells isolated from the rat lung, i.e. they are not immortalized cell lines cultured for many generations) is undetectable (Plumb and Hu, unpublished results). That might explain the large amounts of plasmid DNA (10 mg to 300 mg/per nostril) used in the study (4). Recently, several cis-acting elements and trans-acting factors regulating lung epithelial gene expression have been identified. The promoters of the SP-A (surfactant protein A), SP-B (surfactant protein B), SP-C (surfactant protein C), SP-D (surfactant protein D) and CC10 (Clara cell 10 kD protein) genes have been extensively analyzed (22, 31, 40, 41). Because these genes are predominately expressed in type II or Clara cells (22), their promoters, unless modified, would not likely be suitable for expressing genes in epithelial cells of conducting airways, which represent the primary target for CF lung gene therapy.

1.4 Epithelial Expression Cassette for Lung Gene Therapy

Because of the low efficiency in liposome-mediated gene expression, strong viral promoters are often used in gene therapy studies. However, this may not be the ideal approach for liposome-mediated lung gene therapy. For example, the CMV major immediate early gene promoter has been shown to be very strong for transient expression of transgenes in cultured cells, but two studies have shown it to be a poor promoter for lung gene expression in transgenic mice (1, 33). There is no evidence to show the CMV promoter can confer sustained episomal gene expression in vivo. Although it is unreasonable to expect a permanent transgene expression from an episomal plasmid, long lasting expression even at a low level may offer considerable clinical benefits to gene therapy patients. In addition, viral promoters may not confer tissue-specificity. Since currently the nuclear uptake of delivered DNA is highly inefficient (44) in addition to the low efficiency of liposome-mediated gene expression, no one would worry about the effect of non-specifically expressing a therapeutic gene in vivo. However, when the nuclear uptake and liposome-delivery technology are improved, this has to be seriously considered because there must be an advantage for nature to select genes, such as the cystic fibrosis transmembrane conductance regulatory gene (CFTR), to be epithelium-specific.

If human DNA regulatory elements could direct tissue-specific expression of therapeutic genes at a comparable level to that from strong viral promoters in lung epithelial cells, and sustain gene expression longer than the viral promoters, it would be advantageous to use them for lung gene therapy. At present, there is no suitable expression vector for epithelial tissue gene therapy. There is a need to develop gene therapy cassettes that use human DNA regulatory elements which naturally express genes in epithelial cells and can be used to direct the expression of therapeutic genes. It would be particularly useful if there was an expression cassette that could direct a high level of reporter gene expression in vivo and in vitro. The expression cassette should be safe and confer an appropriate level of tissue-specific expression for a reasonable duration. The expression cassette should be capable of use in epithelial cells, such as submucosal cells.

BRIEF DESCRIPTION OF THE DRAWINGS

Preferred embodiments of the invention will be described in relation to the drawings in which:

FIG. 1A shows modification of the GUS reporter gene. FIG. 1B shows chemiluminescent assays of GUS gene expression. RFLE, rat fetal lung primary epithelial cells. The Bioorbit Luminometer (model number 1253) was used and 1 reading unit from this model equals 10,000 reading units from other models such as Berthold Lumat LB 9501.

FIG. 2A shows expression of the green fluorescent protein in cultured human lung cells. A549 cells were transfected with pGREENLANTERN-1 (GIBCO BRL) and visualized under a fluorescent microscope (bottom panel) 2 days post-transfection. The phase-contrast view of the same cells is shown in the top panel. FIG. 2B shows expression of the green fluorescent protein in human cystic fibrosis bronchial epithelial cells. IB3 cells were transfected with pGREENLANTERN-1 (GIBCO BRL) and visualized under a fluorescent microscope (bottom panel) 2 days post-transfection. The phase-contrast view of the same cells is shown in the top panel.

FIG. 4A shows the genomic structure of the human cytokeratin 18 gene (K18), in which exons 1 through 7 are depicted as solid boxes and DNAse I hypersensitive sites as arrows. Intron-1 fragment covers from the end of exon 1 to the beginning of exon 2. The minimal promoter fragment spans 310 base pairs between a unique Xhol (X) site and the K18 translation initiation, excluding the start codon. Enhancer-long and Enhancer fragments cover regions from Hind III (H) to Nsi I sites and from Nsi I to Xho I sites, respectively. FIG. 4B shows the simplified structures of the promoterless SEAP construct (CloneTech) and a series of its derivatives which contain various segments of K18 untranslated sequence, as well as their relative expression levels. FIG. 4C shows the structure of K18Epilong TECFTR, which is identical to K18EpilongSEAP except that the reporter gene SEAP is replaced by CFTR cDNA with a translational enhancer (adapted from Alfalfa Mosaic Virus RNA4) immediately upstream of the CFTR coding sequence."

"FIGS. 9A–9C Splicing of the K18-CFTR chimeric RNA transcript. FIG. 9A shows a schematic diagram of the K18-CFTR chimeric RNA transcript and positions of the primers used in RT-PCR. FIG. 9B shows RT-PCR products from total RNAs isolated from the CFTR transfected IB3 and rat fetal primary epithelial cells. The types of cells and primer sets are indicated on the top. Lane 4 shows the 1 kb ladder. The 712- and 640-bp bands are the expected PCR products from these two primer sets. The stars indicate the mis-spliced products. RNAs from untransfected cells do not yield any bands (data not shown). FIG. 9C shows the K18 intron 1 sequences critical for splicing [SEQ ID NO:20].

FIGS. 10A–10C Identification of the cryptic 3' splice-sties in the CFTR coding region and improvement of the splicing efficiency of the k18-CFTR chimeric RNA transcript by mutagenesis. FIG. 10A shows a schematic diagram of the structures of k18Epilong TECFTR and the RNA transcript. Primers used for RT-PCR in FIG. 11 are depicted as arrows. FIG. 10B shows DNA sequences of k18Epilong TECFTR at K18 3' splice site and two cryptic splice sites in the CFTR coding region [SEQ. ID NOS. 21 to 23]. FIG. 10C shows DNA sequences of K18mCFTR at respective sites (nucleotide nos. 3293–3325, 3398–3408 and 3611–3626 of [SEQ ID NO:1]). Mutations introduced are indicated by asterisks."

The lung was dissected out from a 14 day transgenic mouse fetus and stained with X-gal for 3 hr. The K18mLacZ has been demonstrated clearly expressing in airways of the lung.

Figure 14:

FIG. 14 A lung of a normal mouse fetus. The lung was excised out from a 14 day mouse fetus and stained with X-gal overnight.

Figure 15:
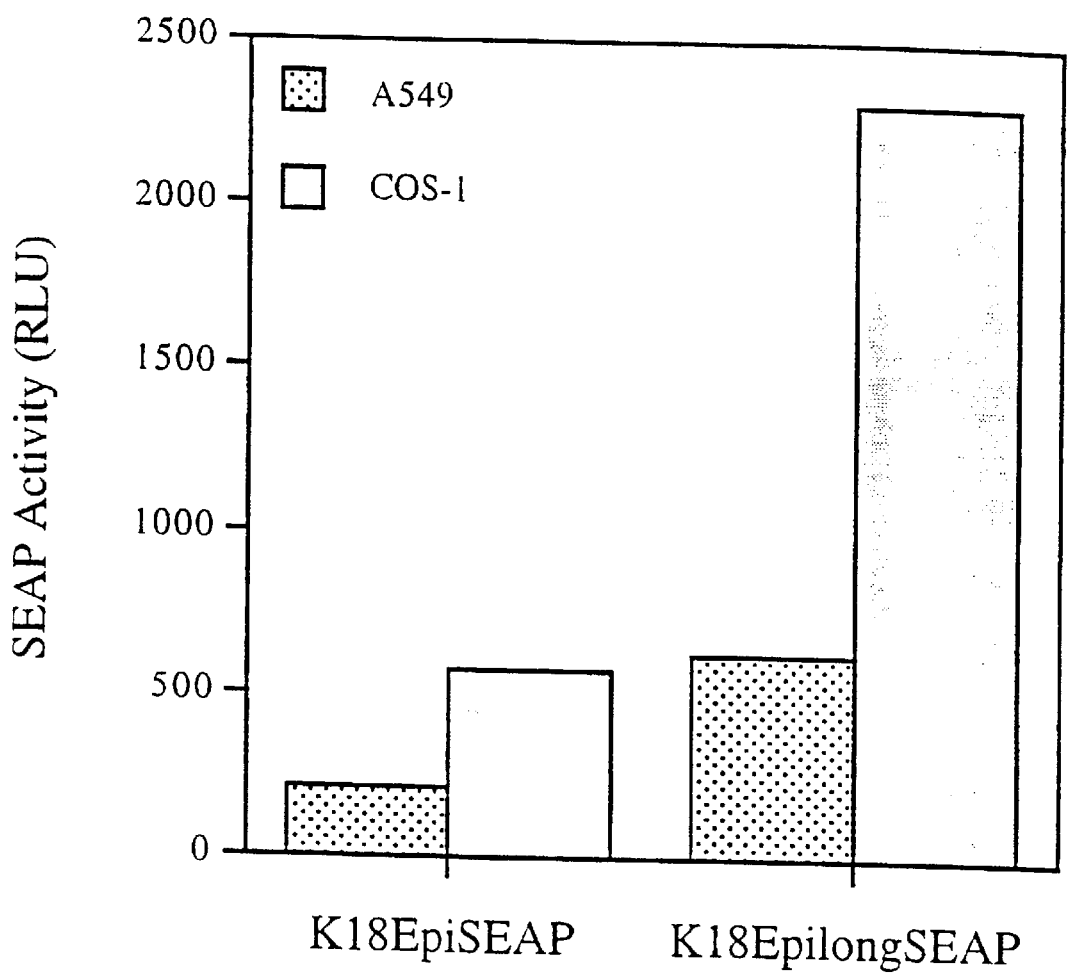

FIG. 15 Enhancer activity of the 1.4 kb DNA fragment from 5' region of the human K18 gene. A549 cells and COS-1 cells were transfected with K18EpiSEAP or K18EpilongSEAP which contains the distal enhancer. SEAP activities in the culture media are normalized to total protein.

Figure 16:
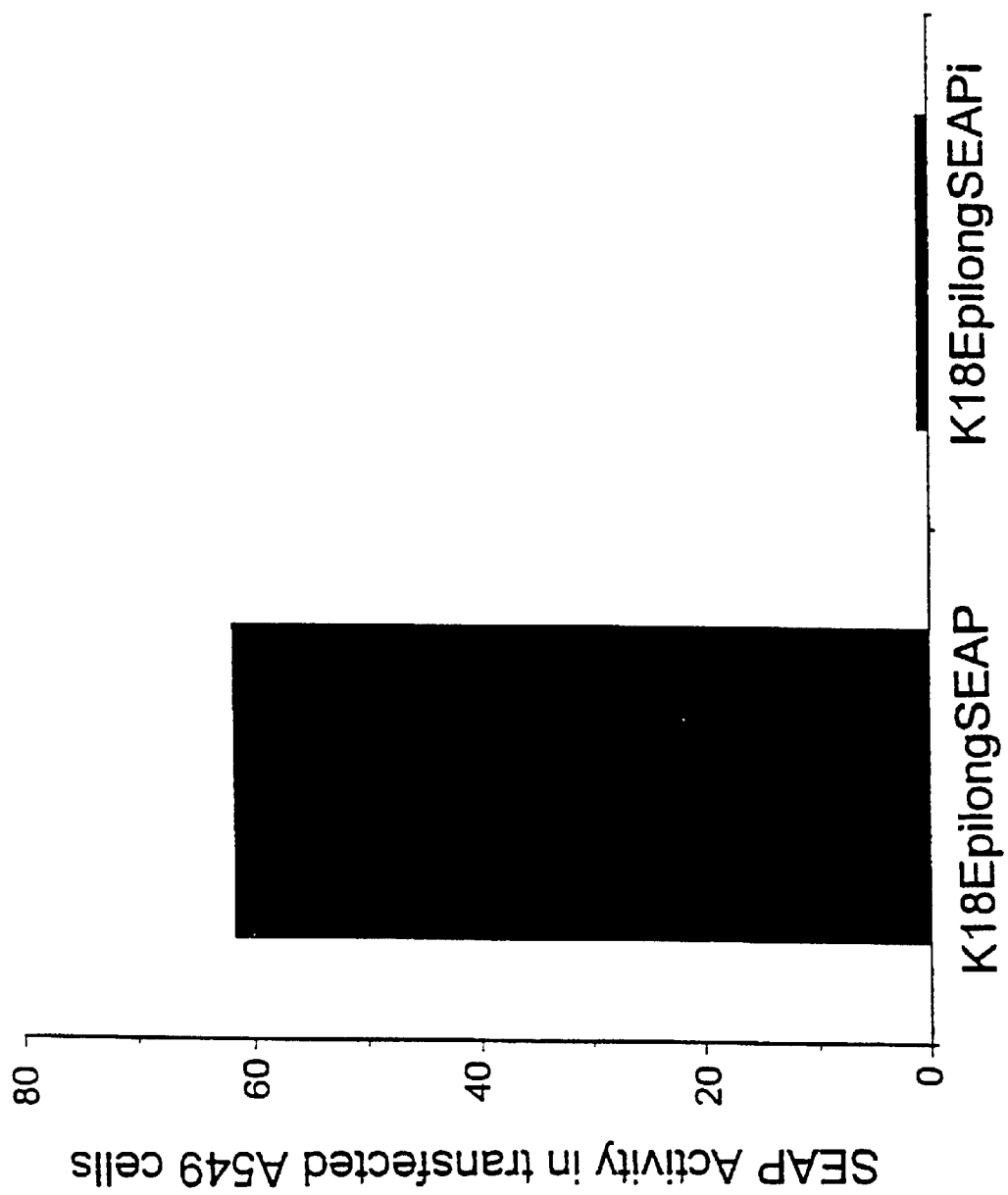

FIG. 16 The position effect of K18 intron 1 on reporter gene expression. In K18EpilongSEAPi construct, the intron was moved to the down stream of the SEAP coding region. Relocating this intron abolished the expression of the SEAP reporter gene by the construct.

Figure 17:

FIG. 17 Temporal expression of the lacZ reporter gene in lung airways of the transgenic fetuses. A negative control lung stained with X-gal under the same conditions is shown on the left, at each time point.

Figure 18:

FIG. 18 Submucosal expression of the lacZ reporter gene. The left panel shows a horizontal tissue section from the lower part of the trachea of a control mouse. The middle panel shows a horizontal tissue section from the lower part of the trachea of a transgenic mouse. The right panel shows submucosal expression of the reporter gene in a tissue section of the upper part of the trachea from the same transgenic mouse.

Figure 19:
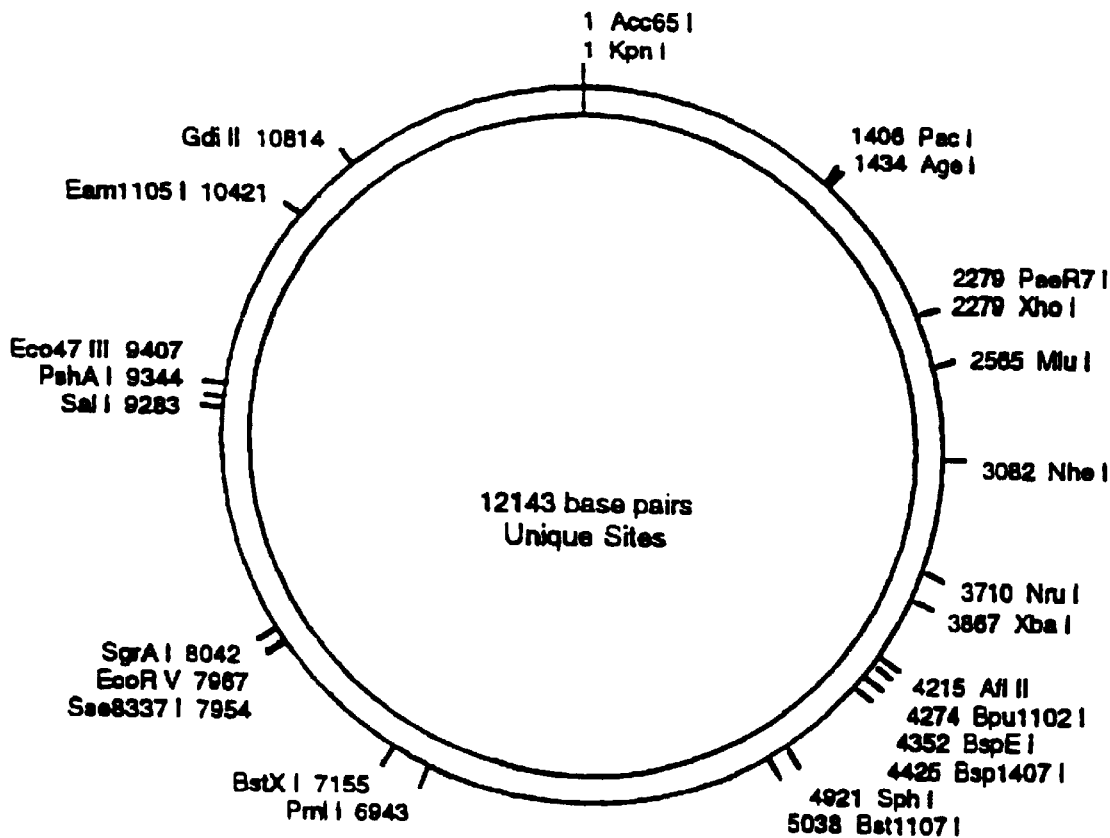

FIG. 19 K18EpilongmCFTR [SEQ ID NO:1] restriction map.

FIGS. 20A–20C (a) DNA sequence of K18EpilongmTELacZ [SEQ ID NO:19] (b) restriction map; (c) features.

Figure 21:
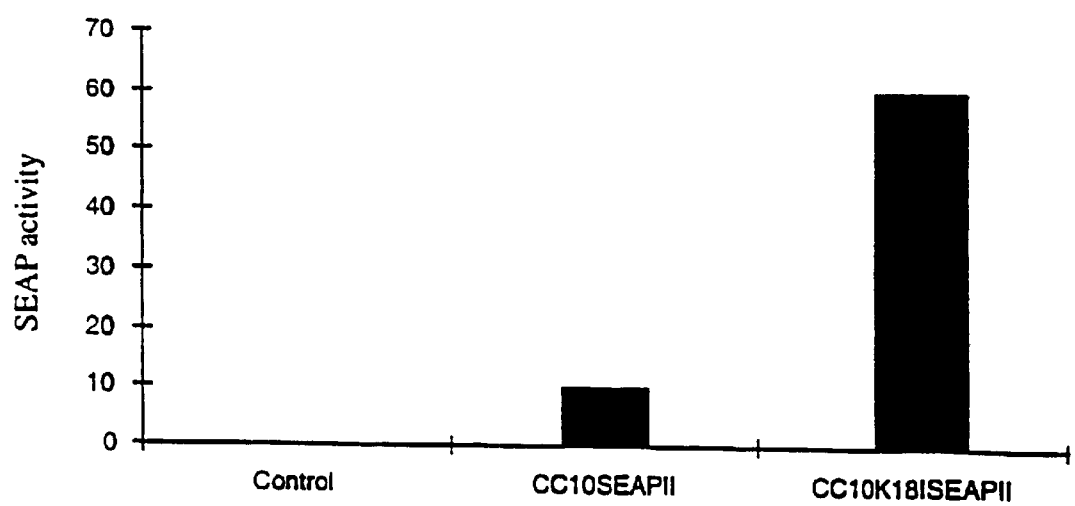

FIG. 21 Enhancement of human CC10 expression by intron 1 of the human cytokeratin 18 gene in A549, a cell line of human lung carcinoma origin.

SUMMARY OF THE INVENTION

The invention satisfies the need for a suitable expression vector for epithelial tissue gene therapy. The expression cassettes of this invention contain human DNA regulatory elements which naturally express genes in epithelial cells and direct the expression of therapeutic genes. For example, the regulatory elements may be from the human cytokeratin 18 gene. The expression cassettes also direct a high level of reporter gene expression in vivo and in vitro. The expression cassettes are safe and confer an appropriate level of tissue-specific expression for a reasonable duration. The expression cassettes may be used in epithelial cells, such as submucosal cells.

The invention also satisfies the need for expression cassettes using epithelial cell specific regulatory elements from mammals. In a preferred embodiment, the human cytokeratin 18 gene regulatory elements are used. Certain elements of the cytokeratin 18 gene from other mammals may also be beneficially used with the expression cassettes.

The invention also relates to a host cell (isolated cell in vitro or a cell in vivo) containing a DNA sequence including: an expression cassette of the invention and the DNA sequence of a gene to be expressed. In a preferred embodiment, the DNA sequence is operatively linked to the expression cassette and capable of expression in the cell and the DNA sequence encodes a protein selected from the group consisting of: 1) a CFTR protein; 2) a protein having sequence similarity to CFTR and 3) a protein having CFTR activity.

The invention is an expression cassette for the episomal expression of a transgene in targeted epithelial cells, which consists of regulatory elements of the human cytokeratin gene and a transgene. In one embodiment of the invention, the expression cassette is targeted to a lung epithelial cell. The regulatory elements may comprise a promoter, the 5' region and modified intron 1 of the human cytokeratin 18 gene.

In the cassette, the human cytokeratin gene is the human cytokeratin 18 gene. The regulatory elements of the cassette are from the 5' region of the human cytokeratin 18 gene. The regulatory elements may also consist of a promoter, the 5' region and intron 1 of the human cytokeratin 18 gene. The cassette may also contain an enhancer.

The transgene in the cassette can be the cystic fibrosis transmembrane conductance regulatory gene. In another embodiment, the transgene in the cassette can consist of an enhancer and a modified cystic fibrosis transmembrane conductance regulatory (CFTR) gene.

The cells targeted by the cassette may be epithelial cells, such as submucosal cells.

A liposome may be used to deliver the expression cassette construct.

Cells may be transfected by the expression cassette construct. In one embodiment, the cells are part of tissue in a lung.

The invention also includes a method of treating a patient having a lung disorder, by administering to the patient a liposome containing the cassette so that the cassette transfects a targeted lung cell. The method of administration of the liposome may be selected from a group consisting of aerosol administration, intratracheal instillation and intravenous injection. The expression cassette can be used in treatment of a disorder such as cystic fibrosis, emphysema, and cancers of epithelial origin arising in the lung or other organs.

Another aspect of the invention relates to an expression cassette for the episomal expression of a transgene in a targeted epithelial cell, consisting of: regulatory elements of a human gene, and a transgene operatively associated with the regulatory elements and capable of expression in the epithelial cell.

The invention also relates to an expression cassette for the episomal expression of a transgene in a targeted epithelial cell, consisting of: regulatory elements of a cytokeratin gene, and a transgene operatively associated with the regulatory elements and capable of expression in the epithelial cell. In a preferred embodiment, the epithelial cell is a lung epithelial cell. The human gene is preferably a cytokeratin gene. The cytokeratin gene is preferably a mammalian cytokeratin gene. The cytokeratin gene is preferably the human cytokeratin 18 gene.

The regulatory elements are preferably from the 5' region of the human cytokeratin 18 gene (all or part of the 5' region including modifications thereto, provided the cassette is fictional). In another embodiment, the regulatory elements comprise a promoter, the 5' region (or modified 5' region, provided the cassette is functional) and intron 1 (or modified intron 1, provided the cassette is functional) of the human cytokeratin 18 gene.

In another embodiment, the cassette consists of a promoter, the 5' region (or modified 5' region provided the cassette is functional) and modified intron 1 of the human cytokeratin 18 gene. In another embodiment, the cassette may comprise an enhancer.

The transgene is preferably selected from the group consisting of a cystic fibrosis transmembrane conductance regulatory (CFTR) gene, a gene having at least 70% sequence identity with CFTR and encoding a protein having CFTR activity, and a gene encoding a protein having CFTR activity. In another embodiment, the transgene comprises an enhancer and a modified cystic fibrosis transmembrane conductance regulatory (CFTR) gene. The targeted epithelial cell is preferably a submucosal cell.

The invention also includes a liposome comprising the construct (or expression cassette). The invention also includes a transfected cell comprising the construct of claim 1, claim 2 or claim 6 and lung tissue comprising the cell of claim 15.

The invention also relates to an expression cassette for treating a defect in the CFTR gene in a target epithelial cell, the expression cassette comprising: the DNA of or corresponding to at least a portion of the DNA regulatory elements of a cytokeratin gene which DNA is capable of regulating gene expression in the target epithelial cell; and a gene, operatively associated with the expression cassette elements and capable of expression in the epithelial cell, the gene encoding a protein selected from the group consisting of a CFTR protein; a protein having at least 70% sequence identity with the CFTR protein and having CFTR activity and a protein having CFTR activity.

In alternate embodiments, the protein has at least 80%, at least 90%, at least 95%, at least 96%, at least 97%, at least 98%, and most preferably at least 99% sequence identity with the CFTR protein and has CFTR activity.

The expression cassette may comprise the DNA sequence in [SEQ ID NO. 1 ]) or the sequence shown in FIG. 19, or a modification or fragment of these sequences. In another embodiment, the expression cassette has at least 70% sequence identity to the sequence in [SEQ ID NO: 1]. In one embodiment of the invention, the defect being treated with the cassette causes cystic fibrosis. The target cell is preferably a lung epithelial cell. The cytokeratin gene is preferably cytokeratin 18. The cytokeratin gene is preferably a human cytokeratin gene (or a cytokeratin gene from another mammal). The DNA regulatory elements from the cytokeratin 18 gene are preferably selected from the group consisting of: a promoter, the 5' region and modified intron 1.

Another aspect of the invention relates to an epithelial cell containing recombinant human DNA regulatory elements and a gene operatively associated with the regulatory elements, the cell expressing proteins not normally expressed by the cell at biologically significant levels. The DNA regulatory elements preferably comprise cytokeratin DNA regulatory elements. The cytokeratin is preferably cytokeratin 18 (from a human or another mammal).

The DNA regulatory elements are preferably selected from the group consisting of: a promoter, the 5' region and modified intron 1. The cell is preferably a human epithelial cell. In another embodiment, the cell is a human cystic fibrosis-associated cell.

The cell preferably contains a gene expressing a protein selected from the group consisting of: a CFTR protein, a protein at least 70% sequence identity with the CFTR protein and having CFTR activity; and a protein having CFTR activity.

The invention also relates to an epithelial cell containing recombinant cytokeratin DNA regulatory elements and a gene operatively associated with the regulatory elements, the cell expressing a protein not normally expressed by the cell at biologically significant levels. The cytokeratin is preferably cytokeratin 18 from a human (or another mammal).

The DNA regulatory elements are preferably selected from the group consisting of: a promoter, the 5' region and modified intron 1 (or fragments or modifications of these regions). The cell is preferably a human epithelial cell. In another embodiment, the cell is a human cystic fibrosis-associated cell. The cell has a gene preferably expressing a protein selected from the group consisting of: a CFTR protein, a protein having at least 70% sequence identity with the CFTR protein and having CFTR activity; a protein having CFTR activity.

The invention also includes a method of treating a patient having a lung disorder, comprising administering to the patient a liposome containing the cassette of the invention whereby the cassette transfects targeted lung cells. The method of administration is preferably selected from a group consisting of aerosol administration, intratrachel instillation and intravenous injection. The disorder treated includes cystic fibrosis, cancers of epithelial origin and emphysema.

The invention also includes a method for treating a defect in a gene in a target epithelial cell, consisting of: administering to the epithelial cell an amount of an expression cassette of the invention so that the expression cassette is inserted in the epithelial cell and expressing the gene to produce the protein.

The invention also includes a method for treating defective chloride ion transport in a cystic fibrosis-associated epithelal cell in a subject having cystic fibrosis, consisting of: administering to the epithelial cell an amount of an expression cassette of the invention so that the expression cassette is inserted in the epithelial cell; expressing the gene to produce the protein so that the protein is transported to the plasma membrane and generates chloride channels in the cystic fibrosis-associated epithelial cell of the subject.

The invention also relates to a pharmaceutical composition comprising a therapeutically effective amount of the expression cassette and a pharmaceutically acceptable carrier. The invention also relates to a composition comprising the expression cassette and a carrier.

Another aspect relates to the use of the expression cassette for treatment of a disease, disorder or abnormal physical state selected from a group consisting of cystic fibrosis, cancers of epithelial origin and emphysema.

DETAILED DESCRIPTION OF THE INVENTION

This invention relates to expression cassettes for expressing therapeutic genes or other genes of interest in epithelial cells. The expression cassettes are preferably constructed from human DNA regulatory elements that naturally express genes in epithelial cells to direct the expression of transgenes for use in research, protein production and gene therapy in lung and other organs. The expression cassettes use human DNA regulatory elements that are specifically expressed in epithelial cells to provide high levels of protein expression.

The expression cassettes may be used in vivo or in vitro. Epithelial cells transformed in vitro can be used as a research tool or for protein production. The expression cassettes are also useful for gene therapy by transforming cells in vivo to express a therapeutic protein. Gene therapy may be used to treat diseases such as cystic fibrosis, cancers of epithelial origin or emphysema. For example, if one were to upregulate the expression of a gene, one could insert the sense sequence into the expression cassette. If one were to downregulate the expression of the gene, one could insert the antisense sequence into the expression cassette. Techniques for inserting sense and antisense sequences (or fragments of these sequences) would be apparent to those skilled in the art. The gene or gene fragment may be either isolated from a native source (in sense or antisense orientations), synthesized, a mutated native or synthetic sequence or a combination of these.

When the DNA regulatory elements used in the episomal expression cassettes are from human genome, these elements offer better compatibility for human gene therapy because the authentic protein factors interacting with these DNA elements are present in targeted cells. These cassettes are epithelium-specific and highly efficient; the cell-specificity increases the efficacy and avoids any adverse effects resulting from expression of the therapeutic gene in non-targeted cells. The high efficiency of gene expression is also critical to minimize the dosage of the therapeutic reagents from gene therapy. Additionally, even in cultured cells, the expression from these constructs last longer than the viral promoter based-expression cassette (see FIG. 6).

The expression cassettes of the invention may be used to treat fatal diseases, such as cystic fibrosis which are caused by genetic abnormalities in epithelial cells. The expression of the cystic fibrosis transmembrane conductance regulator (CFTR) gene in human lungs after birth is localized predominately in the epithelial cells of trachea and large bronchi (37), especially in the submucosal cells (11, 12). In cystic fybrosis patients, death may result from lung failure caused by the genetic abnormality.

In a preferred embodiment, the human gene regulatory elements are from the cytokeratin 18 gene. In another embodiment of the invention, cytokeratin 18 gene regulatory elements from other mammals may be used alone or in combination with human cytokeratin 18 gene regulatory elements. Other epithelial cell specific DNA regulatory elements may also be combined in the expression cassettes of the invention.

The following steps are preferably used to design a CFTR expression cassette: first generating a series of DNA constructs that were assessed in cell lines for the expression of reporter genes or the human CFTR gene, then examining selected constructs in primary cells and whole tissue sections, and finally testing selected constructs in mice and humans. In a preferred embodiment, the expression cassette directs a high level of reporter gene expression in human epithelial cells in vivo and in vitro and in rat fetal lung primary epithelial cells. The cassette may be modified to efficiently direct expression of the human CFTR gene with a change in the CFTR coding sequence. The modified expression cassette directs efficient and cell-specific gene expression in lung epithelia of the transgenic mice and human epithelial cells in vivo and in vitro.

Episomal Expression Cassettes

The advantages of using human regulatory elements in the expression cassettes of the invention are described above. In a preferred embodiment of the invention, the human regulatory elements are from a human cytokeratin gene and most preferably from the human cytokeratin 18 gene. These elements control the expression of a transgene expressed in epithelial cells. The specific regulatory elements chosen for a particular cassette may vary depending on factors such as the level of activity of the cassette desired or the characteristics of the gene to be expressed. One skilled in the art can modify the sequences of the regulatory elements and the gene to be expressed using techniques disclosed in this application and known in the art.

Designing an Expression Cassette

Figure 7:
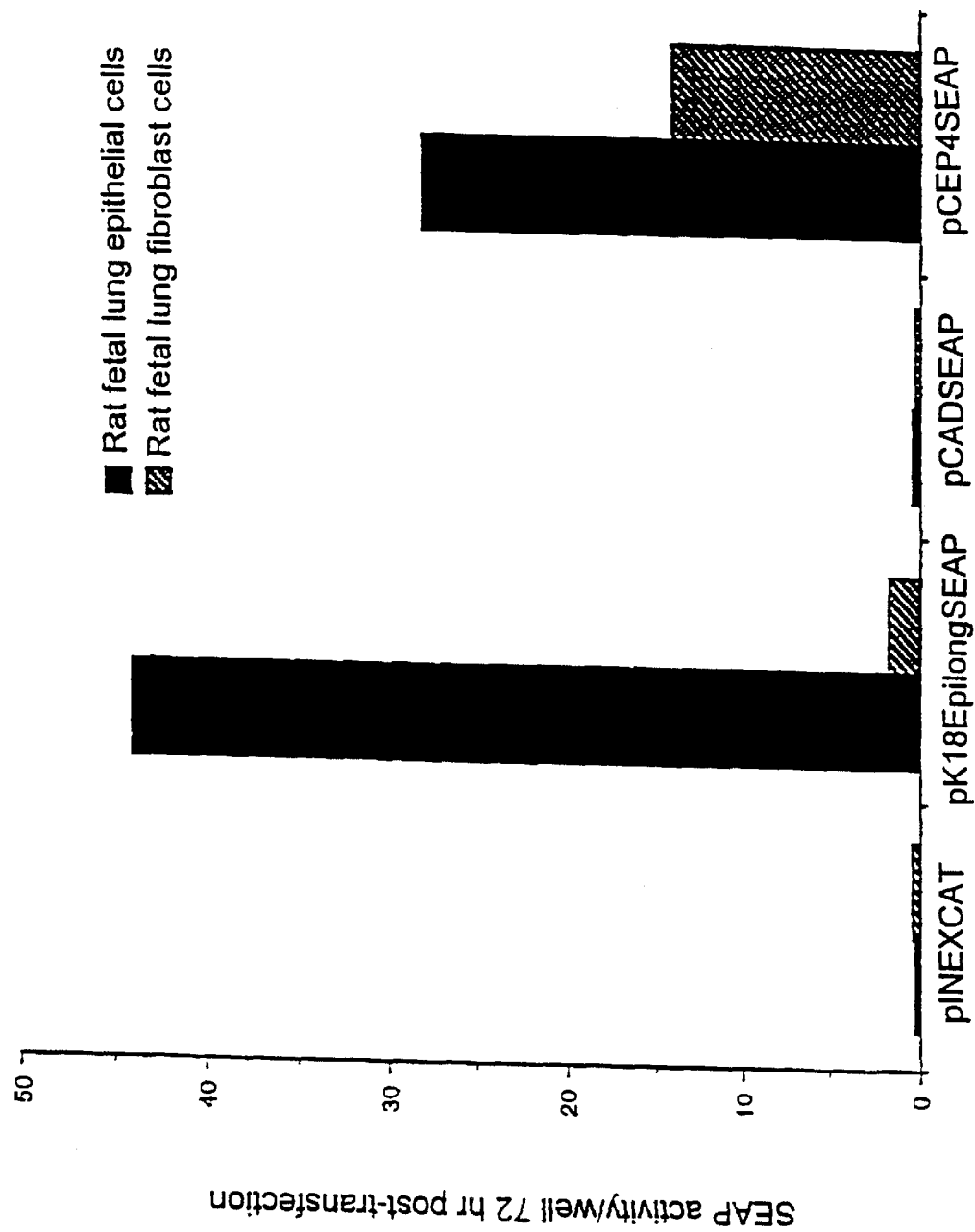
FIG. 7 Expression of K18EpilongSEAP in rat fetal lung primary cells. Both epithelial cells and fibroblast cells were transfected with plasmid DNA and DODAC:DOPE at 1:10 ratio. The plasmid, pINXCAT was used as a negative control. pCEP4SEAP contains the CMV promoter.

K18EpilongSEAP (the construct K18Epilong plus the reporter system SEAP) directed a high level of the SEAP marker in rat lung primary cells (FIG. 7). Regulatory elements were derived from the human cytokeratin 18 gene and combined to form the K18Epilong sequence. The SEAP reporter gene system (see Example 1) was inserted into the cassette to measure levels of expression in epithelial cells. K18Epilong included the following cytokeratin 18 gene regulatory elements: 1) intron 1 (which contains a strong enhancer), 2) the K18 promoter, and 3) two 5' fragments (which greatly enhance the level of gene expression). These elements were kept in their original configuration in K18EpilongSEAP as much as possible in the expression cassette, however, other configurations may be used. Keeping the elements in their original configuration is preferable, where possible, to preserve interactions among transcription factors bound to these elements.

Figure 4A:
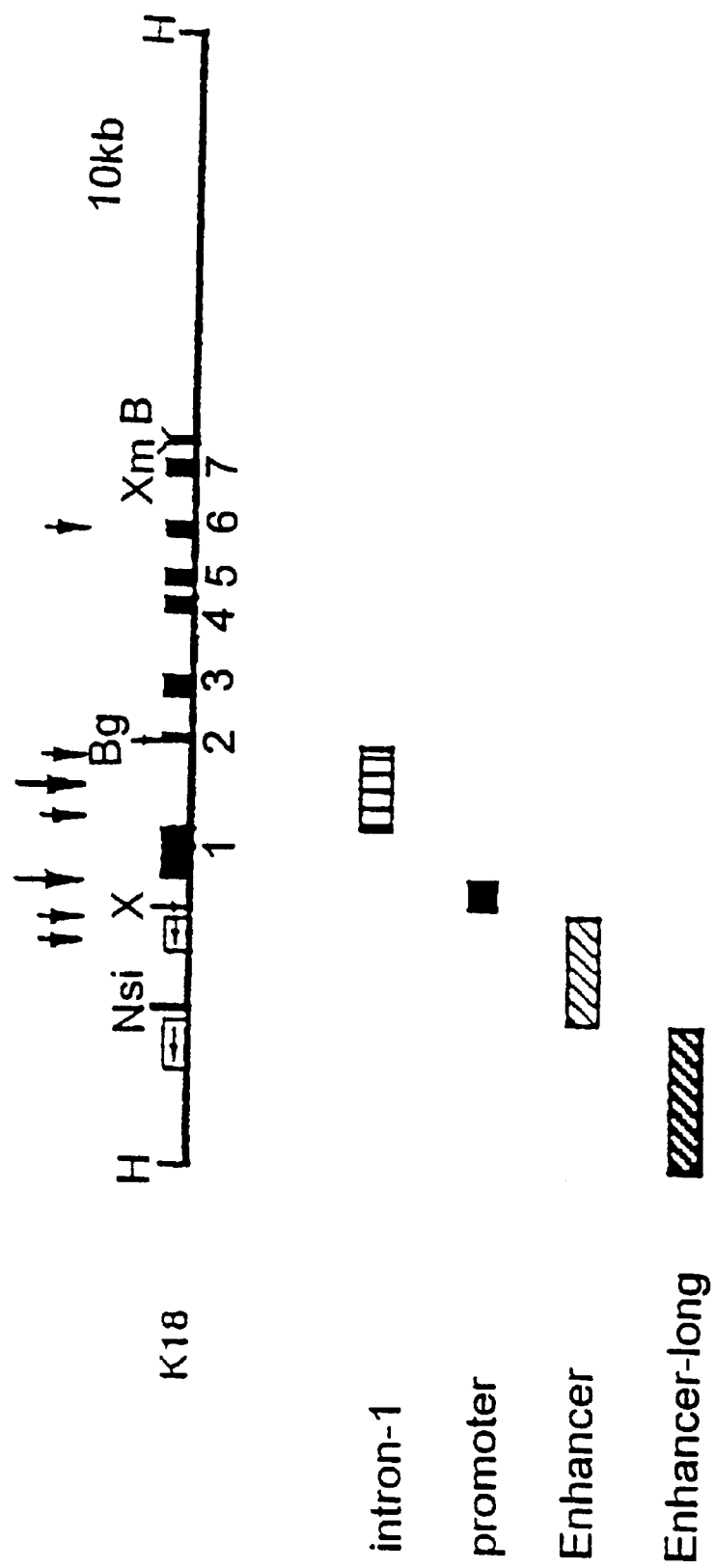
FIGS. 4A–4C Schematic diagrams of SEAP and CFTR expression constructs.
Figures 4B, 4C:
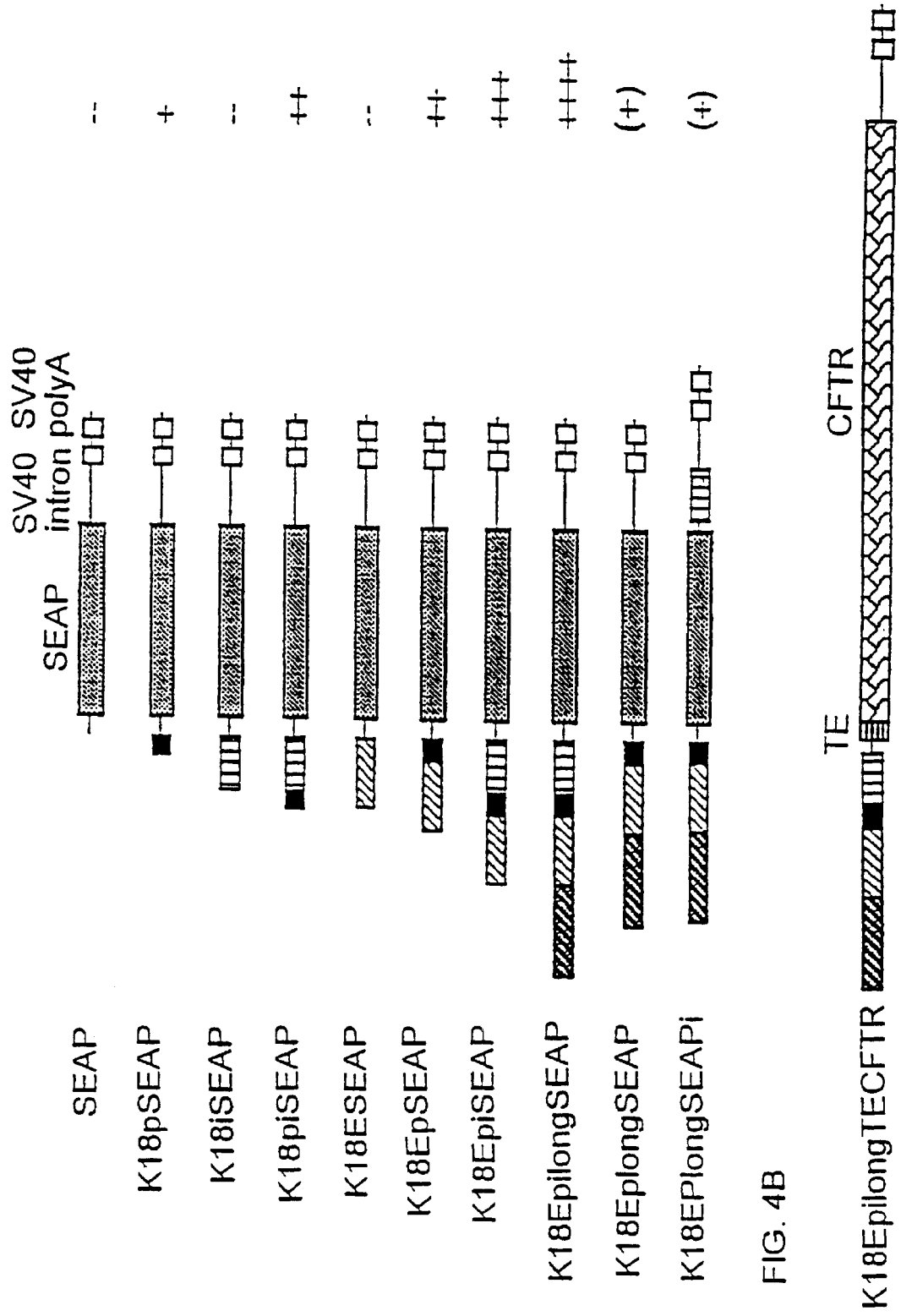

Many modifications may be made to the expression cassette DNA sequence and these will be apparent to one skilled in the art. The invention includes nucleotide modifications of the sequences disclosed in this application (or fragments thereof) that are capable of expressing genes in epithelial cells. For example, the. K18Epilong sequence may be modified or a gene to be expressed may be modified using techniques known in the art. Modifications include substitution, insertion or deletion of nucleotides or altering the relative positions or order of nucleotides. The invention includes DNA which has a sequence with sufficient identity to a nucleotide sequence described in this application to hybridize under stringent hybridization conditions (hybridization techniques are well known in the art). The expression cassettes of the invention also include expression cassettes (or a fragment thereof) with nucleotide sequences having at least 70% identity, at least 80% identity, at least 90% identity, at least 95% identity, at least 96% identity, at least 97% identity, at least 98% identity or, most preferred, at least 99% identity to the expression cassette sequences of the invention, or a fragment thereof, including k18pSEAP, K18iSEAP, K18ESEAP, K18EpSEAP, K18EpiSEAP, K18EpilongSEAP, K18EplongSEAP, K18EplongSEAPi; K18Epilong, K18EpilongTECFTR, K18EpilongmCFTR (pK18mCFTR), [SEQ ID NO:1]), pCC10SEAPII, pCC10K18ISEAPII, pCC10K18I and K18EpilongmTELacZ [SEQ ID NO:1] (FIG. 4c). The invention also includes nucleotide modifications of the aforementioned sequences that are capable of expressing genes in epithelial cells. Identity refers to the similarity of two nucleotide sequences that are aligned so that the highest order match is obtained. Identity is calculated according to methods known in the art. For example, if a nuceotide sequence (called "Sequence A") has 90% identity to a portion of [SEQ ID NO: 1], then Sequence A will be identical to the referenced portion of [SEQ ID NO: 1] except that Sequence A may include up to 10 point mutations (such as deletions or substitutions with other nucleotides) per each 100 nucleotides of the referenced portion of [SEQ ID NO: 1].

The invention also includes fragments of the sequences, for example fragments comprising two or more of the human regulatory elements of the invention which are operatively combined for expression in epithelial cells. The invention also includes DNA sequences which are complementary to the aforementioned sequences. One skilled in the art would also appreciate that as other regulatory elements in cytokeratin 18 or CFTR are identified, these may be used with the expression cassettes of the invention. Regulatory elements from other genes are also used. As well, regulatory elements from the cytokeratin 18 gene in mammals other than humans could be inserted in the cassette provided that adequate gene expression still occurs. Other genes similar to the cytokeratin 18 gene may also be used in the expression cassettes. For example, the cytokeratin 18 gene and the cytokeratin 8 gene are expressed in pairs in humans so certain regulatory elements from the cytokeratin 8 gene could be used in the cassettes in addition to, or in place of, cytokeratin 18 regulatory elements. Reguatory elements from other cytokeratin genes are also useful sources of regulatory elements for the expression cassettes of the invention (human cytokeratin genes 1 to 19 are known; cytokeratin genes that are only expressed in skin are less likely to be useful for expression cassettes in lung epithelial tissue). Regulatory elements and sequences of other genes, such as cytokeratin genes, are known in the art. These regulatory elements may easily be inserted in expression cassettes of the invention and the levels of expression measured. For example, sequences from other cytokeratin genes or cytokeratin 18 genes from other mammals having a high level of sequence identity to the human regulatory elements used in the expression cassettes of the invention (such as cytokeratin 18 regulatory elements) may be easily identified by reviewing sequences from a database, such as Genbank. Suitable sequences preferably have at least 70% identity, at least 80% identity, at least 90% identity, at least 95% identity, at least 96% identity, at least 97% identity, at least 98% identity or most preferably have at least 99% identity to the sequence of a regulatory element (such as a cytokeratin 18 regulatory element) used in the cassettes of the invention disclosed in this application (or a fragment thereof).

Figure 3:
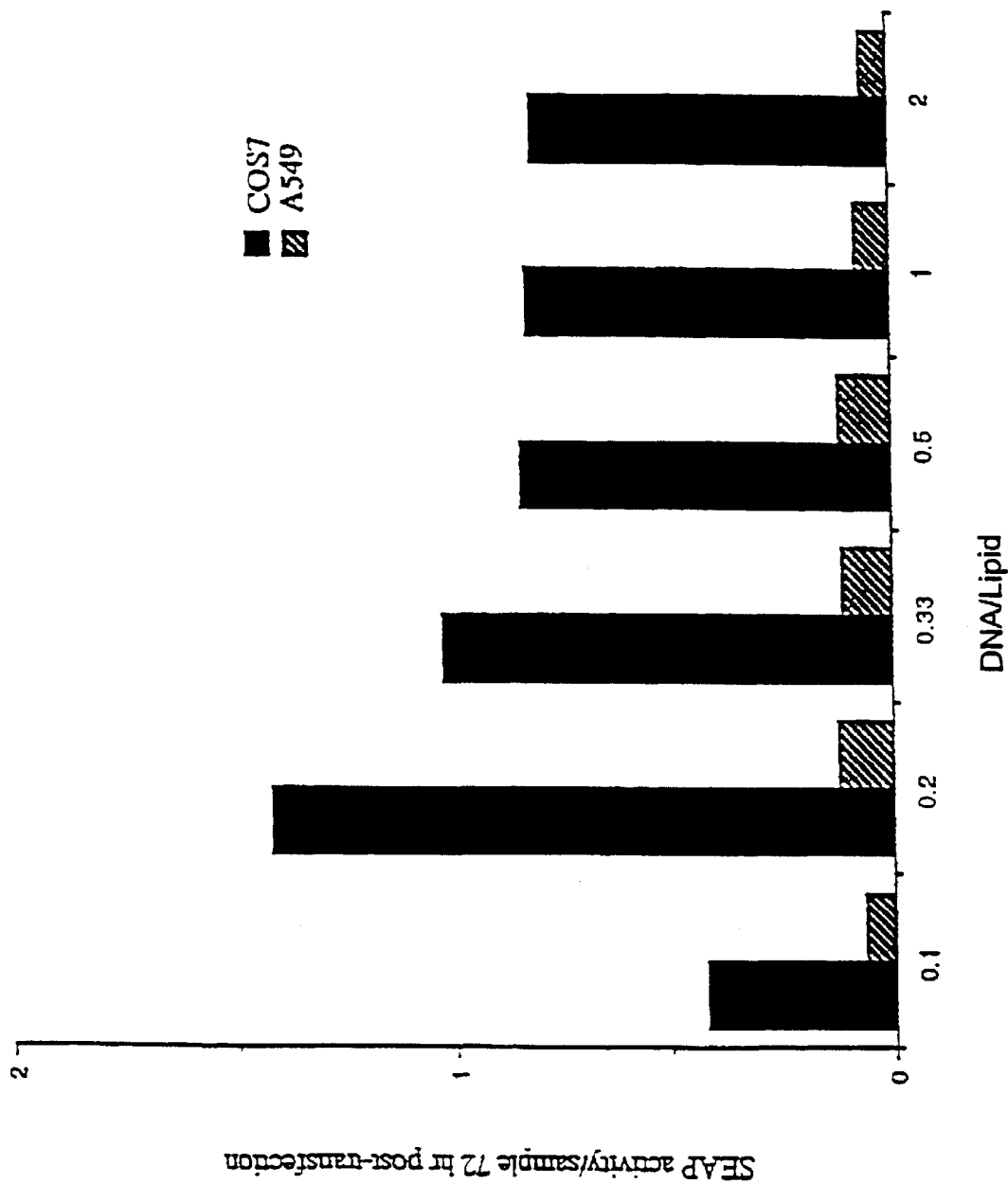
FIG. 3 Optimization of cell transfection conditions for gene expression. Cells were transfected with pCEP4SEAP complexed with DODAC:DOPE at 2.5 nmol/cm$^2$. Each sample corresponds to 50 $\mu$l of culture medium conditioned by the transfected cells.

Regulatory elements from other genes can be inserted in the expression cassettes. For example, the CC10 promoter (the CC10 sequence is available from the Genbank database; the sequence and other information relating to it in the Genbank database is incorporated by reference) could be substituted in a cassette in place of the K18 promoter. Combinations of regulatory regions can be used to vary the levels of protein production and/ or to obtain more cell specific expression. The techniques described to produce an expression cassette with human regulatory elements from the cytokeratin 18 gene may also be used to produce expression cassettes from other genes. Clara cells are non-ciliated secretory epithelial cells in the lung airways and they are believed to be important in metabolism of xenobiotics and regeneration of the airway epithelium (Boyd, M. R. 1977, *Nature*, 269:713–715; Singh et al. 1990, *Biuochimica et Biophysica Acta* 1039:348–355). Their major secretory product is called Clara cell 10 kD protein, or CC10, which is implicated in regulation of lung inflammation. We isolated a 3.3 kb DNA sequence corresponding to the promoter and the upstream region of the human CC10 gene by PCR-cloning. We inserted this DNA fragment into pSEAPII vector (Tropix) to create the plasmid, pCC10SEAPII, for expressing the Secreted Alkaline Phosphatase (SEAP) reporter gene. To enhance gene expression driven by the CC10 promoter/enhancer in non-Clara cells of lung epithelia, we built the construct, pCC10K18ISEAPII, by inserting intron I of the human K18 gene to the upstream of the SEAP coding sequence. The levels of reporter gene activity of these constructs were assayed with A549 cells. As shown in FIG. 3, addition of the K18 intron greatly enhanced the activity of the CC10 promoter/enhancer in A549 cells where the CC10 gene is normally not expressed very well.

This broadening of cell-specificity to other lung epithelial cells could be quite useful. We also demonstrated here that the K18 intron can be functional when combined with the human CC10 gene promoter. The combination expression cassette may be further modified according to techniques apparent to one skilled in the art. The expression cassette may be used as a research tool or for protein production.

Other regulatory elements that control expression of the CC10 gene may also be used to produce an expression cassette. A clear advantage of using an expression cassette derived from CC10 and the gene it expresses is that cell specific expression may be obtained. Other genes may have human regulatory elements that are desirable to obtain less cell specific expression.

The DNA sequences of the invention (regulatory element sequences and therapeutic gene sequences) may be obtained from a cDNA library, for example using expressed sequence tag analysis. The nucleotide molecules can also be obtained from other sources known in the art such as genomic DNA libraries or synthesis.

CFTR Expression Cassettes

The examples below show how to make an expression cassette which may be used for CFTR (or its variants or other proteins with CFTR activity) in vivo and in vitro. The examples below are primarily directed to increase the expression of CFTR. However, there are situations where lower levels of CFTR expression are desired, such as when using the cassette as a research tool. In such a case, the expression of the cassette may be altered by incorporating only some of the features of the expression cassettes described below. The level of expression activity of a modified construct can be measured in an animal model according to methods known in the prior art. Additional changes in the regulatory elements described below may be made in the cassette to alter the level of activity. Regardless of which of the regulatory elements below are used in a cassette, or which additional elements or changes are added to the cassette described below, any variants using human regulatory elements to express genes in epithelial cells are included within the scope of the invention. Any variants using regulatory elements from cytokeratin genes specifically expressed in epithelial cells of any mammal, particularly the cytokeratin 18 gene, are also included within the invention.

For example, the K18EpilongmCFTR [SEQ ID NO:1] expression cassette, discussed below, is customized to produce high levels of CFTR in epithelial cells. Human cytokeratin 18 gene elements were combined with the CFTR gene. Both the regulatory elements in the K18Epilong sequence and the gene were modified as described in the examples below to maximize CFTR production by K18EpilongmCFTR [SEQ ID NO:1].

K18Epilong was customized to produce a CFTR expression cassette called K18EpilongTECFTR by inserting CFTR cDNA (FIG. 4c). The CFTR gene sequence was manipulated to enhance CFTR protein synthesis. A translational enhancer was added to the 5' end of the CFTR coding sequence and the translation initiation sequence was optimized according to the Kozak sequence.

The K18EpilongTECFTR cassette was further modified to increase CFTR protein synthesis. The modified expression cassette, called K18EpilongmCFTR (or pk18mCFTR) [SEQ ID NO: 1], caused improved RNA splicing efficiency and removed undesired RNA splice sites. In this cassette, the DNA sequence corresponding to the polypyrimidine tract of the K18 intron 1 was modified by changing the non-coding region of the CFTR gene. Five cytosine residues and three adenine residues were converted into thymine residues. These are translated into uracil in the pre-mRNA sequence (FIG. 10C). The 3' splice site of the K18 intron was modified by changing the first nucleotide, adenine, of the following exon to guanine (FIG. 10C). The coding region of the CFTR region was also altered to destroy the second cryptic 3' splice site. This was done by making a single nucleotide change (adenine to guanine; FIG. 10C) which did not alter the protein sequence. A restriction map for k18EpilongmCFTR [SEQ ID NO:1] is shown in FIG. 19. The table below describes the K18EpilongmCFTR [SEQ ID NO:1] expression cassette.

| Nucleotide Numbers (1–12143 bp) | Sequence Description |
| --- | --- |
| 1 (Kpn I)–2565 (Mlu I) | K 18 5' enhancer and promoter |
| 2566 (Mlu I)–3315 | K 18 intron 1 |
| 3316–3354 (Nco I) | Translational enhancer (TE) |
| 3355 (Nco I)–7955 (Pst I) | CFTR (Translation starts with ATG in Nco I) |
| 7956–9283 (Sal I) | SVS40 small + Ag intron + SV40 early poly A signal |
| 9284 (SaI I)–12143 | pSEAP (Tropix) backbone |

It is clear that the CFTR sequence can be taken out with Nco I and Pst I (Pst I is not unique). Other genes or gene fragments can be inserted in the expression cassette and expressed.

We analyze the expression cassette in CF knockout mice. We generate transgenic mice to express the human CFTR gene with the expression cassettes. We introduce the CFTR expression cassette into CF knockout mice by crossing the CFTR-expressing mice with the CF knockout mice and rescue the CF mice by expression of the human CFTR gene with the expression cassette. In addition, we evaluate the expression cassettes for CFTR expression by intratracheal or intravenous delivery of the plasmid DNA complexed with liposomes (Logan et al. 1995, *Gene Therapy* 2:38–49; Liu et al. 1995, *JBC* 270:24864–24870).

Some of the changes described above to optimize CFTR expression may be omitted if a low level of CFTR expression is desired. For example, if the adenine to guanine change in the CFTR coding region is omitted, CFTR will be produced, but at a lower level. Likewise, variations in the number of cytosine or adenine to thymine mutations may be made if CFTR expression is not destroyed. It would be obvious to one skilled in the art that other changes could be made to alter the levels of expression of CFTR.

The CFTR gene is one therapeutic protein which may be expressed in vivo or in vitro using the expression cassettes of the invention. Changes in the nucleotide sequence which result in production of a chemically equivalent (for example, as a result of redudancy of the genetic code) or chemically similar amino acid (for example where sequence similarity is present), may also be used as therapeutic proteins with the expression cassettes of the invention. For example, U.S. Pat. No. 5,240,846 discloses mutants of the CFTR gene having a silent mutation that stabilizes expression of the gene. U.S. Pat. No. 5,639,661 discloses genes encoding novel CF monomer proteins which have cystic fibrosis transmembrane conductance regulator (CFTR) protein activity.

Other Therapeutic Protein Expression Cassettes

Other therapeutic proteins or mutants may also be used with the cassette. The expression cassettes may be used to drive expression of the cytokine genes, such as Interleukin 10 (de, V. J. 1995, *Annals of Medicine* 27:537–541), to control inflammation in lung, or to drive expression of DNA sequences encoding angiogenesis inhibitors, such as endostain (O'Reilly et al. 1997, *Cell* 88:277–285) and angiostain (O'Reilly et al. 1994, *Cell* 79:315–328) to inhibit tumor formation. These genes may be inserted in the cassette and expressed using techniques described in this application as well as other techniques known in the art. We analyze the expression cassette in a broad range of carcinoma cell lines and oncomice. We also evaluate the expression cassette in cancer gene therapy by testing it in a variety of cancer cell lines, including those from lung, breast, and colon carcinomas.

The expression cassettes are useful in other epithelial tissue, in addition to lung epithelial tissue, because the K18 gene is expressed in the epithelial cells of other internal organs (see Example 3). The DNA regulatory elements of the expression cassettes described below are also useful to direct tissue-specific expression of therapeutic genes in epithelial cells of other organs. However, successful expression of a reporter gene in the right cell type by an expression vector does not guarantee a positive outcome when a therapeutic gene is inserted in the same cassette if the DNA sequence of the therapeutic gene interferes with transcription or subsequent RNA splicing. One skilled in the art can modify the expression construct to accommodate a therapeutic gene. The level of expression activity of a modified construct can be measured in an animal model according to methods known in the prior art.

Research Tool

Mammals and cells cultures transformed with the expression cassette of the invention are useful as research tools. Mammals and cell cultures are used in research according to numerous techniques known in the art. For example, one obtains mice that do not express CFTR and uses them in experiments to assess CFTR gene expression. Experimental groups of mice are transformed with expression cassettes containing different types of CFTR genes (or genes similar to CFTR or fragments of genes) to assess the levels of protein produced, its functionality and the phenotype of the mice (for example, lung structure).

A cell line (either an immnortalized cell culture or a primary cell culture) is transformed with an expression cassette of the invention containing a CFTR gene (or variants) to measure levels of expression of the gene and the activity of the gene.

Using Exogenous Agents in Combination With an Expression Cassette

Cystic fibrosis-associated cells transformed with the cassette expressing CFTR may be treated with compounds that mobilize the recombinant protein (CFTR or a protein having similar sequence and function) as well as mutant forms of CFTR that may already be produced by the cells, so that the native and/or recombinant protein is transported to the plasma membrane and generates chloride channels in the cells. U.S. Pat. No. 5,674,898 (Cheng et al.) discloses the use of agents such as carboxylic acid or carboxylate which treat defective chloride ion transport by mobilizing mutant CFTR protein.

Transplant of Cells Transformed With the Cassette

Cells transformed with an expression cassette of the invention may be used in epithelial tissue transplants according to techniques known in the art. Examples of the use of transformed epithelial tissue in transplants are in U.S. Pat. Nos. 4,980,286 and 5,399,346.

Transgenic Mice and Rat Primary Cells as Models of Expression Cassette Function in Humans We used transgenic mice to evaluate the cell-specificity of the expression cassette because this is the most reliable approach to the analysis of mammalian gene expression at the whole organism level. We used rat primary epithelial and fibroblast cells with high purity for the evaluation because the freshly isolated primary cells retain their original properties better than the cultured cell lines. The transgenic mouse and rat primary cell models predict expression cassette function in humans.

EXAMPLE 1

Development of Reporter Genes for Liposome-mediated Plasmid Gene Transfer

For functional analysis of transcription regulatory elements, more than one reporter gene system is normally required because an extra reporter gene under a different promoter is needed to serve as an internal control to normalize the effects resulted from variation in transfection. In addition a particular reporter gene may not be compatible with a particular expression cassette. Therefore, we developed or adapted the following convenient reporter gene systems for lung gene expression studies:

1.1) GUS Reporter System.

Figure 1A:
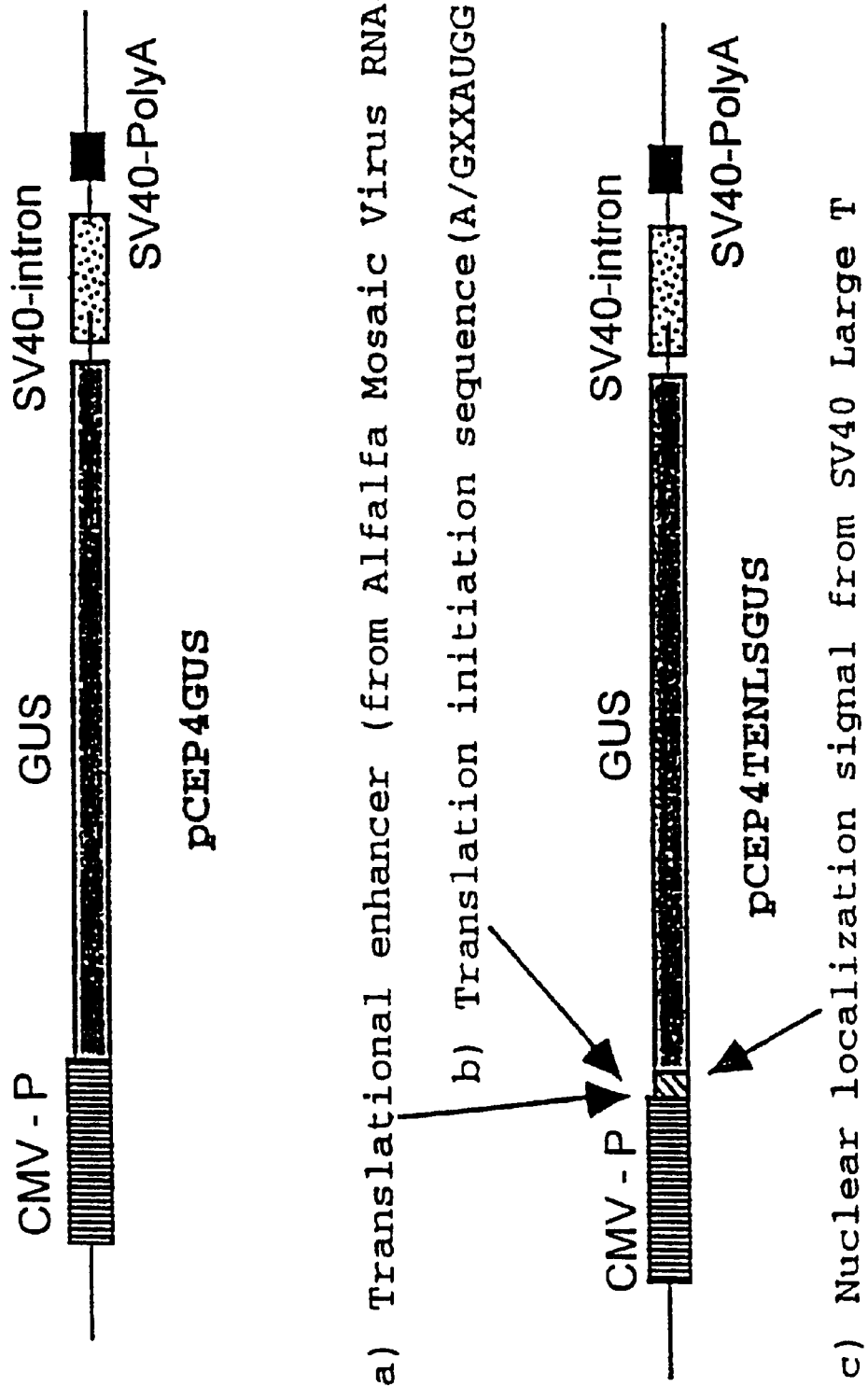
"FIGS. 1A–1B Improvement of GUS Reporter Gene System.
Figure 1B:
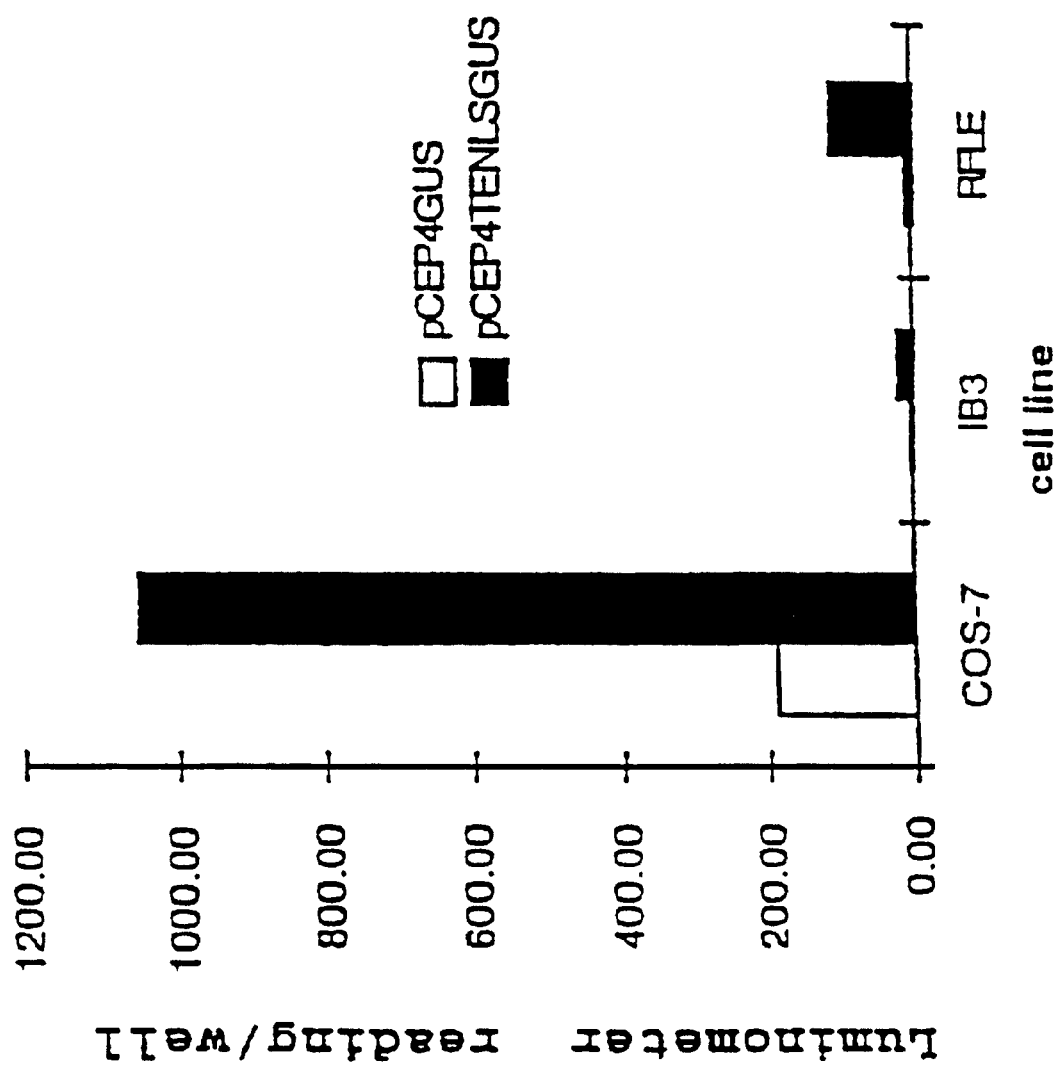

A bacterial gene (*E. coli* GUS, coding for b-glucuronidase) has worked well as a reporter gene in plants; its expression can be detected by either highly sensitive chemiluminescent assays (2, 3) or cell staining (16). Although b-glucuronidase activity is present in some mammalian cells, the optimal pH value for the mammalian enzyme is around 4–5 whereas that of the bacterial enzyme is around 7. We have subcloned the GUS gene into pCEP4 (Invitrogen) and transfected different cell lines and primary cells. We demonstrated that GUS can be a sensitive reporter for quantification of gene expression in lung cells. In order to further improve the sensitivity of GUS gene as a reporter, we added a translational enhancer (18) and a DNA sequence encoding a nuclear localization signal (19) to the 5' end of the GUS coding sequence. As shown in FIG. 1, GUS expression was greatly enhanced. We test and optimize the conditions for cell staining.

1.2) SEAP (secreted alkaline phosphatase) Reporter System.

We adapted SEAP as a primary reporter for gene expression in cultured cell lines and lung primary cells (FIGS. 3, 5 and 6) because the system is more economical and less labor-intensive than CAT or other reporter gene systems. The expression of SEAP can be quantified simply by chemiluminescent assay of the alkaline phosphatase secreted in culture media (2, 3).

1.3) GLP Reporter System.

Figure 2A:
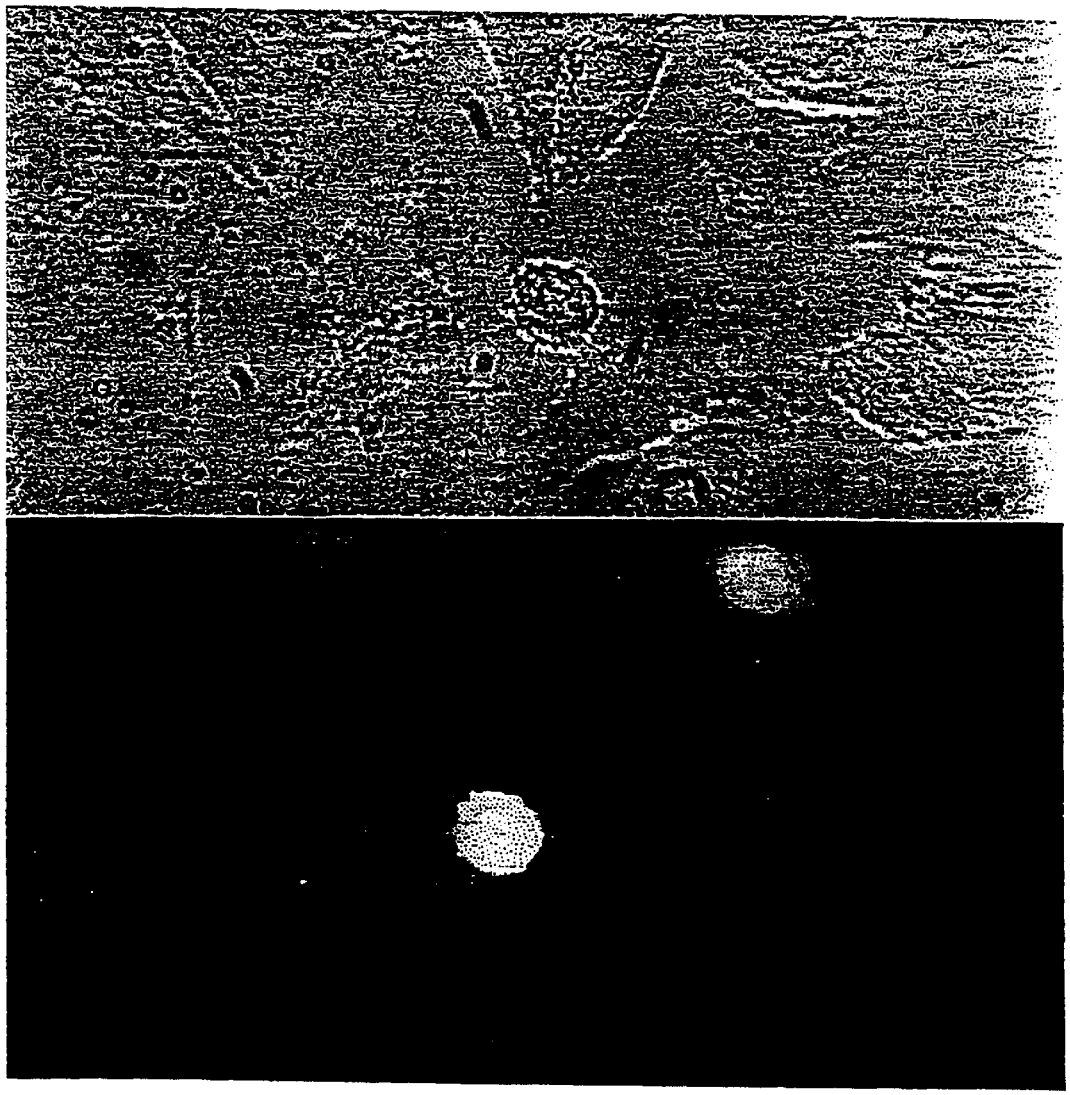
FIGS. 2A–2B Expression of GLP reporter in A547, IB3 and rat fetal lung primary epithelial cells.
Figure 2B:
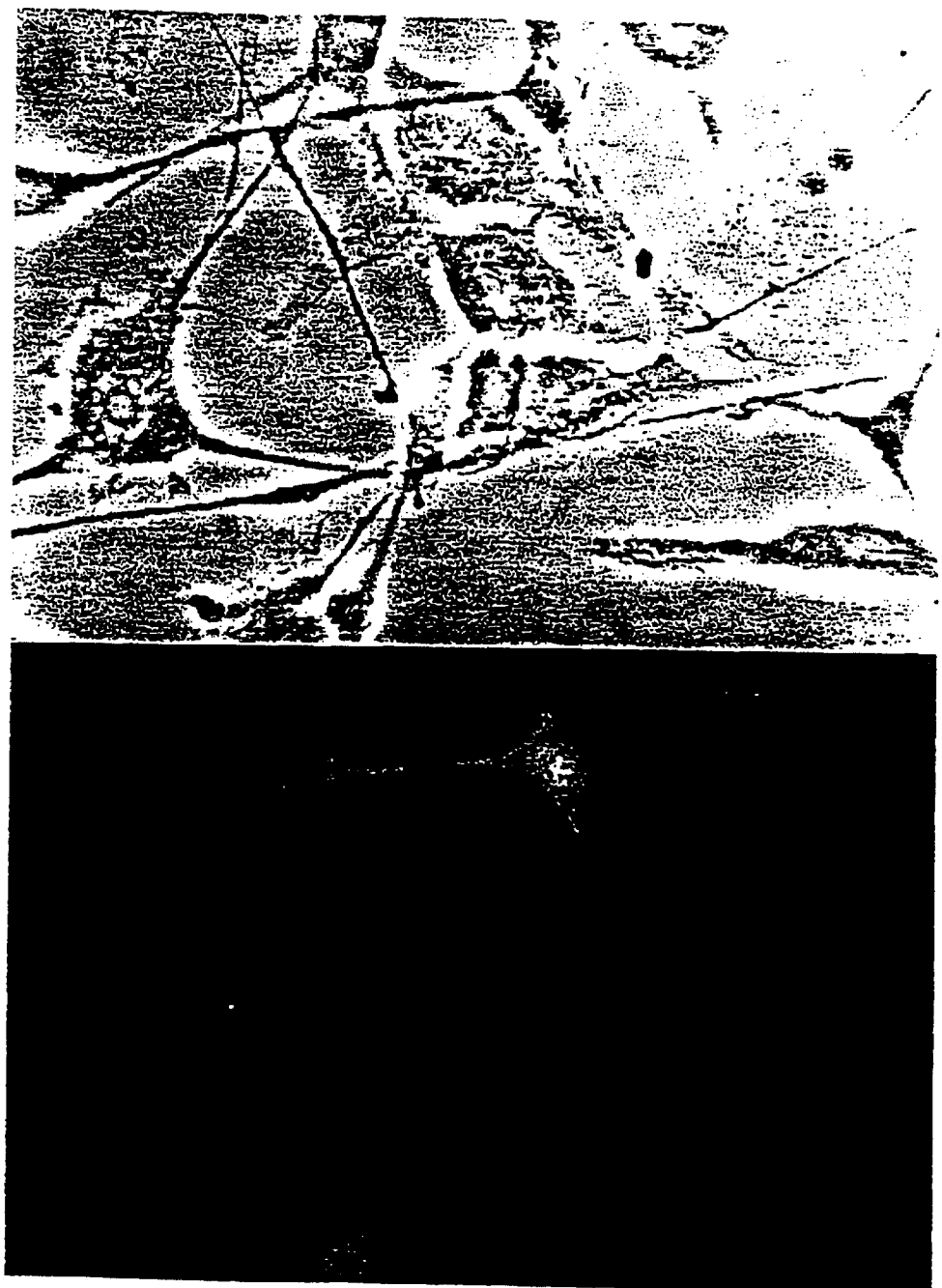
Figure 2C:
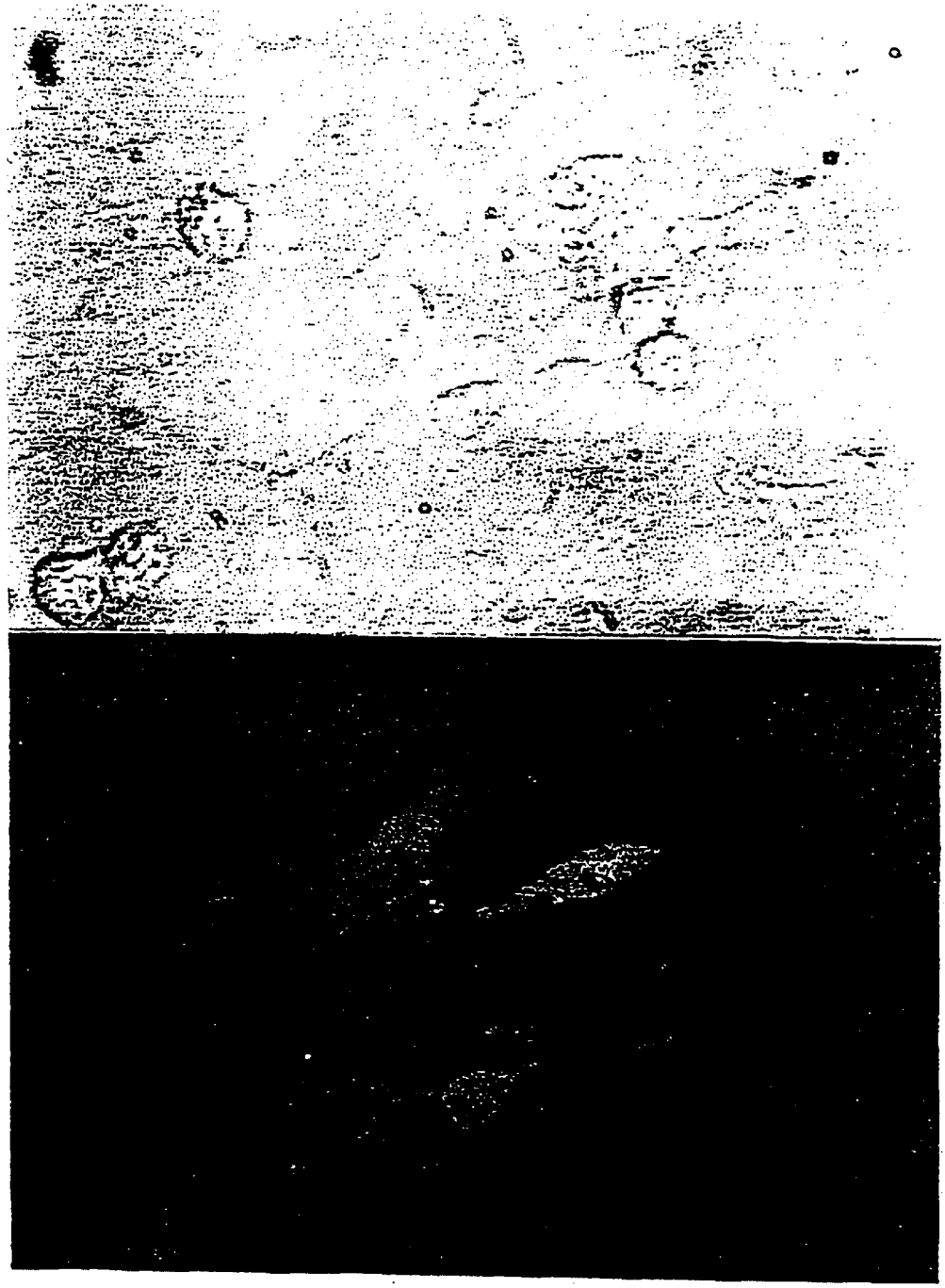
FIG. 2C shows expression of the green fluorescent protein in rat lung primary cells. Rat fetal lung epithelial cells were transfected with pGREENLANTERN-1 (GIBCO BRL) and visualized under a fluorescent microscope (bottom panel) 2 days post-transfection. The phase-contrast view of the same cells is shown in the top panel."

We also adapted the Green Lantern Protein (GLP, a modified version of green fluorescent protein) as a reporter to mark the cells transfected with liposome/DNA complex (FIG. 2).

The above systems may be modified and other markers may be incorporated into the expression cassettes.

EXAMPLE 2

Optimization of Transfection Conditions

We carried out experiments to optimize the transfection conditions because liposome-mediated gene expression in cell lines of lung origin is very inefficient. We used cell lines, such as, A549 (Human Lung Carcinoma cell line), IB3 (Cystic fibrosis bronchial epithelial cell line transformed with adeno-12-SV40;(45)), COS7 (SV40 transformed African Green monkey kidney), and WI38 (Hunan Lung diploid of fibroblast origin). There are many types of liposomes commercially available and a person skilled in the art is able to select suibable liposomes. We used DODAC:DOPE (INEX) because it is effective and large quantities will be available for clinical trials. For most of these cell lines, we found that about 2.5 nmol of DODAC:DOPE/$cm^2$ is optimal. FIG. 3 shows the effect of DNA:lipid ratio on gene expression in A549 and COS7 cells.

EXAMPLE 3

Construction of K18 Expression Constructs

Cytokeratins are major components of the epithelial cytoskeleton and different sub-types characterize different epithelia (26). The cytokeratin 18 gene is expressed predominately in internal organs (lung, liver, kidney and intestine) and brain. It is highly epithelium-specific and has been a useful marker of epithelial cell transitions in the remodeling adult lung (42, 43). The 2.5 kb sequence from the 5' region is able to direct lung gene expression in a copy number-dependent and position-independent manner in transgenic mice (28). Therefore, this region can be considered as a lung LCR (locus control region). A 3.5-kb 3' flanking sequence is required for gene expression in liver and intestine. There is a strong enhancer present in the first intron (29). To construct an expression cassette with the human cytokeratin 18 gene regulatory elements, we isolated the K 18 minimal promoter, intron 1 and two 5' fragments by PCR-cloning (FIG. 4). We found that any one of the elements alone could not direct SEAP expression in A549 or COS7 cells. The minimal promoter plus intron 1 has a low level of activity and the two fragments from the 5' region can greatly enhance the level of gene expression (FIG. 4). Since the 5' region and the intron 1 of the K18 gene are critical for high levels of gene expression, we decided to keep these elements in their original configuration as much as possible in construction of our first expression cassette, K18EpilongSEAP, to preserve the potential interactions among the transcription factors bound to these elements. In this reporter expression construct, the transcription will start from the K18 promoter, but protein translation will start from the first codon of the reporter gene because most of the K18 exon 1, including all the coding sequence, is deleted.

EXAMPLE 4

Episomal Expression of K18 Constructs in Cultured Cells

Figure 5:
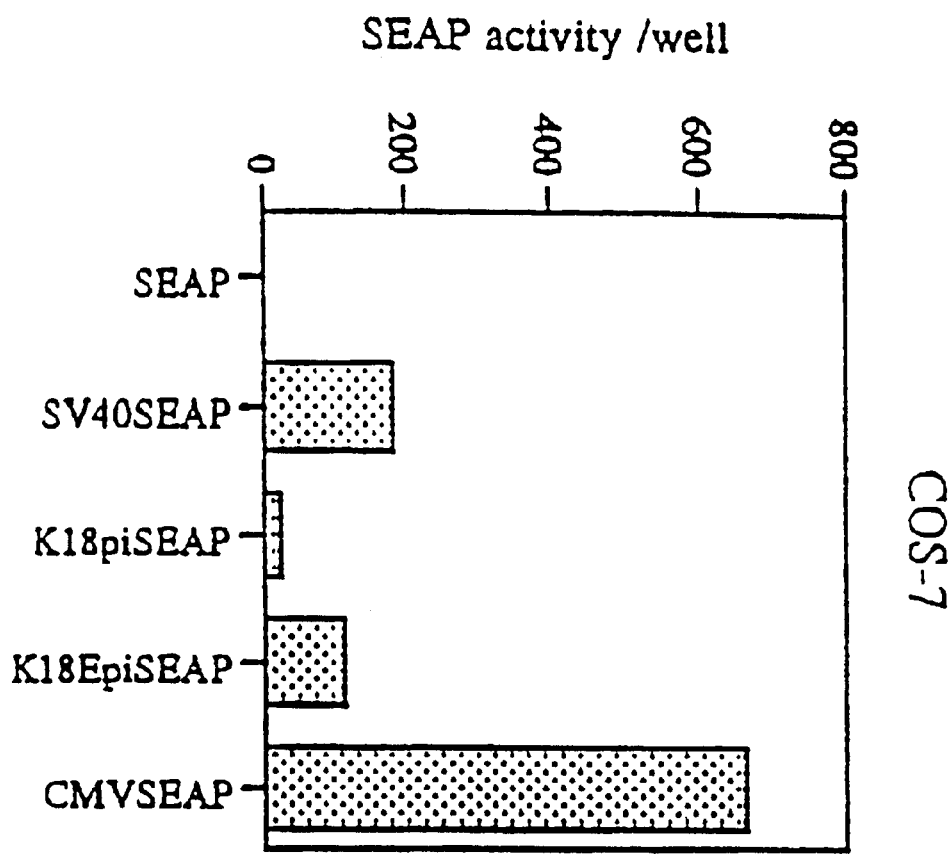
FIG. 5 Expression pattern of K18 constructs in comparison with SV40- or CMV-promoter directed expression in selected cell lines. A549, WI38, or COS-7 cells are transfected with DNA-lipid complex in parallel. Culture media were collected and assayed for SEAP activity 48 hr post-transfection.
Figure 6:
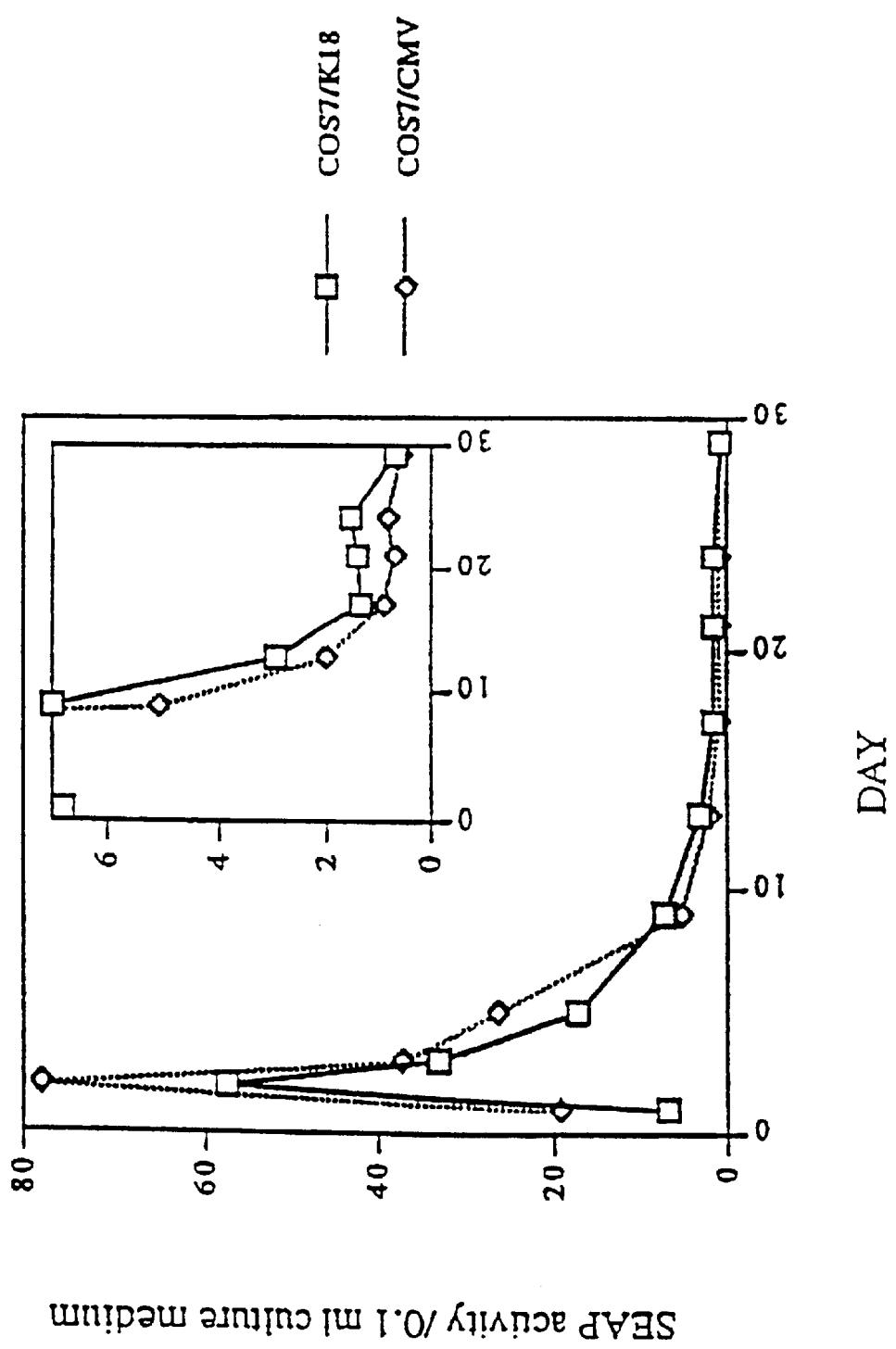
FIG. 6 Long lasting gene expression in cells transfected with K18EpilongSEAP. Shown are expression kinetics of K18EpilongSEAP versus CMVSEAP. A549 and COS-7 cells were transfected with DNA:lipid mix at 1:10 ratio. Culture media were collected at days post-transfection as indicated, prior to media change, and stored at −80° C. SEAP reporter assay was performed according to standard procedure.

To show that the episomal expression directed by K18 regulatory elements has epithelial specificity, we expressed K18EpiSEAP in A549 (human lung epithelial origin) and WI38 (human lung fibroblast origin). As shown in FIG. 5, K18EpiSEAP expressed the reporter gene only in A549, but not WI38, while the viral promoter, CMV, expressed in both cell lines (FIG. 5). The SV40 promoter was not active in these lung cell lines although it was fictional in COS7 cells which are monkey kidney cells transformed with SV40 large T antigen. Our results showed that K18EpilongSEAP is about 3 times more active than K18EpiSEAP (FIG. 15) and its expression lasted much longer than the CMV promoter in cell lines (FIG. 6). In vivo, the low levels of long lasting expression of the CFTR gene by K18Epilong offers more clinical benefits to patients in lung gene therapy than the transient expression from viral promoters. k18EpilongSEAP also exhibit clear cell specificity in that its expression can only be detected in A549 cells, but not WI38 or another human lung fibroblast line, HLF (data not shown).

EXAMPLE 5

Expression of K18Epilong in Primary Lung Epithelial Cells

Because promoters active in cell lines are often not active in primary cells, we decided to test the K18EpilongSEAP in rat lung primary cells. Although the K18Epilong expression in cell lines was much lower than that of CMV promoter, its expression in rat lung primary cells was better or comparable to that of CMV promoter (FIG. 7).

EXAMPLE 6 k18 CFTR Expression in Cell Lines and in Primary Cells

Figure 8:
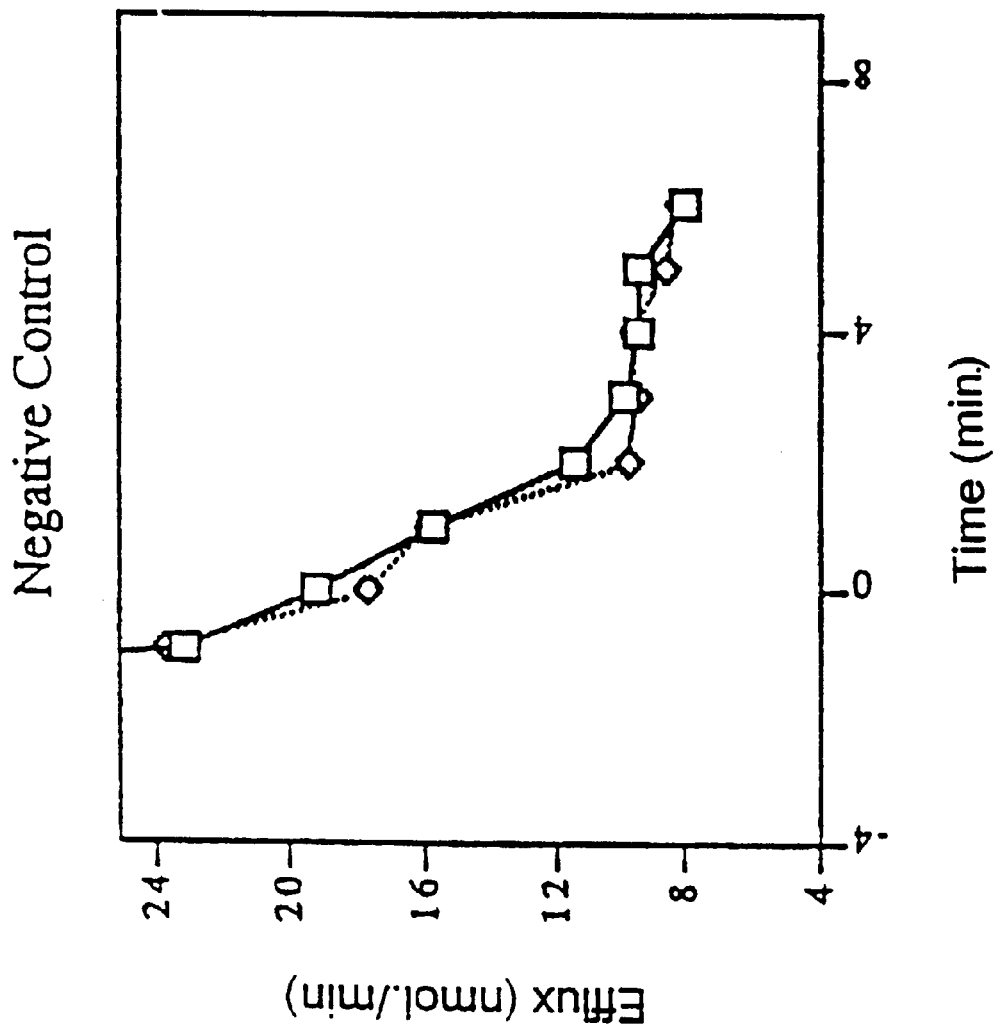
FIG. 8 I-Efflux of COS7 cells transfected with CFTR expression cassettes. Functional analysis for CFTR by iodide efflux assay. COS-7 cells were transfected with K18EpilongTECFTR, pCMVnot6.2CFTR as a positive control, or a negative control plasmid. 48 hr post-transfection, cells were loaded with iodide for one hour followed by extensive washes. AMP-dependent channel activity was then assessed as iodide concentration in the wells before and following the addition of the agonist, forskolin, at 0 time point.
Figure 9A:
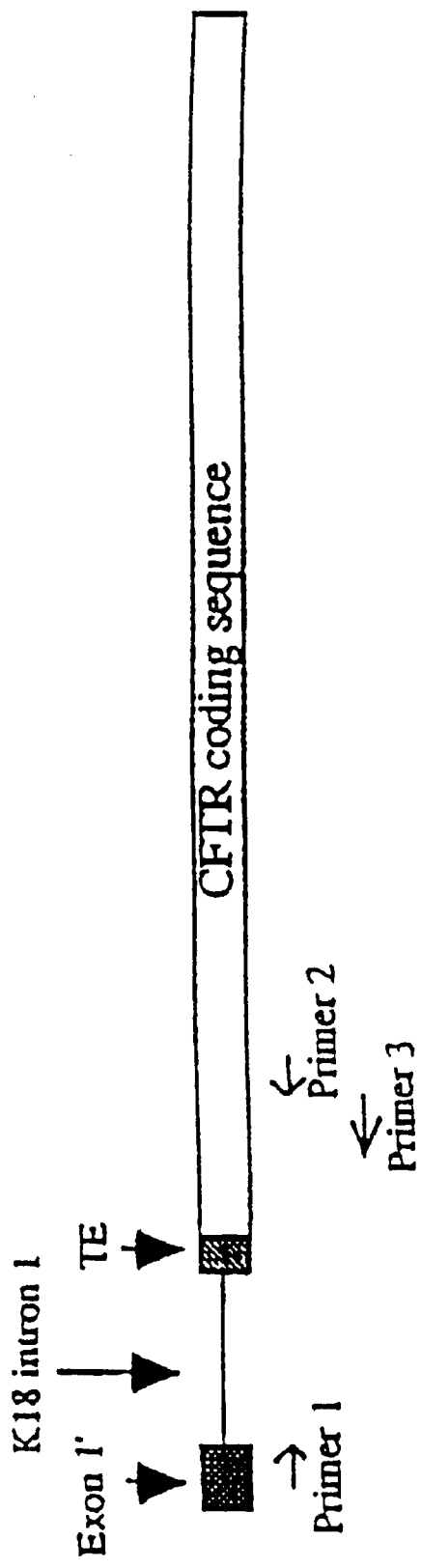
Figure 9B:
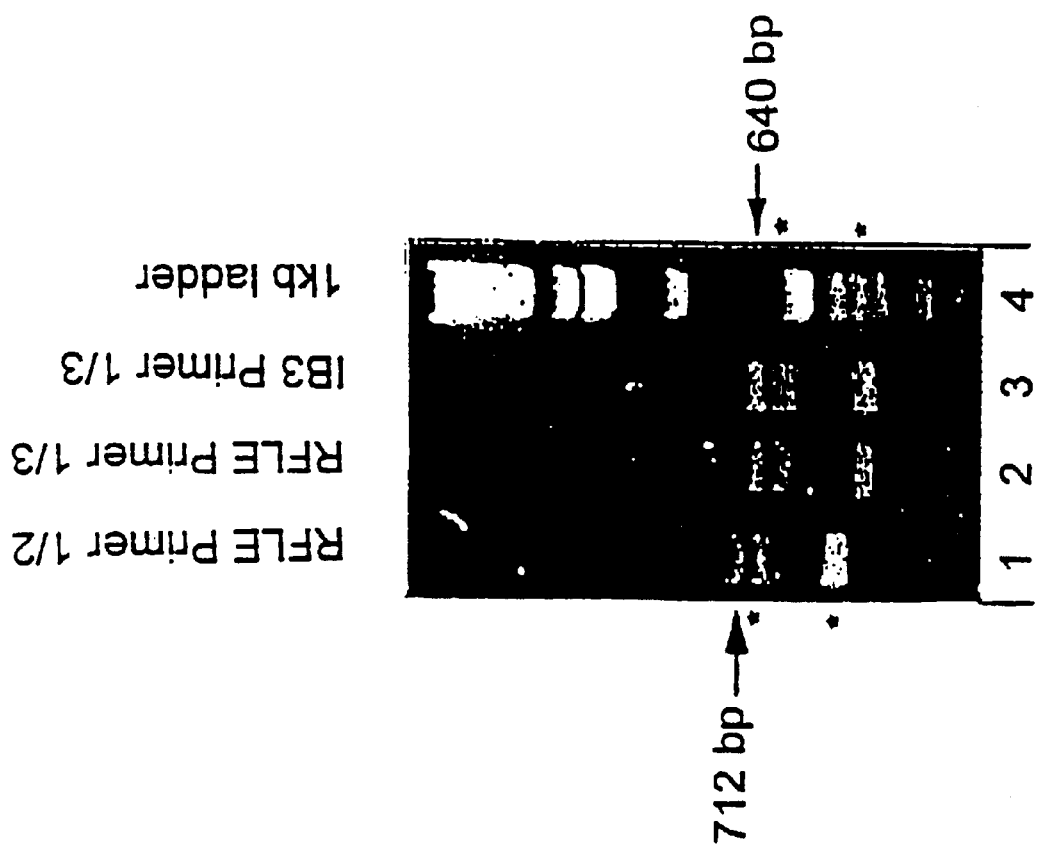

Because the K18Epilong can direct a high level of SEAP expression in rat lung primary cells, we built a CFTR expression cassette by replacing the SEAP coding sequence with CFTR cDNA to create K18EpilongTECFTR (FIG. 4c). The CFTR gene contains 27 exons and 26 introns, spanning over 250 kb on the long arm of human chromosome 7 (20, 30, 38); but the entire coding sequence is about 4.5 kilobases in length. In order to enhance CFTR protein synthesis, we added a translational enhancer (18) to the 5' end of the CFTR coding sequence and optimized the translation initiation sequence according to the Kozak sequence (23). To show that the CFTR gene was expressed from our expression cassette, we transfected COS7 cells with K18EpilongCFTR. FIG. 8 shows that the transfected cells have cAMP-dependent iodide effluxes, indicating that the episomally expressed CFTR can form functional channels in transfected cells. But, the activity of the CFTR channels was not as high as expected, indicating that the CFTR expression by this construct is not optimized. As shown in FIG. 9, we detected three CFTR mRNA species from transfected rat lung primary cells or IB3 cells using RT-PCR, indicating that two cryptic RNA splice-sites are activated; according to the sizes of the three PCR products, only about 25% of the mature CFTR species (the top band) are properly processed. Therefore, we modified the construct to improve the RNA splicing efficiency.

EXAMPLE 7

Optimizing RNA Splicing

There is not much known about the regulation of RNA splicing in lung cells, despite the important role that splicing can play in tissue-specific gene expression (35); e.g. the presence of rpL32 intron 3, which does not contain an enhancer, led to a 30-fold increase in mRNA relative to the intronless rpL32 minigene (21). Although the mechanism for stimulation of gene expression by regular introns is not clear, it is likely that the RNA splicing machinery may preferentially protect the intron-containing pre-mRNAs from nuclease degradation or facilitate the transport of the spliced mRNAs to cytoplasm. Because intron 1 of the cytokeratin 18 gene contains a strong enhancer that is required for gene expression, we included it in the K18-based CFTR expression cassette. But, incorporation of a heterologous intron into a cDNA sequence could potentially activate the cryptic splice-sites in the intron or in the cDNA and cause mis-splicing or alternative splicing. One potential solution to this problem is to put the intron after the coding sequence of the cDNA as long as the intron and/or intron-containing enhancer works from downstream. When the K18 intron 1 in K18EpilongSEAP is moved down stream of the reporter gene, expression of the reporter gene is greatly diminished (FIG. 16 ). Therefore, we modified the K18Epilongcftr to enhance the desired RNA splicing and to eliminate undesired RNA splice-sites.

Figure 11:
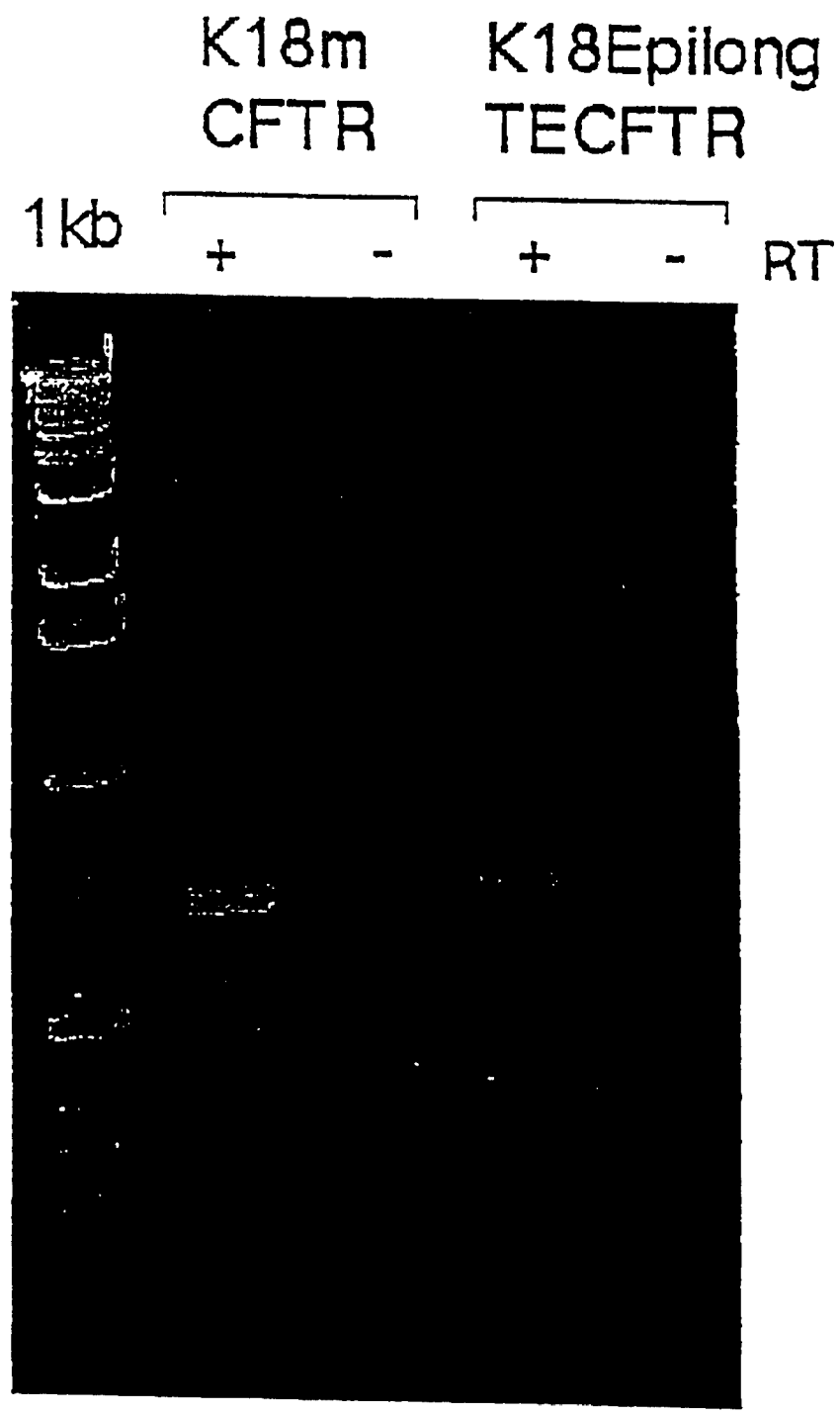
FIG. 11 Splicing patterns of K18-CFTR chimeric RNA transcripts. Shown are PCR products from reverse-transcribed (RT+) total RNAs isolated from A549 cells transfected with the indicated plasmids. The correctly-spliced transcript yields a 696 bp band, which is the only species in k18mCFTR transfected cells. In K18EpilongTECFTR transfected cells, two faster-migrating species, corresponding to splicing products utilizing the cryptic splice sites in the CFTR coding region, are present along with the 696 bp band.

Typical eukaryotic introns contain relatively conserved, short sequences recognized by the splicing machinery, spliceosome (27). The consensus sequences for the 5' splice site, the branch site and 3' splice site in mammals are AG/GURAGU, YNYURAC, and YAGM, respectively (R=purine, Y=pyrimidine, N=any nucleotide, and/indicates a splice site; the underlined nucleotides are completely conserved). In addition, a polypyrimidine tract is often present near the 3' splice site. We PCR-cloned the cDNA sequences derived from the alternatively spliced mRNAs and identified the splice-site junctions by DNA sequencing (FIG. 10B). We then realized that the poly U (uracil) sequence is the preferred polypyrimidine tract for the epithelial cells we used (FIG. 10B). We also noticed that the K18 intron 5' splice-site (AG/GUAAGG), putative branch-site (UUUUCAC), and 3' splice-site (CAG/A) are not highly conserved and can be potentially improved, since introns with more conserved sequences are, in general, spliced more efficiently (21). We modified the DNA sequence of pK18EpilongTECFTR corresponding to the polypyrimidine tract of the K18 intron 1 by changing five Cs (cytosine residues) and three As (adenine residues) into Ts (thymine residues), which will be translated into Us in the pre-mRNA sequence (FIG. 10C). We also modified the 3' splice site of the K18 intron by changing the first nucleotide, A, of the following exon to G (FIG. 10C). Since these nucleotides are not in the CFTR coding region, these changes would not effect the protein produced from the expression plasmid. In addition, we have made a single nucleotide change (A to G) in the CFTR coding region (see FIG. 10C) to destroy the second cryptic 3' splice site. We engineered the change in such a way so that the protein sequence remains the same and thus, the CFTR function will not be affected by this modification. This new construct was designated K18 EpilongmCFTR, or pK18mCFTR [SEQ ID NO: 1], and the previous version of plasmid was referred as K18EpilongTECFTR. As shown in FIG. 11, these changes very effectively eliminated the alternative RNA splicing and increased the steady state level of the CFTR mRNA.

Figure 12:
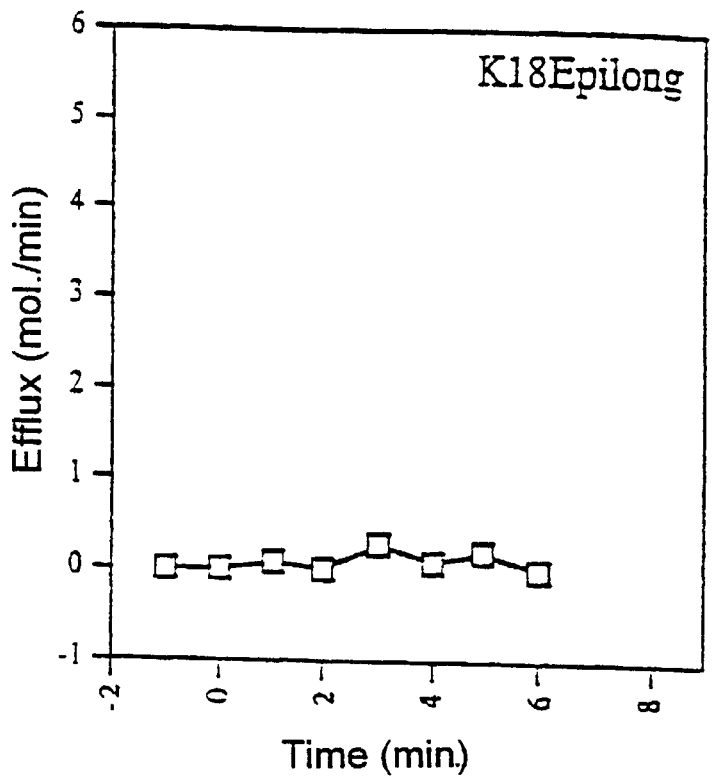
FIG. 12 Functional analysis of the CFTR channel activity by iodide efflux assay. COS-7 cells were transfected with K18EpilongTECFTR, K18EpilongmCFTR, pCDM8.1CFTR [SEQ ID NO:1] as a positive control, or a negative control plasmid (K18Epilong). Forty-eight hours post-transfection, cells were loaded with iodide for one hour followed by extensive washes. cAMP-dependent channel activity was then assessed as iodide concentration in the wells before and following the addition of the agonist, forskolin, at 0 time point.
Figure 12:
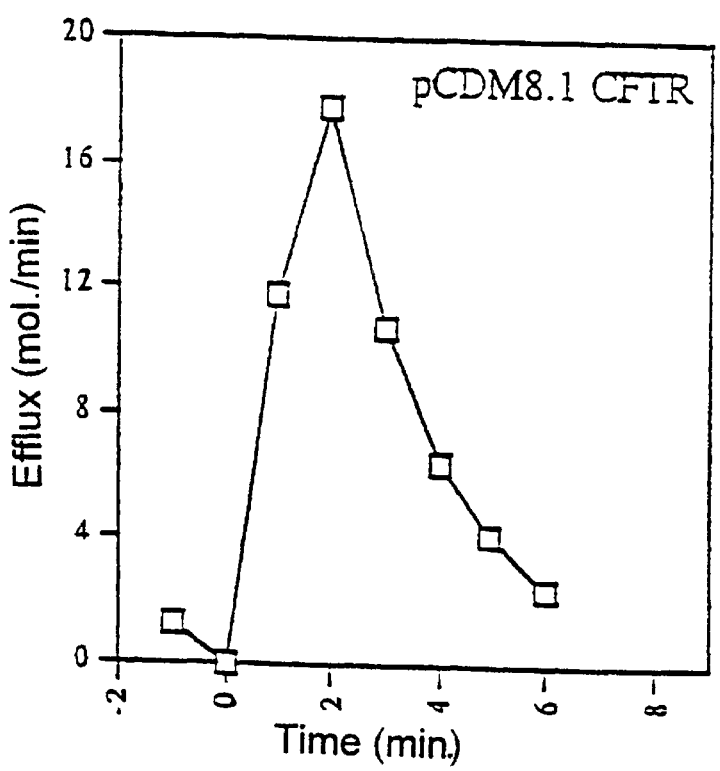

To show that the new construct expresses functional CFTR channels, we transfected COS7 cells and performed iodide efflux assays. As shown in FIG. 12, a higher level of CFTR channel activity was observed in cells transfected with K18EpilongmCFTR [SEQ ID NO:1] than in cells transfected with the previous construct.

EXAMPLE 8

Expression Analysis of the K18 Regulatory Elements in Transgenic Mice.

Figure 13:
FIG. 13 Targeting expression of the LacZ reporter gene in mouse lung epithelia.

To demonstrate that the modified K18 5' regulatory elements and intron 1 can direct cell-specific gene expression in lung epithelia in vivo, we carried out a transgenic analysis (28). The transgenic fetuses were identified by PCR and Southern blot analyses of the genomic DNA; the lungs of the 14 day fetuses were dissected out and stained with X-gal solution. These modified K18 DNA regulatory elements direct efficient and cell-specific expression of E. coli LacZ gene in lungs of the transgenic fetuses (FIGS. 13–14).

EXAMPLE 9

Expression in Calu-3 Cells

Since the human CFTR gene is heavily expressed in submucosal cells (12), we show that our epithelial expression cassettes function in these cells. The current available cell line that resembles the human submucosal cells is Calu-3 which was derived from a lung adenocarcinoma (available from the American Type Culture Collection). These cells express leukocyte protease inhibitor, lysozyme, and all markers of serous gland cells (34). They also express a high level of CFTR and when confluent, show polarization typical of epithelia.

To show that our expression cassettes direct gene expression in Calu-3 cells, we transfect these cells with K18EpilongSEAP and we perform quantitative assays of secreted alkaline phosphatase activity. The SEAP reporter system is the most convenient assay system because only a small amount of culture medium is required for each assay. The E. coli LacZ gene is also a useful reporter.

EXAMPLE 10

Expression in Lung Sections

We show the activity of the expression cassettes in vivo. A recently revived technique of lung slice culture (24, 39) is valuable for assessment of expression cassettes. Lungs of mice or rats are excised from anesthetized animals and inflated with 2% liquid agarose at 37° C. through trachea. Following cooling to 4° C., the lungs are cut into 0.2 to 1.0 mm thick slices and cultured overnight in cell culture medium. Cells in these lung slices can survive up to seven days (24, 39). Since more cell-cell interactions are maintained in the lung sections, gene expression in these sections should have more relevance to the gene expression in vivo. In addition to the preservation of cell-cell interactions, there are other reasons for utilization of this method; the transfection conditions for lung slices can be easily controlled and one mouse lung can be sectioned into many slices for testing many constructs at once while more animals have to be used for the same experiment in vivo. The mouse lung slices are transfected with K18EpilongLacZ construct with DODAC:DOPE in the same way as for cultured cells (see above) in a 6 well dish and cultured at 37° C. for two days. We use the LacZ as a reporter in lung slices because its β-galactosidase activity can be easily measured with chemiluminescent assays as well as cell-staining with X-gal. The transfected tissue slices are homogenized for β-galactosidase activity assay or fixed for (i) cell staining, (ii) in situ hybridization to detect cell-specificity of RNA expression, and (iii) fluorescent immunostaining of reporter gene products (the anti-β-galactosidase antibody is available from Clontech).

EXAMPLE 11

Expression in Model Animals

Gene expression studies in model animals are necessary for any expression cassette to be used for gene therapy because regulation of gene expression in model animals resembles that in human better than any other in vitro systems. We transfect CD1 mice in triplicates with K18EpilongLacZ using an intra-tracheal instillation technique established by Dr. O'Brodovich's group (at the Hospital for Sick Children, Toronto, Canada) and others. Other transfection techniques known in the art may also be used. A negative control plasmid, K18Epilong (vector) is included in the study. The β-galactosidase activity in lung cells is determined initially 2 days after transfection by using the chemiluminescent assays- To carry out a time course study, transfected mice are sacrificed at day 7, 14, 21, 28 post-transfection and the β-galactosidase activity in lung cells is assayed.

The best animal models available for cystic fibrosis are the CF knock-out mice, that are available in the Hospital for Sick Children, animal facility (Toronto, Canada). We express K18EpilongCFTR in CF knock-out mice. Dr. O'Brodovich has confirmed the observations (14) that UNC CF mice have a higher basal potential difference (PD) and fail to change their PD in response to lowed lumenal chloride concentration. We transfect the UNC CF knockout mice with our CFTR expression construct through intra-tracheal instillation. A vector plasmid is used as a negative control. The cell-specific expression of the human CFTR mRNA is assessed by fluorescent in situ RT-PCR and the human CFTR protein is detected by fluorescent immun-ostaining. Although there are not many high quality antibodies to CFTR available for in vivo detection, Demolombe et al. (8) have recently optimized the conditions for immmu-nofluorescent staining of human CFTR with a monoclonal antibody, MATG 1031. We also transfect the UNC CF mice with the same CFTR construct by nasal instillation and measure the nasal PD of the transfected mice.

EXAMPLE 12

Temporal Expression of the lacZ Gene

We analyzed temporal expression of the lacZ gene. FIG. 17 shows some of the results on β-galactosidase expression driven by K18 DNA regulatory elements in K18EpilongmTELacZ [SEQ ID NO:19] at different gestational ages in the transgenic mice.

EXAMPLE 13

Submucosal Expression of the lacZ Reporter Gene

Human airway submucosal glands play a major role in maintaining the volume and composition of airway surface fluid, which is important in airway clearance and protection from infection by microorganisms. FIG. 18 shows that the expression cassette we developed (K18EpilongmTELacZ) [SEQ ID NO:19] can target the lacZ reporter gene expression to submucosal glands in the trachea of adult transgenic mice.

The expression cassettes of this invention may be used in epithelial tissue gene therapy, particularly lung epithelial tissue gene therapy. The pharmaceutical compositions of this invention used to treat patients having degenerative diseases, disorders or abnormal physical states of the epithelial tissue could include an acceptable carrier, auxiliary or excipient. The conditions which may be treated by the expression cassettes include cystic fibrosis, emphysema, and cancers of epithelial origin arising in the lung or other organs.

The pharmaceutical compositions can be administered to humans or animals by methods such as aerosol administration, intratracheal instillation and intravenous injection. Dosages to be administered depend on patient needs, on the desired effect and on the chosen route of administration. The expression cassettes may be introduced into epithelial cells using in vivo delivery vehicles such as liposomes. They may also be introduced into these cells using physical techniques such as microinjection and electroporation or chemical methods such as coprecipitation and incorporation of DNA into liposomes. The expression cassette may be introduced into epithelial cells, such as submucosal cells, using these techniques. The expression cassettes may also be used in gene expression studies.

The pharmaceutical compositions can be prepared by known methods for the preparation of pharmaceutically acceptable compositions which can be administered to patients, and such that an effective quantity of the expression cassette is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as an episomal expression cassette and one or more genes to be expressed, in association with one or more pharmaceutically acceptable vehicles or diluents, and contained in buffered solutions with a suitable pH and isoosmotic with the physiological fluids. The methods of combining the expression cassettes with the vehicles or combining them with diluents is well known to those skilled in the art. The composition could include a targeting agent for the transport of the active compound to specified sites within the epithelial tissue.

Materials and Methods

Construction of reporter gene and CFTR expression cassettes. Polymerase chain reactions (PCR) were performed with pfu polymerase (Stratagene) and primer pairs (K18P3-5' GCAACGCGTCAGGTAAGGGGTAGG [SEQ ID NO: 2]/K18P4-5'CGAAGATCTGGAGGGATTGTAGAGAG [SEQ ID NO: 3]), (K18XH5'-5'CATAATAACGTCATTTCCTGCCC [SEQ ID NO: 4]/ K18P2*-5'GCTACGCGTGAGAGAAAGGACAGGACTC [SEQ ID NO: 5]), (K18NsiI-5'CTCACAGTAGGTGCTGAATGC [SEQ ID NO: 6]/K18XH3'-5'GACACGGACAGCAGGTGTTGTTG [SEQ ID NO: 7]) K18P1-5' CGAG GTACCAATAACAG-TAAAAGGCAGTAC [SEQ ID NO: 8]/K18NsiR-5'CACCGGTATATCACCTTTCCTGC [SEQ ID NO: 9]) on genomic DNA of human lung epithelial cells (A549) to isolate the first intron, minimal promoter, and two 5' untranslated regions, respectively, of human K18 gene. PCR products were verified by restriction mapping, according to restriction patterns predicted from published sequence, before cloning into the polylinker region of pSEAP(Tropix), via naturally-occurring restriction sites or sites introduced by PCR primers. The primers were purchased from ACGT Corp., Toronto and the PCR machine (DNA Engine, PTC-200), was purchased from Fisher.

The translation initiation sequence of the human CFTR cDNA was modified to introduce an Nco I site as well as to improve the initiation signal, according to Kozak's rule, by PCR using a cftrp1 primer (of sequence 5'GAGACCATG-GAGAGGTCG [SEQ ID NO: 10]). A linker containing the alfalfa mosaic virus translational enhancer (TE) sequence (5' GTTTTTATTTTTAATTTTCTTTCAAATACTTCCA [SEQ ID NO: 11]) was inserted immediately upstream of the Nco I site. The SEAP coding region in K18EpilongSEAP was then replaced with the TE4.6 kb CFTR cDNA fragment, resulting in the K18EpilongTECFTR construct.

PCR mutagenesis was performed on K18EpilongTECFTR using a 2-step nested PCR strategy. First-round PCR reactions incorporate primer pairs (TE2-5'GTCCGCAAAGCCTGAGTCCTGTCC [SEQ ID NO: 12]/K183'SS-5'AAATTAAAATAAAAACAGACCT-GAAAAAAAAAAGAGAGAGGTTGTT CCATGA [SEQ ID NO: 13]) and (TEtop-5'GATCTGTTTTTATTTT-TAATTTTCTTTCAAATACTTCCACCATGGCCCC [SEQ ID NO: 14]/cftr3'SS-5'GGTGACTTCCCCCAAATATAAAAAG [SEQ ID NO: 15]). Products from the first-round reactions were mixed and served as templates for the second-round PCR using TE2 [SEQ ID NO:15] and cftr3'SS primers. K18mCFTR construct was then generated by cloning the second-round PCR product back into K18EpilongTECFTR to replace the corresponding parental fragment.

Tissue Culture and Transfection. A549, a human lung carcinoma cell line, and COS-7 cells were cultured in Dulbecco's modified Eagle's medium, supplemented with 10% fetal bovine serum (FBS). Human lung fibroblasts, W138, were maintained in alpha minimum essential medium (alpha-MEM) with 10% FBS. IB3, a human cystic fibrosis bronchial epithelial cell line, was cultured in LHC-8 with 5% FBS. Day 19 rat fetal lung epithelium and fibroblast cells were isolated according to standard procedure and maintained in alpha-MEM with 10% FBS.

For transfection, cells were seeded at 50–80% confluency in six-well plates and allowed to settle in their regular media for overnight. The cells were then transfected in serum-free media with lmg DNA premixed with 12 mg of lipofectamine (GibcoBRL) per well according to the recommended procedure. Primary cells were transfected with premixed DNA:lipid complexes consisting of 1.66 mg DNA and 16.6 mg DODAC: DOPE (1:1 dioleyldimethylammonium chloride:dioleoylphosphatidylethanolamine, INEX) in serum-free media for 24 hr.

Reporter Assay. Culture media from transfected plates were collected at indicated time points post-transfection, before changes of media, and centrifuged 1 min at 16,000×g. Supernatant was frozen at −80° C. or assayed immediately. Secreted alkaline phosphatase activities in the media were detected with Phospha-Light chemiluminescent assay system (Tropix) as recommended and measured on a luminometer (BioOrbit).

Detection of CFTR mRNA. DNase I treated total RNA from transfected cells, prepared with RNeasy column (Qiagen), was subjected to reverse transcription, followed by PCR (30 cycles) using TE1 (5'CTGTCCTTTCTCTCACGCGTCAG [SEQ ID NO: 16]) or TE2 [SEQ ID NO:12] in combination with cftrp2 (5'GAGGAGTGCCACTTGC [SEQ ID NO: 17]) or cftrp3 (5'GTTGTTGGAAAGGAGACTAACAAG [SEQ ID NO: 18]) primers.

Functional Analysis of CFTR Protein. Iodide efflux assays were performed 48 hr post-transfection as previously described(5). Slight modifications were made on compositions of the loading buffer, which is 136 mM NaI, 4 mM KNO3, 2 mM Ca(NO$_3$)$_2$. 2 mM Mg(NO$_3$)$_2$. 11 mM glucose, and 20 mM HEPES, pH 7.4, and the agonists, 20 mM forskolin, 0.5 mM 8-(4-chlorophenylthio)-adenosine 3'; 5'-cyclic monophosphate (CPT-cAMP), and 0.5 mM 3-isobutyl-1-methylxanthine (IBMX).

Production of Transgenic Mice. The k18mLacZ construct was constructed by replacing the human CFTR coding region in the K18mCFTR plasmid with the *E. coli* LacZ gene. The K18mLacZ expression cassette was released by digestion with Kpn I. The DNA fragments were separated by agarose gel electrophoresis and purified through elutip (Schleicher & Schuell) following electroelution. The DNA fragments were microinjected into the pronuclei of fertilized eggs of STL/B16 mice. Fertilized eggs that proceeded into 2-cell stage were transferred to pseudo-pregnant CD1 recipients. The lungs of the 14 day fetuses were dissected out and stained with X-gal solution and the transgenic fetuses were identified by PCR and Southern blot analyses of the genomic DNA.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety. This application claims priority from Canadian application no. 2,205,076, which is incorporated by reference in its entirety.

References

1. Baskar, J. F., P. P. Smith, G. Nilaver, R. A. Jupp, S. Hoffinann, N. J. Peffer, D. J. Tenney, P. A. Colberg, P. Ghazal and J. A. Nelson. 1996. The enhancer domain of the human cytomegalovirus major immediate-early promoter determines cell type-specific expression in transgenic mice. Journal of Virology 70:3207–14.
2. Bronstein, I., J. Fortin, P. E. Stanley, G. S. Stewart and L. J. Kricka. 1994. Chemiluminescent and bioluminescent reporter gene assays. [Review]. Analytical Biochemistry 219:169–81.
3. Bronstein, I., J. J. Fortin, J. C. Voyta, R. R. Juo, B. Edwards, C. E. Olesen, N. Lijam and L. J. Kricka. 1994. Chemiluminescent reporter gene assays: sensitive detection of the GUS and SEAP gene products. Biotechniques 17:172–4.
4. Caplen, N. J., E. W. Alton, P. G. Middleton, J. R. Dorin, B. J. Stevenson, X. Gao, S. R. Durham, P. K. Jeffery, M. E. Hodson, C. Coutelle and a.l. et. 1995. Liposome-mediated CFTR gene transfer to the nasal epithelium of patients with cystic fibrosis [see comments]. Nature Medicine 1:39–46.
5. Chang, X. B., J. A. Tabcharani, Y. X. Hou, T. J. Jensen, N. Kartner, N. Alon, J. W. Hanrahan and J. R. Riordan. 1993. Protein kinase A (PKA) still activates CFTR chloride channel after mutagenesis of all 10 PKA consensus phosphorylation sites. Journal of Biological Chemistry 268:11304–11.
6. Colledge, W. H. 1994. Cystic fibrosis gene therapy. [Review]. Current Opinion in Genetics & Development 4:466–71.
7. Crystal, R. G. 1995. Transfer of genes to humans: early lessons and obstacles to success. [Review]. Science 270:404–10.
8. Demolombe, S., I. Baro, Z. Bebok, J.-P. Clancy, E. J. Sorscher, A. Thomas-Soumarmon, A. Pavirani and D. Escande. 1996. A method for the rapid detection of recombinant CPTR during gene therapy in cystic fibrosis. Gene Therapy 3:685–694.

9. Ellis, J., D. Talbot, N. Dillon and F. Grosveld. 1993. Synthetic human beta-globin 5'HS2 constructs function as locus control regions only in multicopy transgene concatamers. Embo Journal 12:127–34.
10. Ellis, J., U. K. Tan, A. Harper, D. Michalovich, N. Yannoutsos, S. Philipsen and F. Grosveld. 1996. A dominant chromatin-opening activity in 5'hypersensitive site 3 of the human beta-globin locus control region. Embo Journal 15:562–8.
11. Engelhardt, J. F., R. H. Simon, Y. Yang, M. Zepeda, P. S. Weber, B. Doranz, M. Grossman and J. M. Wilson. 1993. Adenovirus-mediated transfer of the CFTR gene to lung of nonhuman primates: biological efficacy study. Human Gene Therapy 4:759–69.
12. Engelhardt, J. F. and J. M. Wilson. 1992. Gene therapy of cystic fibrosis lung disease. Journal of Pharmacy & Pharmacology 1:165–7.
13. Grosveld, F., M. Antoniou, M. Berry, B. E. De, N. Dillon, J. Ellis, P. Fraser, O. Hanscombe, J. Hurst, A. Imain and a. l. et. 1993. The regulation of human globin gene switching. [Review]. Philosophical Transactions of the Royal Society of London Series B: Biological Sciences 339:183–91.
14. Grubb, B. R., R. N. Vick and R. C. Boucher. 1994. Hyperabsorption of Na+ and raised Ca(2+)-mediated Cl-secretion in nasal epithelia of CF mice. American Journal of Physiology 266:C1478–C1483.
15. Hazinski, T. A. 1993. Gene transfection of lung cells in vitro and in vivo. [Review]. Annual Review of Physiology 55:181–207.
16. Jefferson, R. A., T. A. Kavanagh and M. W. Bevan. 1987. GUS fusions: beta-glucuronidase as a sensitive and versatile gene fusion marker in higher plants. Embo Journal 6:3901–7.
17. Jeong, S. and A. Stein. 1994. Micrococcal nuclease digestion of nuclei reveals extended nucleosome ladders having anomalous DNA lengths for chromatin assembled on non-replicating plasmids in transfected cells. Nucleic Acids Research 22:370–5.
18. Jobling, S. A. and L. Gehrke. 1987. Enhanced translation of chimaeric messenger RNAs containing a plant viral untranslated leader sequence. Nature 325:622–5.
19. Kalderon, D., B. L. Roberts, W. D. Richardson and A. E. Smith. 1984. A short amino acid sequence able to specify nuclear location. Cell 39 (3Pt2):499–509.
20. Kerem, B., J. M. Rommens, J. A. Buchanan, D. Markiewicz, T. K. Cox, A. Chakravarti, M. Buchwald and L. C. Tsui. 1989. Identification of the cystic fibrosis gene: genetic analysis. Science 245:1073–80.
21. Korb, M., Y. Ke and L. F. Johnson. 1993. Stimulation of gene expression by introns: conversion of an inhibitory intron to a stimulatory intron by alteration of the splice donor sequence. Nucleic Acids Research 21:5901–8.
22. Korfhagen, T. R., S. W. Glasser and B. R. Stripp. 1994. Regulation of gene expression in the lung. [Review]. Current Opinion in Pediatrics 6:255–61.
23. Kozak, M. 1991. Structural features in eukaryotic miRNAs that modulate the initiation of translation. [Review]. Journal of Biological Chemistry 266:19867–70.
24. Kurosawa, H., C. G. Wang, R. J. Dandurand, M. King and D. H. Eidelman. 1995. Mucociliary function in the mouse measured in explanted lung tissue. Journal of Applied Physiology 79:41–6.
25. Mitchell, P. J. and R. Tjian. 1989. Transcriptional regulation in mammalian cells by sequence-specific DNA binding proteins. [Review]. Science 245:371–8.
26. Moll, R., W. W. Franke, D. L. Schiller, B. Geiger and R. Krepler. 1982. The catalog of human cytokeratins: patterns of expression in normal epithelia, tumors and cultured cells. [Review]. Cell 31:11–24.
27. Moore, M. J., C. C. Query and P. A. Sharp. 1993. Splicing of precursers to mRNA by the spliceosome. In The RNA World. chapter 13:303–357.
28. Neznanov, N., I. S. Thorey, G. Cecena and R. G. Oshima. 1993. Transcriptional insulation of the human keratin 18 gene in transgenic mice. Molecular & Cellular Biology 13:2214–23.
29. Pankov, R., N. Neznanov, A. Umezawa and R. G. Oshima. 1994. AP-1, ETS, and transcriptional silencers regulate retinoic acid-dependent induction of keratin 18 in embryonic cells. Molecular & Cellular Biology 14:7744–57.
30. Romrnens, J. M., M. C. lannuzzi, B. Kerem, M. L. Drumm, G. Melmer, M. Dean, R. Rozmahel, J. L. Cole, D. Kennedy, N. Hidaka and a. l. et. 1989.
Identification of the cystic fibrosis gene: chromosome walking and jumping. Science 245:1059–65.
31. Rooney, S. A., S. L. Young and C. R. Mendelson. 1994. Molecular and cellular processing of lung surfactant. [Review]. Faseb Journal 8:957–67.
32. Sawaya, P. L., B. R. Stripp, J. A. Whitsett and D. S. Luse. 1993. The lung-specific CC10 gene is regulated by transcription factors from the AP-1, octamer, and hepatocyte nuclear factor 3 families. Molecular & Cellular Biology 13:3860–71.
33. Schmidt, E. V., G. Christoph, R. Zeller and P. Leder. 1990. The cytomegalovirus enhancer: a pan-active control element in transgenic mice. Molecular & Cellular Biology 10:4406–11.
34. Shen, B. Q., W. E. Finkbeiner, J. J. Wine, R. J. Mrsny and J. H. Widdicombe. 1994. Calu-3: a human airway epithelial cell line that shows cAMP-dependent Cl- secretion. American Journal of Physiology 266(5Pt 1)::L493–501.
35. Smith, C. W., J. G. Patton and G. B. Nadal. 1989. Alternative splicing in the control of gene expression. [Review]. Annual Review of Genetics 23:527–77.
36. Talbot, D., P. Descombes and U. Schibler. 1994. The 5' flanking region of the rat LAP (C/EBP beta) gene can direct high-level, position-independent, copy number-dependent expression in multiple tissues in transgenic mice. Nucleic Acids Research 22:756–66.
37. Tizzano, E. F., H. O'Brodovich, D. Chitayat, J. C. Benichou and M. Buchwald. 1994. Regional expression of CFTR in developing human respiratory tissues. American Journal of Respiratory Cell & Molecular Biology 10:355–62.
38. Tsui, L. C. 1995. The cystic fibrosis transmembrane conductance regulator gene. [Review]. American Journal of Respiratory & Critical Care Medicine 151:S47–53.
39. Vallan, C., R. R. Friis and P. H. Burri. 1995. Release of a mitogenic factor by adult rat lung slices in culture. Experimental Lung Research 21:469–87.
40. Venkatesh, V. C., B. C. Planer, M. Schwartz, J. N. Vanderbilt, R. T. White and P. L. Ballard. 1995. Characterization of the promoter of human pulmonary surfactant protein B gene. American Journal of Physiology 268:L674–682.
41. Wert, S. E., S. W. Glasser, T. R. Korfhagen and J. A. Whitsett. 1993. Transcriptional elements from the human SP-C gene direct expression in the primordial respiratory epithelium of transgenic mice. Developmental Biology 156:426–43.

42. Woodcock, M. J., K. B. Adler and R. B. Low. 1984. Inmunohistochemical identification of cell types in normal and in bleomycin-induced fibrotic rat lung. Cellular origins of interstitial cells. American Review of Respiratory Disease 130:910–6.
43. Woodcock, M. J., J. J. Mitchell, S. E. Reynolds, K. O. Leslie and R. B. Low. 1990. Alveolar epithelial cell keratin expression during lung development. American Journal of Respiratory Cell & Molecular Biology 2:503–14.
44. Zabner, J., A. J. Fasbender, T. Moninger, K. A. Poellinger and M. J. Welsh. 1995. Cellular and molecular barriers to gene transfer by a cationic lipid. Journal of Biological Chemistry 270:18997–9007.
45. Zeitlin, P. L., L. Lu, J. Rhim, G. Cutting, G. Stetten, K. A. Kieffer, R. Craig and W. B. Guggino. 1991. A cystic fibrosis bronchial epithelial cell line: immortalization by adeno-12-SV40 infection. American Journal of Respiratory Cell & Molecular Biology 4:313–9.

We claim:

1. An expression cassette for the episomal expression of a transgene in a targeted mammalian epithelial cell, comprising: a cytokeratin 18 5' region, a cytokeratin 18 promoter, and a cytokeratin 18 intron 1, wherein the expression cassette is capable of receiving a transgene for expression in the epithelial cell, with the proviso that the transgene is not cytokeratin 18.

2. The expression cassette of claim 1, wherein the cytokeratin 18 intron 1 comprises all or part of nucleotide nos. 2566 to 3315 of SEQ ID NO:1.

3. The expression cassette of claim 1, whwerein the cytokeratin 18 5' region and cytokeratin 18 promoter comprise all or part of nucleotide nos. 1 to 2565 of SEQ ID NO:1.

4. The expression cassette of claim 1, further comprising a translational enhancer.

5. The expression cassette of claim 4, wherein the translational enhancer comprises all or part of nucleotide nos. 3316 to 3354 of SEQ ID NO:1.

6. The expression cassette of claim 1, comprising all or part of nucleotide nos. 1 to 3354 and 7949 to 12143 of SEQ ID NO:1.

7. The expression cassette of claims 1, 2, 3, 4, 5 or 6, further comprising a transgene selected from the group consisting of (i) a nucleotide sequence comprising all or part of nucleotide nos. 3355 to 7955 of SEQ ID NO:1 (ii) a nucleotide sequence having at least 80% sequence identity with nucleotide nos. 3355 to 7955 of SEQ ID NO:1 and (iii) a nucleotide sequence encoding the same polypeptide that is encoded by nucleotide nos. 3355 to 7955 of SEQ ID NO:1.

8. The expression cassette of claim 7, wherein the cassette is modified in an intron selected from the group consisting of the k18 intron I 3' splice site, a CFTR intron 3' cryptic splice site-1 and a CFTR intron 3' cryptic splice site-2 thereby reducing alternative RNA splicing and increasing the steady state level of mRNA produced from the CFTR sequence.

9. The expression cassette of claim 8, wherein the transgene comprises all or part of nucleotide numbers 3355 to 7955 of SEQ ID NO:1 and an intron selected frorm the group consisting of nucleotides 3301 to 3304, 3306 to 3308, 3310, 3315 and 3624 of SEQ ID NO:1.

10. The expression cassette of claim 2, comprising all or part of the nucleotide sequence of SEQ ID NO:1.

11. An expression cassette comprising at least 80% sequence identity with a sequence selected from the group consisting of nucleotide nos. 1 to 3354, 7949 to 12143 of SEQ ID NO:1 and SEQ ID NO:1.

12. A vector comprising the expression cassette of claim 1.

13. The expression cassette of claim 1, wherein the epithelial cell is a lung epithelial cell.

14. The expression cassette of claim 13, wherein the lung epithelial cell is an airway epithelial cell or a submucosal cell.

15. A mammalian epithelial cell comprising the expression cassette of claim 1.

16. The mammalian epithelial cell of claim 15, wherein said mammalian epithelial cell is a human cell.

17. A composition comprising an effective amount of the expression cassette of claim 7 and a pharmaceutically acceptable carrier.

18. A composition comprising the expression cassette of claim 7 and a carrier.

19. A method for expressing a gene in a target epithelial cell, comprising:

administering to the epithelial cell an amount of the expression cassette of claims 1, 2, 3, 4, 5, 6, 9, 10 or 11 so that the expression cassette is inserted in the epithelial cell; and expressing a protein encoded by the transgene to produce the protein.

20. A method for increasing chloride channels in an epithelial cell, comprising:

administering to the epithelial cell an amount of the expression cassette of claims 1, 2, 3, 4, 5, 6, 9, 10 or 11 so that the expression cassette is inserted in the epithelial cell; and expressing a protein encoded by the transgene to produce the protein, wherein said protein is transported to the plasma membrane and generates chloride channels in the epithelial cell.

* * * * *